(12) United States Patent
Baker et al.

(10) Patent No.: US 11,702,467 B2
(45) Date of Patent: Jul. 18, 2023

(54) HIGH AFFINITY ANTIBODIES TARGETING TAU PHOSPHORYLATED AT SERINE 413

(71) Applicant: Merck Sharp & Dohme LLC, Rahway, NJ (US)

(72) Inventors: Jeanne E. Baker, Redwood City, CA (US); Sophie Parmentier Batteur, Haverford, PA (US); Ming-Tang Chen, Dover, MA (US); Alan C. Cheng, San Francisco, CA (US); Chung-Ming Hsieh, Newton, MA (US); Carl Mieczkowski, Hercules, CA (US); Sokreine Suon, King of Prussia, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/355,529

(22) Filed: Jun. 23, 2021

(65) Prior Publication Data

US 2021/0403541 A1 Dec. 30, 2021
US 2023/0167168 A9 Jun. 1, 2023

Related U.S. Application Data

(60) Provisional application No. 63/044,921, filed on Jun. 25, 2020.

(51) Int. Cl.

| C07K 16/28 | (2006.01) |
| C07K 16/18 | (2006.01) |
| A61P 25/28 | (2006.01) |
| C07K 16/06 | (2006.01) |
| C07K 16/40 | (2006.01) |
| C07K 16/44 | (2006.01) |
| A61P 25/00 | (2006.01) |

(Continued)

(52) U.S. Cl.
CPC ............ *C07K 16/18* (2013.01); *A61K 45/06* (2013.01); *A61P 25/00* (2018.01); *A61K 2039/505* (2013.01)

(58) Field of Classification Search
None
See application file for complete search history.

(56) References Cited

U.S. PATENT DOCUMENTS 5,624,821 A 4/1997 Winter et al.
5,677,425 A 10/1997 Bodmer et al.
(Continued)

FOREIGN PATENT DOCUMENTS

EP 1876185 A1 1/2008
EP 2857039 A1 4/2015
(Continued)

OTHER PUBLICATIONS

Clackson et al., Making Antibody Fragments Using Phage Display Libraries, Nature, 1991, pp. 624-628, vol. 352.
(Continued)

*Primary Examiner* — Aurora M Fontainhas
(74) *Attorney, Agent, or Firm* — Sanjeev K. Mahanta; Alysia A. Einnegan

(57) ABSTRACT

Provided herein are high affinity antibodies or antigen binding fragments thereof that specifically bind to human tau-pS413. Also provided are compositions, kits, methods, and uses involving such antibodies or antigen binding fragments thereof.

33 Claims, 12 Drawing Sheets
(1 of 12 Drawing Sheet(s) Filed in Color)
Specification includes a Sequence Listing.

(51) Int. Cl.
*A61K 45/06* (2006.01)
*A61K 39/00* (2006.01)

(56) References Cited

U.S. PATENT DOCUMENTS

| | | | |
|---|---|---|---|
| 5,869,046 | A | 2/1999 | Presta et al. |
| 6,194,551 | B1 | 2/2001 | Idusogie et al. |
| 6,277,375 | B1 | 8/2001 | Ward |
| 6,350,861 | B1 | 2/2002 | Co et al. |
| 6,946,292 | B2 | 9/2005 | Kanda et al. |
| 7,029,872 | B2 | 4/2006 | Gerngross |
| 8,609,097 | B2 | 12/2013 | Bohrmann et al. |
| 8,647,631 | B2 | 2/2014 | Pfeifer et al. |
| 8,703,137 | B2 | 4/2014 | Chain |
| 8,748,386 | B2 | 6/2014 | Sigurdsson |
| 10,556,950 | B2 | 2/2020 | Eguchi et al. |
| 2002/0086009 | A1 | 7/2002 | Ishiguro et al. |
| 2004/0110704 | A1 | 6/2004 | Yamane et al. |
| 2007/0280935 | A1 | 12/2007 | Bohrmann et al. |
| 2008/0050383 | A1 | 2/2008 | Sigurdsson et al. |
| 2010/0316564 | A1 | 12/2010 | Sigurdsson |
| 2012/0087861 | A1 | 4/2012 | Nitsch et al. |
| 2015/0183854 | A1 | 7/2015 | Mori et al. |

FOREIGN PATENT DOCUMENTS

| | | | |
|---|---|---|---|
| JP | 2008013566 | A2 | 1/2008 |
| JP | 2012522754 | | 10/2012 |
| JP | 2012530055 | T2 | 12/2012 |
| WO | 199429351 | A2 | 12/1994 |
| WO | 1997034145 | A1 | 9/1997 |
| WO | 199954342 | A1 | 10/1999 |
| WO | 200042072 | A2 | 7/2000 |
| WO | 2003035835 | A2 | 5/2003 |
| WO | 2005120571 | A2 | 12/2005 |
| WO | 2010115843 | A2 | 10/2010 |
| WO | 2010115843 | A3 | 12/2010 |
| WO | 2010142423 | A2 | 12/2010 |
| WO | 2010144711 | A2 | 12/2010 |
| WO | 2011016238 | A1 | 2/2011 |
| WO | 2010142423 | A3 | 5/2011 |
| WO | 2011133919 | A1 | 10/2011 |
| WO | 2012045882 | A2 | 4/2012 |
| WO | 2012045882 | A3 | 5/2012 |
| WO | 2013096380 | A2 | 6/2013 |
| WO | 2013096380 | A3 | 8/2013 |
| WO | 2013180238 | A1 | 12/2013 |
| WO | 2014028777 | A2 | 2/2014 |
| WO | 2014100600 | A2 | 6/2014 |
| WO | 2014100600 | A3 | 8/2014 |
| WO | 2015200806 | A2 | 12/2015 |
| WO | 2015200806 | A3 | 2/2016 |
| WO | 2016112078 | A2 | 7/2016 |
| WO | 2016112078 | A3 | 9/2016 |
| WO | 2017005732 | A1 | 1/2017 |
| WO | 2017005734 | A1 | 1/2017 |
| WO | 2017009308 | A2 | 1/2017 |
| WO | 2017009308 | A3 | 4/2017 |
| WO | 2018154390 | A1 | 8/2018 |

OTHER PUBLICATIONS

International Search Report and Written Opinion dated Jun. 7, 2018 of International Patent Application No. PCT/IB2018/000249 (published as WO 2018154390) (3 pages).

Mendez et al., Functional Transplant of Megabase Human Immunoglobulin loci Recapitulates Human Antibody Response in Mice, Nature Genetics, 1997, pp. 146-156, 15.

Noble, Wendy et al., Advances in tau-based drug discovery, Expert Opinion on Drug Discovery, 2011, 797-810, 6:8.

Umeda, Tomohiro et al., Passive immunotherapy of tauopathy targeting pSer413-tau: a pilot study in mice, Annals of Clinical and Translational Neurology, 2015, 1-15, N/A.

Wen et al., Polyethylene glycol conjugated anti EGF receptor antibody C225 with radiometal chelator attached to teh termini of polymer chains, Bioconj. Chem., 2001, pp. 545-553, 12.

Boutajangout, Allal et al., Immunotherapy argeting Pathological Tau Prevents Cognitive Decline in a New Tangle Mouse Model, Journal of Neuroscience, 2010, 16559-16566, 30(49).

Boutajangout, Allal et al., Passive immunization targeting pathological phospho-tau protein in a mouse model reduces functional decline and clears tau aggregates from the brain, Journal of Neurochemistry, 2011, 658-667, 118(4).

PCT, International Search Report, PCT, dated Jul. 13, 2013, pp. 1-2 PCT/JP2013/065090, —.

PCT, International Search Report, PCT, dated Oct. 5, 2021, p. 1-6 PCT/US2021/038591, —.

Wisniewski, Thomas et al., Murine models of Alzheimer's disease and their use in developing immunotherapies, Biochimica et Biophysica Acta, Molecular Basis of Disease, 2010, 847-859, 1802(10).

Written Opinion received for 24996 application No. PCT/US2021/038591—dated Oct. 5, 2021, p. 6.

Xiyun Chai, et al., Passive Immunization with Anti-Tau Antibodies in Two Transgenic Models, The Journal of Biological Chemistry, 2011, 34457-34467, vol. 286, No. 39.

SEQUENCE LISTING

<160> NUMBER OF SEQ ID NOS: 109

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

-continued

```
Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 412
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
            85                  90                  95
```

-continued

```
Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```

<210> SEQ ID NO 3
<211> LENGTH: 383
<212> TYPE: PRT
<213> ORGANISM: Homo sapiens

<400> SEQUENCE: 3

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45
```

-continued

Gly Ile Gly Asp Thr Pro Ser Leu Glu Asp Glu Ala Ala Gly His Val
            50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
    195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
    275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
    355                 360                 365

Thr Leu Ala Asp Glu Val Ser Ala Ser Leu Ala Lys Gln Gly Leu
    370                 375                 380

<210> SEQ ID NO 4
<211> LENGTH: 410
<212> TYPE: PRT
<213> ORGANISM: Homo sapiens

<400> SEQUENCE: 4

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

```
Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Lys Ser Gly
            180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
                305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
        340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 5
<211> LENGTH: 381
<212> TYPE: PRT
<213> ORGANISM: Homo sapiens
```

<400> SEQUENCE: 5

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380
```

<210> SEQ ID NO 6
<211> LENGTH: 350
<212> TYPE: PRT
<213> ORGANISM: Homo sapiens

<400> SEQUENCE: 6

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln
            340                 345                 350
```

<210> SEQ ID NO 7
<211> LENGTH: 16
<212> TYPE: PRT
<213> ORGANISM: Artificial Sequence
<220> FEATURE:
<223> OTHER INFORMATION: Ta1505, VL-CDR1

<400> SEQUENCE: 7

Arg Ser Ser Gln Asn Ile Val His Ser Asn Gly Asn Thr Tyr Leu Glu
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Ta1505, VL-CDR2

<400> SEQUENCE: 8

Thr Val Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Ta1505, VL-CDR3

<400> SEQUENCE: 9

Phe Gln Gly Ser His Leu Pro Leu Thr
1               5

<210> SEQ ID NO 10
<211> LENGTH: 112
<212> TYPE: PRT
<213> ORGANISM: Artificial Sequence
<220> FEATURE:
<223> OTHER INFORMATION: Ta1505, VL

<400> SEQUENCE: 10

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Leu Glu Leu Lys
            100                 105                 110

<210> SEQ ID NO 11
<211> LENGTH: 219
<212> TYPE: PRT
<213> ORGANISM: Artificial Sequence
<220> FEATURE:
<223> OTHER INFORMATION: Ta1505, light chain

<400> SEQUENCE: 11

Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Leu Pro Leu Thr Phe Gly Gly Gly Thr Lys Leu Glu Leu Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
        210                 215

<210> SEQ ID NO 12
<211> LENGTH: 5
<212> TYPE: PRT
<213> ORGANISM: Artificial Sequence
<220> FEATURE:
<223> OTHER INFORMATION: SFALN

<400> SEQUENCE: 12

Ser Phe Ala Leu Asn
1               5

<210> SEQ ID NO 13
<211> LENGTH: 19
<212> TYPE: PRT
<213> ORGANISM: Artificial Sequence
<220> FEATURE:
<223> OTHER INFORMATION: Ta1505, VH-CDR2

<400> SEQUENCE: 13

His Ile Arg Ser Lys Thr Asn Asn Tyr Ala Thr Phe Tyr Ala Asp Ser
1               5                   10                  15

Val Lys Asp

<210> SEQ ID NO 14
<211> LENGTH: 10
<212> TYPE: PRT
<213> ORGANISM: Artificial Sequence
<220> FEATURE:
<223> OTHER INFORMATION: Ta1505, VH-CDR3

<400> SEQUENCE: 14

Arg Gly Pro Arg Asp Ser Trp Phe Gly Tyr
1               5                   10

<210> SEQ ID NO 15

<211> LENGTH: 121
<212> TYPE: PRT
<213> ORGANISM: Artificial Sequence
<220> FEATURE:
<223> OTHER INFORMATION: Ta1505, VH

<400> SEQUENCE: 15

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ala Phe Asn Ser Phe
            20                  25                  30

Ala Leu Asn Trp Val Arg Gln Ala Pro Gly Lys Ser Leu Glu Trp Val
        35                  40                  45

Val His Ile Arg Ser Lys Thr Asn Asn Tyr Ala Thr Phe Tyr Ala Asp
    50                  55                  60

Ser Val Lys Asp Arg Phe Thr Val Ser Arg Asp Asp Ser Gln Ser Met
65                  70                  75                  80

Val Tyr Leu Gln Met Asn Asn Leu Lys Thr Glu Asp Thr Gly Ile Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ala
        115                 120

<210> SEQ ID NO 16
<211> LENGTH: 451
<212> TYPE: PRT
<213> ORGANISM: Artificial Sequence
<220> FEATURE:
<223> OTHER INFORMATION: Ta1505, heavy chain

<400> SEQUENCE: 16

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ala Phe Asn Ser Phe
            20                  25                  30

Ala Leu Asn Trp Val Arg Gln Ala Pro Gly Lys Ser Leu Glu Trp Val
        35                  40                  45

Val His Ile Arg Ser Lys Thr Asn Asn Tyr Ala Thr Phe Tyr Ala Asp
    50                  55                  60

Ser Val Lys Asp Arg Phe Thr Val Ser Arg Asp Asp Ser Gln Ser Met
65                  70                  75                  80

Val Tyr Leu Gln Met Asn Asn Leu Lys Thr Glu Asp Thr Gly Ile Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ala Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

```
Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
                260                 265                 270

Asp Asp Pro Asp Val Gln Ile Ser Trp Phe Val Asn Asn Val Glu Val
                275                 280                 285

His Thr Ala Gln Thr Gln Thr His Arg Glu Asp Tyr Asn Ser Thr Leu
        290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Glu Glu Glu Met Thr Lys Lys Gln Val Thr
                355                 360                 365

Leu Thr Cys Met Val Thr Asp Phe Met Pro Glu Asp Ile Tyr Val Glu
        370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
        435                 440                 445

Pro Gly Lys
    450

<210> SEQ ID NO 17
<211> LENGTH: 16
<212> TYPE: PRT
<213> ORGANISM: Artificial Sequence
<220> FEATURE:
<223> OTHER INFORMATION: VL46, VL-CDR1

<400> SEQUENCE: 17

Arg Ser Ser Gln Ser Ile Val His Ser Asn Gly Asn Thr Tyr Leu Glu
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: VL46, VL-CDR2

<400> SEQUENCE: 18

Thr Val Ser Asn Arg Phe Ser
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: VL46, VL-CDR3

<400> SEQUENCE: 19

Phe Gln Gly Ser His Leu Pro Leu Thr
1               5

<210> SEQ ID NO 20
<211> LENGTH: 112
<212> TYPE: PRT
<213> ORGANISM: Artificial Sequence
<220> FEATURE:
<223> OTHER INFORMATION: VL46, VL

<400> SEQUENCE: 20

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

<210> SEQ ID NO 21
<211> LENGTH: 5
<212> TYPE: PRT
<213> ORGANISM: Artificial Sequence
<220> FEATURE:
<223> OTHER INFORMATION: VH11, VH-CDR1

<400> SEQUENCE: 21

Ser Phe Ala Leu Asn
1               5

<210> SEQ ID NO 22
<211> LENGTH: 19
<212> TYPE: PRT
<213> ORGANISM: Artificial Sequence
<220> FEATURE:
<223> OTHER INFORMATION: VH11, VH-CDR2

<400> SEQUENCE: 22

His Ile Arg Ser Lys Thr Asn Asn Tyr Ala Thr Phe Tyr Ala Ala Ser
1               5                   10                  15

Val Lys Asp

<210> SEQ ID NO 23
<211> LENGTH: 10
<212> TYPE: PRT
<213> ORGANISM: Artificial Sequence
<220> FEATURE:
<223> OTHER INFORMATION: VH11, VH-CDR3
```

```
<400> SEQUENCE: 23

Arg Gly Pro Arg Asp Ser Trp Phe Gly Tyr
1               5                   10

<210> SEQ ID NO 24
<211> LENGTH: 121
<212> TYPE: PRT
<213> ORGANISM: Artificial Sequence
<220> FEATURE:
<223> OTHER INFORMATION: VH11, VH

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 25
<211> LENGTH: 16
<212> TYPE: PRT
<213> ORGANISM: Artificial Sequence
<220> FEATURE:
<223> OTHER INFORMATION: VL46_G34A_S28N, VL-CDR1

<400> SEQUENCE: 25

Arg Ser Ser Gln Asn Ile Val His Ser Asn Ala Asn Thr Tyr Leu Glu
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: VL46_G34A_S28N, VL-CDR2

<400> SEQUENCE: 26

Thr Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: VL46_G34A_S28N, VL-CDR3

<400> SEQUENCE: 27

Phe Gln Gly Ser His Leu Pro Leu Thr
1               5
```

<210> SEQ ID NO 28
<211> LENGTH: 112
<212> TYPE: PRT
<213> ORGANISM: Artificial Sequence
<220> FEATURE:
<223> OTHER INFORMATION: VL46_G34A_S28N, VL

<400> SEQUENCE: 28

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Asn Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110
```

<210> SEQ ID NO 29
<211> LENGTH: 16
<212> TYPE: PRT
<213> ORGANISM: Artificial Sequence
<220> FEATURE:
<223> OTHER INFORMATION: VL46_G34A_S28N_Q27R_S32R_H98Y, VL-CDR1

<400> SEQUENCE: 29

```
Arg Ser Ser Arg Asn Ile Val His Arg Asn Ala Asn Thr Tyr Leu Glu
1               5                   10                  15
```

<210> SEQ ID NO 30
<211> LENGTH: 7
<212> TYPE: PRT
<213> ORGANISM: Artificial Sequence
<220> FEATURE:
<223> OTHER INFORMATION: VL46_G34A_S28N_Q27R_S32R_H98Y, VL-CDR2

<400> SEQUENCE: 30

```
Thr Val Ser Asn Arg Phe Ser
1               5
```

<210> SEQ ID NO 31
<211> LENGTH: 9
<212> TYPE: PRT
<213> ORGANISM: Artificial Sequence
<220> FEATURE:
<223> OTHER INFORMATION: VL46_G34A_S28N_Q27R_S32R_H98Y, VL-CDR3

<400> SEQUENCE: 31

```
Phe Gln Gly Ser Tyr Leu Pro Leu Thr
1               5
```

<210> SEQ ID NO 32
<211> LENGTH: 112
<212> TYPE: PRT
<213> ORGANISM: Artificial Sequence
<220> FEATURE:
<223> OTHER INFORMATION: VL46_G34A_S28N_Q27R_S32R_H98Y, VL

<400> SEQUENCE: 32

Asp Ile Val Met Thr Gln Ser Pro Leu Ser Leu Pro Val Thr Leu Gly
1               5                   10                  15

Glu Pro Ala Ser Ile Ser Cys Arg Ser Ser Arg Asn Ile Val His Arg
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Leu Pro Leu Thr Phe Gly Gly Gly Thr Lys Val Glu Ile Lys
            100                 105                 110

<210> SEQ ID NO 33
<211> LENGTH: 16
<212> TYPE: PRT
<213> ORGANISM: Artificial Sequence
<220> FEATURE:
<223> OTHER INFORMATION: VL46_G34A_S28K_S32R_H98Y, VL-CDR1

<400> SEQUENCE: 33

Arg Ser Ser Gln Lys Ile Val His Arg Asn Ala Asn Thr Tyr Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: VL46_G34A_S28K_S32R_H98Y, VL-CDR2

<400> SEQUENCE: 34

Thr Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: VL46_G34A_S28K_S32R_H98Y, VL-CDR3

<400> SEQUENCE: 35

Phe Gln Gly Ser Tyr Leu Pro Leu Thr
1               5

<210> SEQ ID NO 36
<211> LENGTH: 112
<212> TYPE: PRT
<213> ORGANISM: Artificial Sequence
<220> FEATURE:
<223> OTHER INFORMATION: VL46_G34A_S28K_S32R_H98Y, VL

<400> SEQUENCE: 36

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Lys Ile Val His Arg
            20                  25                  30

```
Asn Ala Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Tyr Leu Pro Leu Thr Phe Gly Gly Gly Thr Lys Val Glu Ile Lys
                100                 105                 110
```

<210> SEQ ID NO 37
<211> LENGTH: 16
<212> TYPE: PRT
<213> ORGANISM: Artificial Sequence
<220> FEATURE:
<223> OTHER INFORMATION: VL46_G34A_S28N_Q27H_S32R_H98Y, VL-CDR1

<400> SEQUENCE: 37

```
Arg Ser Ser His Asn Ile Val His Arg Asn Ala Asn Thr Tyr Leu Glu
 1               5                   10                  15
```

<210> SEQ ID NO 38
<211> LENGTH: 7
<212> TYPE: PRT
<213> ORGANISM: Artificial Sequence
<220> FEATURE:
<223> OTHER INFORMATION: VL46_G34A_S28N_Q27H_S32R_H98Y, VL-CDR2

<400> SEQUENCE: 38

```
Thr Val Ser Asn Arg Phe Ser
 1               5
```

<210> SEQ ID NO 39
<211> LENGTH: 9
<212> TYPE: PRT
<213> ORGANISM: Artificial Sequence
<220> FEATURE:
<223> OTHER INFORMATION: VL46_G34A_S28N_Q27H_S32R_H98Y, VL-CDR3

<400> SEQUENCE: 39

```
Phe Gln Gly Ser Tyr Leu Pro Leu Thr
 1               5
```

<210> SEQ ID NO 40
<211> LENGTH: 112
<212> TYPE: PRT
<213> ORGANISM: Artificial Sequence
<220> FEATURE:
<223> OTHER INFORMATION: VL46_G34A_S28N_Q27H_S32R_H98Y, VL

<400> SEQUENCE: 40

```
Asp Ile Val Met Thr Gln Ser Pro Leu Ser Leu Pro Val Thr Leu Gly
 1               5                   10                  15

Glu Pro Ala Ser Ile Ser Cys Arg Ser Ser His Asn Ile Val His Arg
                 20                  25                  30

Asn Ala Asn Thr Tyr Leu Glu Trp Tyr Leu Gln Lys Pro Gly Gln Ser
            35                  40                  45

Pro Gln Leu Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Tyr Cys Phe Gln Gly
                85                  90                  95

Ser Tyr Leu Pro Leu Thr Phe Gly Gly Gly Thr Lys Val Glu Ile Lys
            100                 105                 110

<210> SEQ ID NO 41
<211> LENGTH: 5
<212> TYPE: PRT
<213> ORGANISM: Artificial Sequence
<220> FEATURE:
<223> OTHER INFORMATION: VH11_D68G, VH-CDR1

<400> SEQUENCE: 41

Ser Phe Ala Leu Asn
1               5

<210> SEQ ID NO 42
<211> LENGTH: 19
<212> TYPE: PRT
<213> ORGANISM: Artificial Sequence
<220> FEATURE:
<223> OTHER INFORMATION: VH11_D68G, VH-CDR2

<400> SEQUENCE: 42

His Ile Arg Ser Lys Thr Asn Asn Tyr Ala Thr Phe Tyr Ala Ala Ser
1               5                   10                  15

Val Lys Gly

<210> SEQ ID NO 43
<211> LENGTH: 10
<212> TYPE: PRT
<213> ORGANISM: Artificial Sequence
<220> FEATURE:
<223> OTHER INFORMATION: VH11_D68G, VH-CDR3

<400> SEQUENCE: 43

Arg Gly Pro Arg Asp Ser Trp Phe Gly Tyr
1               5                   10

<210> SEQ ID NO 44
<211> LENGTH: 121
<212> TYPE: PRT
<213> ORGANISM: Artificial Sequence
<220> FEATURE:
<223> OTHER INFORMATION: VH11_D68G, VH

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95
```

```
Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 45
<211> LENGTH: 5
<212> TYPE: PRT
<213> ORGANISM: Artificial Sequence
<220> FEATURE:
<223> OTHER INFORMATION: VH11_A59V_D68G, VH-CDR1

<400> SEQUENCE: 45

Ser Phe Ala Leu Asn
1               5

<210> SEQ ID NO 46
<211> LENGTH: 19
<212> TYPE: PRT
<213> ORGANISM: Artificial Sequence
<220> FEATURE:
<223> OTHER INFORMATION: VH11_A59V_D68G, VH-CDR2

<400> SEQUENCE: 46

His Ile Arg Ser Lys Thr Asn Asn Tyr Val Thr Phe Tyr Ala Ala Ser
1               5                   10                  15

Val Lys Gly

<210> SEQ ID NO 47
<211> LENGTH: 10
<212> TYPE: PRT
<213> ORGANISM: Artificial Sequence
<220> FEATURE:
<223> OTHER INFORMATION: VH11_A59V_D68G, VH-CDR3

<400> SEQUENCE: 47

Arg Gly Pro Arg Asp Ser Trp Phe Gly Tyr
1               5                   10

<210> SEQ ID NO 48
<211> LENGTH: 121
<212> TYPE: PRT
<213> ORGANISM: Artificial Sequence
<220> FEATURE:
<223> OTHER INFORMATION: VH11_A59V_D68G, VH

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Val Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110
```

Gln Gly Thr Leu Val Thr Val Ser Ser
        115                 120

<210> SEQ ID NO 49
<211> LENGTH: 5
<212> TYPE: PRT
<213> ORGANISM: Artificial Sequence
<220> FEATURE:
<223> OTHER INFORMATION: VH11_K54E_D68G, VH-CDR1

<400> SEQUENCE: 49

Ser Phe Ala Leu Asn
1               5

<210> SEQ ID NO 50
<211> LENGTH: 19
<212> TYPE: PRT
<213> ORGANISM: Artificial Sequence
<220> FEATURE:
<223> OTHER INFORMATION: VH11_K54E_D68G, VH-CDR2

<400> SEQUENCE: 50

His Ile Arg Ser Glu Thr Asn Asn Tyr Ala Thr Phe Tyr Ala Ala Ser
1               5                   10                  15

Val Lys Gly

<210> SEQ ID NO 51
<211> LENGTH: 10
<212> TYPE: PRT
<213> ORGANISM: Artificial Sequence
<220> FEATURE:
<223> OTHER INFORMATION: VH11_K54E_D68G, VH-CDR3

<400> SEQUENCE: 51

Arg Gly Pro Arg Asp Ser Trp Phe Gly Tyr
1               5                   10

<210> SEQ ID NO 52
<211> LENGTH: 121
<212> TYPE: PRT
<213> ORGANISM: Artificial Sequence
<220> FEATURE:
<223> OTHER INFORMATION: VH11_K54E_D68G, VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Glu Thr Asn Asn Tyr Ala Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 53
<211> LENGTH: 5
<212> TYPE: PRT
<213> ORGANISM: Artificial Sequence
<220> FEATURE:
<223> OTHER INFORMATION: VH11_K54E_A59V_D68G, VH-CDR1

<400> SEQUENCE: 53

Ser Phe Ala Leu Asn
1               5

<210> SEQ ID NO 54
<211> LENGTH: 19
<212> TYPE: PRT
<213> ORGANISM: Artificial Sequence
<220> FEATURE:
<223> OTHER INFORMATION: VH11_K54E_A59V_D68G, VH-CDR2

<400> SEQUENCE: 54

His Ile Arg Ser Glu Thr Asn Asn Tyr Val Thr Phe Tyr Ala Ala Ser
1               5                   10                  15

Val Lys Gly

<210> SEQ ID NO 55
<211> LENGTH: 10
<212> TYPE: PRT
<213> ORGANISM: Artificial Sequence
<220> FEATURE:
<223> OTHER INFORMATION: VH11_K54E_A59V_D68G, VH-CDR3

<400> SEQUENCE: 55

Arg Gly Pro Arg Asp Ser Trp Phe Gly Tyr
1               5                   10

<210> SEQ ID NO 56
<211> LENGTH: 121
<212> TYPE: PRT
<213> ORGANISM: Artificial Sequence
<220> FEATURE:
<223> OTHER INFORMATION: VH11_K54E_A59V_D68G, VH

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Glu Thr Asn Asn Tyr Val Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser
        115                 120

<210> SEQ ID NO 57
<211> LENGTH: 106
<212> TYPE: PRT
<213> ORGANISM: Homo sapiens

<400> SEQUENCE: 57

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 58
<211> LENGTH: 107
<212> TYPE: PRT
<213> ORGANISM: Homo sapiens

<400> SEQUENCE: 58

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 59
<211> LENGTH: 330
<212> TYPE: PRT
<213> ORGANISM: Homo sapiens

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 60
<211> LENGTH: 330
<212> TYPE: PRT
<213> ORGANISM: Artificial Sequence
<220> FEATURE:
<223> OTHER INFORMATION: Human_IgG1_LALA, constant region

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 61
<211> LENGTH: 330
<212> TYPE: PRT
<213> ORGANISM: Artificial Sequence
<220> FEATURE:
<223> OTHER INFORMATION: Human_IgG1_ LALA_D265S, constant region

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 62
<211> LENGTH: 330
<212> TYPE: PRT
<213> ORGANISM: Artificial Sequence
<220> FEATURE:
<223> OTHER INFORMATION: Human_IgG1_YTE, constant region

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 63
<211> LENGTH: 330
<212> TYPE: PRT
<213> ORGANISM: Artificial Sequence
<220> FEATURE:
<223> OTHER INFORMATION: Human_IgG1_LALA_YTE, constant region

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 64
<211> LENGTH: 330
<212> TYPE: PRT
<213> ORGANISM: Artificial Sequence
<220> FEATURE:
<223> OTHER INFORMATION: Human_IgG1_N297A, constant region

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 330
<212> TYPE: PRT
<213> ORGANISM: Artificial Sequence
<220> FEATURE:
<223> OTHER INFORMATION: Human_IgG1_N297Q, constant region

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 326
<212> TYPE: PRT
<213> ORGANISM: Homo sapiens

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 67
<211> LENGTH: 327
<212> TYPE: PRT
<213> ORGANISM: Homo sapiens

<400> SEQUENCE: 67

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 68
<211> LENGTH: 327
<212> TYPE: PRT
<213> ORGANISM: Artificial Sequence
<220> FEATURE:
<223> OTHER INFORMATION: Human_IgG4_S228P, constant region

<400> SEQUENCE: 68

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 69
<211> LENGTH: 219
<212> TYPE: PRT
<213> ORGANISM: Artificial Sequence
<220> FEATURE:
<223> OTHER INFORMATION: VL46_G34A_S28N_kappa light chain

<400> SEQUENCE: 69

```
Asp Ile Val Met Thr Gln Ser Pro Leu Ser Leu Pro Val Thr Leu Gly
1               5                   10                  15
```

Glu Pro Ala Ser Ile Ser Cys Arg Ser Ser Gln Asn Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 70
<211> LENGTH: 448
<212> TYPE: PRT
<213> ORGANISM: Artificial Sequence
<220> FEATURE:
<223> OTHER INFORMATION: VH11_IgG4-S228P heavy chain

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Lys Thr Asn Asn Tyr Ala Thr Phe Tyr Ala Ala
    50                  55                  60

Ser Val Lys Asp Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
        180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 71
<211> LENGTH: 219
<212> TYPE: PRT
<213> ORGANISM: Artificial Sequence
<220> FEATURE:
<223> OTHER INFORMATION: V8-AFM-hIgG1 LALA, light chain

<400> SEQUENCE: 71

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Lys Ile Val His Arg
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Leu Gly Val Tyr Tyr Cys Phe Gln Gly
                85                  90                  95

Ser Tyr Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 72
<211> LENGTH: 451
<212> TYPE: PRT
<213> ORGANISM: Artificial Sequence
<220> FEATURE:
<223> OTHER INFORMATION: V8-AFM-hIgG1 LALA, heavy chain

<400> SEQUENCE: 72

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Glu Thr Asn Asn Tyr Val Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

-continued

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 73
<211> LENGTH: 219
<212> TYPE: PRT
<213> ORGANISM: Artificial Sequence
<220> FEATURE:
<223> OTHER INFORMATION: V8-AFM-hIgG1 LALA YTE, light chain

<400> SEQUENCE: 73

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Lys Ile Val His Arg
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 74
<211> LENGTH: 451
<212> TYPE: PRT
<213> ORGANISM: Artificial Sequence
<220> FEATURE:
<223> OTHER INFORMATION: V8-AFM-hIgG1 LALA YTE, heavy chain

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Glu Thr Asn Asn Tyr Val Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

-continued

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 75
<211> LENGTH: 219
<212> TYPE: PRT
<213> ORGANISM: Artificial Sequence
<220> FEATURE:
<223> OTHER INFORMATION: V8-AFM-hIgG1 LALA YTE, heavy chain

<400> SEQUENCE: 75

Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Lys Ile Val His Arg
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 76
<211> LENGTH: 448
<212> TYPE: PRT
<213> ORGANISM: Artificial Sequence
<220> FEATURE:
<223> OTHER INFORMATION: V8-AFM-hIgG4, light chain

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Leu Asn Trp Val Arg Gln Ala Pro Gly Lys Gly Leu Glu Trp Val
        35                  40                  45

Gly His Ile Arg Ser Glu Thr Asn Asn Tyr Val Thr Phe Tyr Ala Ala
    50                  55                  60

Ser Val Lys Gly Arg Phe Thr Val Ser Arg Asp Asp Ser Gln Asn Thr
65                  70                  75                  80

Ala Tyr Leu Gln Met Asn Ser Leu Lys Thr Glu Asp Thr Ala Thr Tyr
                85                  90                  95

Tyr Cys Val Arg Arg Gly Pro Arg Asp Ser Trp Phe Gly Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
                435                 440                 445

<210> SEQ ID NO 77
<211> LENGTH: 17
<212> TYPE: PRT
<213> ORGANISM: Artificial Sequence
<220> FEATURE:
<223> OTHER INFORMATION: PD17(P)
<220> FEATURE:
<221> NAME/KEY: MISC_FEATURE
<222> LOCATION: (9)..(9)
<223> OTHER INFORMATION: s=phosphorylated

<400> SEQUENCE: 77

Pro Arg His Leu Ser Asn Val Ser Ser Thr Gly Ser Ile Asp Met Val
1               5                   10                  15

Asp

<210> SEQ ID NO 78
<211> LENGTH: 17
<212> TYPE: PRT
<213> ORGANISM: Artificial Sequence
<220> FEATURE:
<223> OTHER INFORMATION: PD17

<400> SEQUENCE: 78

Pro Arg His Leu Ser Asn Val Ser Ser Thr Gly Ser Ile Asp Met Val
1               5                   10                  15

Asp

<210> SEQ ID NO 79
<211> LENGTH: 32
<212> TYPE: PRT
<213> ORGANISM: Artificial Sequence
<220> FEATURE:
<223> OTHER INFORMATION: T-pS396/400/404GC
<220> FEATURE:
<221> NAME/KEY: MISC_FEATURE
<222> LOCATION: (20)..(20)
<223> OTHER INFORMATION: S=phosphorylated
<220> FEATURE:
<221> NAME/KEY: MISC_FEATURE
<222> LOCATION: (24)..(24)
<223> OTHER INFORMATION: S=phosphorylated
<220> FEATURE:
<221> NAME/KEY: MISC_FEATURE
<222> LOCATION: (28)..(28)
<223> OTHER INFORMATION: S=phosphorylated
```

```
<400> SEQUENCE: 79

Gly Cys Arg Glu Asn Ala Lys Ala Lys Thr Asp His Gly Ala Glu Ile
1               5                   10                  15

Val Tyr Lys Ser Pro Val Val Ser Gly Asp Thr Ser Pro Arg His Leu
            20                  25                  30

<210> SEQ ID NO 80
<211> LENGTH: 26
<212> TYPE: PRT
<213> ORGANISM: Artificial Sequence
<220> FEATURE:
<223> OTHER INFORMATION: T-pT212pS214GC
<220> FEATURE:
<221> NAME/KEY: MISC_FEATURE
<222> LOCATION: (14)..(14)
<223> OTHER INFORMATION: T=phosphorylated
<220> FEATURE:
<221> NAME/KEY: MISC_FEATURE
<222> LOCATION: (16)..(16)
<223> OTHER INFORMATION: S=phosphorylated

<400> SEQUENCE: 80

Gly Cys Gly Ser Pro Gly Thr Pro Gly Ser Arg Ser Arg Thr Pro Ser
1               5                   10                  15

Leu Pro Thr Pro Pro Thr Arg Glu Pro Lys
            20                  25

<210> SEQ ID NO 81
<211> LENGTH: 8
<212> TYPE: PRT
<213> ORGANISM: Artificial Sequence
<220> FEATURE:
<223> OTHER INFORMATION: pSer412Cys
<220> FEATURE:
<221> NAME/KEY: MISC_FEATURE
<222> LOCATION: (3)..(3)
<223> OTHER INFORMATION: S=phosphorylated

<400> SEQUENCE: 81

Asn Val Ser Ser Thr Gly Ser Cys
1               5

<210> SEQ ID NO 82
<211> LENGTH: 25
<212> TYPE: PRT
<213> ORGANISM: Artificial Sequence
<220> FEATURE:
<223> OTHER INFORMATION: T-pT217GC
<220> FEATURE:
<221> NAME/KEY: MISC_FEATURE
<222> LOCATION: (13)..(13)
<223> OTHER INFORMATION: T=phosphorylated

<400> SEQUENCE: 82

Gly Cys Gly Ser Arg Ser Arg Thr Pro Ser Leu Pro Thr Pro Pro Thr
1               5                   10                  15

Arg Glu Pro Lys Lys Val Ala Val Val
            20                  25

<210> SEQ ID NO 83
<211> LENGTH: 16
<212> TYPE: PRT
<213> ORGANISM: Artificial Sequence
<220> FEATURE:
<223> OTHER INFORMATION: VL-CDR1, AbM
```

```
<400> SEQUENCE: 83

Arg Ser Ser Gln Lys Ile Val His Arg Asn Ala Asn Thr Tyr Leu Glu
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: VL-CDR2, AbM

<400> SEQUENCE: 84

Thr Val Ser Asn Arg Phe Ser
1               5

<210> SEQ ID NO 85
<211> LENGTH: 9
<212> TYPE: PRT
<213> ORGANISM: Artificial Sequence
<220> FEATURE:
<223> OTHER INFORMATION: VL-CDR3, AbM

<400> SEQUENCE: 85

Phe Gln Gly Ser Tyr Leu Pro Leu Thr
1               5

<210> SEQ ID NO 86
<211> LENGTH: 10
<212> TYPE: PRT
<213> ORGANISM: Artificial Sequence
<220> FEATURE:
<223> OTHER INFORMATION: VH-CDR1, AbM

<400> SEQUENCE: 86

Gly Phe Thr Phe Ser Ser Phe Ala Leu Asn
1               5                   10

<210> SEQ ID NO 87
<211> LENGTH: 12
<212> TYPE: PRT
<213> ORGANISM: Artificial Sequence
<220> FEATURE:
<223> OTHER INFORMATION: VH-CDR2, AbM

<400> SEQUENCE: 87

His Ile Arg Ser Glu Thr Asn Asn Tyr Val Thr Phe
1               5                   10

<210> SEQ ID NO 88
<211> LENGTH: 10
<212> TYPE: PRT
<213> ORGANISM: Artificial Sequence
<220> FEATURE:
<223> OTHER INFORMATION: VL-CDR1, Chothia

<400> SEQUENCE: 88

Arg Gly Pro Arg Asp Ser Trp Phe Gly Tyr
1               5                   10

<210> SEQ ID NO 89
<211> LENGTH: 16
<212> TYPE: PRT
<213> ORGANISM: Artificial Sequence
<220> FEATURE:
<223> OTHER INFORMATION: VL-CDR1, Chothia
```

<400> SEQUENCE: 89

Arg Ser Gln Lys Ile Val His Arg Asn Ala Asn Thr Tyr Leu Glu
1               5                   10                  15

<210> SEQ ID NO 90
<211> LENGTH: 7
<212> TYPE: PRT
<213> ORGANISM: Artificial Sequence
<220> FEATURE:
<223> OTHER INFORMATION: VL-CDR2, Chothia

<400> SEQUENCE: 90

Thr Val Ser Asn Arg Phe Ser
1               5

<210> SEQ ID NO 91
<211> LENGTH: 9
<212> TYPE: PRT
<213> ORGANISM: Artificial Sequence
<220> FEATURE:
<223> OTHER INFORMATION: VL-CDR3, Chothia

<400> SEQUENCE: 91

Phe Gln Gly Ser Tyr Leu Pro Leu Thr
1               5

<210> SEQ ID NO 92
<211> LENGTH: 7
<212> TYPE: PRT
<213> ORGANISM: Artificial Sequence
<220> FEATURE:
<223> OTHER INFORMATION: VH-CDR1, Chothia

<400> SEQUENCE: 92

Gly Phe Thr Phe Ser Ser Phe
1               5

<210> SEQ ID NO 93
<211> LENGTH: 8
<212> TYPE: PRT
<213> ORGANISM: Artificial Sequence
<220> FEATURE:
<223> OTHER INFORMATION: VH-CDR2, Chothia

<400> SEQUENCE: 93

Arg Ser Glu Thr Asn Asn Tyr Val
1               5

<210> SEQ ID NO 94
<211> LENGTH: 10
<212> TYPE: PRT
<213> ORGANISM: Artificial Sequence
<220> FEATURE:
<223> OTHER INFORMATION: VH-CDR3, Chothia

<400> SEQUENCE: 94

Arg Gly Pro Arg Asp Ser Trp Phe Gly Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: VL-CDR1, Contact

<400> SEQUENCE: 95

Val His Arg Asn Ala Asn Thr Tyr Leu Glu Trp Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: VL-CDR2, Contact

<400> SEQUENCE: 96

Leu Leu Ile Tyr Thr Val Ser Asn Arg Phe
1               5                   10

<210> SEQ ID NO 97
<211> LENGTH: 8
<212> TYPE: PRT
<213> ORGANISM: Artificial Sequence
<220> FEATURE:
<223> OTHER INFORMATION: VL-CDR3, Contact

<400> SEQUENCE: 97

Phe Gln Gly Ser Tyr Leu Pro Leu
1               5

<210> SEQ ID NO 98
<211> LENGTH: 6
<212> TYPE: PRT
<213> ORGANISM: Artificial Sequence
<220> FEATURE:
<223> OTHER INFORMATION: VH-CDR1, Contact

<400> SEQUENCE: 98

Ser Ser Phe Ala Leu Asn
1               5

<210> SEQ ID NO 99
<211> LENGTH: 15
<212> TYPE: PRT
<213> ORGANISM: Artificial Sequence
<220> FEATURE:
<223> OTHER INFORMATION: VH-CDR2, Contact

<400> SEQUENCE: 99

Trp Val Gly His Ile Arg Ser Glu Thr Asn Asn Tyr Val Thr Phe
1               5                   10                  15

<210> SEQ ID NO 100
<211> LENGTH: 11
<212> TYPE: PRT
<213> ORGANISM: Artificial Sequence
<220> FEATURE:
<223> OTHER INFORMATION: VH-CDR3, Contact

<400> SEQUENCE: 100

Val Arg Arg Gly Pro Arg Asp Ser Trp Phe Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: VL-CDR1, IMGT

```
<400> SEQUENCE: 101

Gln Lys Ile Val His Arg Asn Ala Asn Thr Tyr
1               5                   10

<210> SEQ ID NO 102
<211> LENGTH: 2
<212> TYPE: PRT
<213> ORGANISM: Artificial Sequence
<220> FEATURE:
<223> OTHER INFORMATION: VL-CDR2, IMGT

<400> SEQUENCE: 102

Thr Val
1

<210> SEQ ID NO 103
<211> LENGTH: 9
<212> TYPE: PRT
<213> ORGANISM: Artificial Sequence
<220> FEATURE:
<223> OTHER INFORMATION: VL-CDR3, IMGT

<400> SEQUENCE: 103

Phe Gln Gly Ser Tyr Leu Pro Leu Thr
1               5

<210> SEQ ID NO 104
<211> LENGTH: 8
<212> TYPE: PRT
<213> ORGANISM: Artificial Sequence
<220> FEATURE:
<223> OTHER INFORMATION: VH-CDR1, IMGT

<400> SEQUENCE: 104

Gly Phe Thr Phe Ser Ser Phe Ala
1               5

<210> SEQ ID NO 105
<211> LENGTH: 9
<212> TYPE: PRT
<213> ORGANISM: Artificial Sequence
<220> FEATURE:
<223> OTHER INFORMATION: VH-CDR2, IMGT

<400> SEQUENCE: 105

Ile Arg Ser Glu Thr Asn Asn Tyr Val
1               5

<210> SEQ ID NO 106
<211> LENGTH: 12
<212> TYPE: PRT
<213> ORGANISM: Artificial Sequence
<220> FEATURE:
<223> OTHER INFORMATION: VH-CDR3, IMGT

<400> SEQUENCE: 106

Val Arg Arg Gly Pro Arg Asp Ser Trp Phe Gly Tyr
1               5                   10

<210> SEQ ID NO 107
<211> LENGTH: 717
<212> TYPE: DNA
<213> ORGANISM: Artificial Sequence
<220> FEATURE:
<223> OTHER INFORMATION: DNA encoding light chain
```

<400> SEQUENCE: 107

```
atgtccgtgc ctacacaggt tctgggactg ctgctgctgt ggctgaccga cgccagatgc      60
gacatcgtga tgacccagtc tccactgagc ctgcctgtga cactgggaga gccagcctcc     120
atctcctgcc ggtcctctca gaaaatcgtg caccggaacg ccaacaccta cctggaatgg     180
tatctgcaga agcccggcca gtctcctcag ctgctgatct acaccgtgtc caaccggttc     240
tctggcgtgc ccgatagatt ctccggctct ggctctggca ccgacttcac cctgaagatc     300
tccagagtgg aagccgagga cctgggcgtg tactactgct ccaaggctc ctacctgcct      360
ctgacctttg gcggcggaac aaaggtggaa atcaagcgga cagtggccgc tccttccgtg     420
ttcatcttcc caccttccga cgagcagctg aagtccggca cagcttctgt cgtgtgcctg     480
ctgaacaact ctacccctcg ggaagccaag gtgcagtgga aggtggacaa tgccctgcag     540
tccggcaact cccaagagtc tgtgaccgag caggactcca aggacagcac ctacagcctg     600
tcctccacac tgaccctgtc caaggccgac tacgagaagc acaaggtgta cgcctgcgaa     660
gtgacccatc agggcctgtc tagccctgtg accaagtctt tcaaccgggg cgagtgt       717
```

<210> SEQ ID NO 108
<211> LENGTH: 1410
<212> TYPE: DNA
<213> ORGANISM: Artificial Sequence
<220> FEATURE:
<223> OTHER INFORMATION: DNA encoding heavy chain

<400> SEQUENCE: 108

```
atggaatggt cctgggtgtt cctgttcttc ctgtccgtga ccaccggcgt gcactctgaa      60
gtgcagctgg ttgaatctgg cggcggattg gttcagcctg gcggatctct gagactgtct     120
tgtgccgcct ccggcttcac cttctctagc ttcgctctga ctgggtccg acaggctcct      180
ggcaaaggac tggaatgggt cggacacatc agatccgaga caaacaacta cgtgaccttc     240
tacgccgcca gcgtgaaggg cagattcacc gtgtccagag atgactccca gaacaccgcc     300
tacctgcaga tgaactccct gaaaaccgag gacaccgcca ctactactg cgtgcgaaga     360
ggccctcggg acagttggtt cggatattgg ggacagggca cctcgtgac cgtgtcctct     420
gcttctacca agggacccag cgtgttccct ctggctcctt ccagcaagtc tacctctggc     480
ggaacagctg ctctgggctg cctggtcaag gactactttc ctgagcctgt gacagtgtcc     540
tggaactctg gcgctctgac atctggcgtg cacacctttc cagctgtgct gcagtcctcc     600
ggcctgtact ctctgtcctc tgtcgtgaca gtgccctcca gctctctggg aacccagacc     660
tacatctgca atgtgaacca caagccttcc aacaccaagg tggacaagaa ggtggaaccc     720
aagtcctgcg acaagaccca cacctgtcct ccatgtcctg ctccagaagc tgctggcggc     780
ccttccgtgt ttctgttccc tccaaagcct aaggacaccc tgtacatcac ccgcgagcct     840
gaagtgacct gcgtggtggt ggatgtgtct cacgaggacc ccgaagtgaa gttcaattgg     900
tacgtggacg gcgtggaagt gcacaacgcc aagaccaagc ctagagagga acagtacaac     960
tccacctaca gagtggtgtc cgtgctgacc gtgctgcacc aggattggct gaacggcaaa    1020
gagtacaagt gcaaggtgtc caacaaggcc ctgcctgctc ctatcgaaaa gaccatctcc    1080
aaggccaagg gccagcctag ggaacccag gtttacacct gcctccatc tcgggacgag      1140
ctgaccaaga accaggtgtc cctgacctgc ctcgtgaagg gattctaccc ctccgatatc    1200
gccgtggaat gggagtctaa tggccagcct gagaacaact acaagacaac ccctcctgtg    1260
```

```
ctggactccg acggctcatt ctttctgtac tccaagctga cagtggacaa gtccagatgg   1320
cagcagggca acgtgttctc ctgcagcgtg atgcacgagg ccctgcacaa tcactacacc   1380
cagaagtccc tgtctctgtc ccctggcaaa                                    1410

<210> SEQ ID NO 109
<211> LENGTH: 53
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: S=phosphorylated
<220> FEATURE:
<221> NAME/KEY: MISC_FEATURE
<222> LOCATION: (16)..(16)
<223> OTHER INFORMATION: S=phosphorylated
<220> FEATURE:
<221> NAME/KEY: MISC_FEATURE
<222> LOCATION: (25)..(25)
<223> OTHER INFORMATION: S=phosphorylated
<220> FEATURE:
<221> NAME/KEY: MISC_FEATURE
<222> LOCATION: (34)..(34)
<223> OTHER INFORMATION: S=phosphorylated

<400> SEQUENCE: 109

Gly Ala Glu Ile Val Tyr Lys Ser Pro Val Val Ser Gly Asp Thr Ser
1               5                   10                  15

Pro Arg His Leu Ser Asn Val Ser Ser Thr Gly Ser Ile Asp Met Val
            20                  25                  30

Asp Ser Pro Gln Leu Ala Thr Leu Ala Asp Glu Val Ser Ala Ser Leu
        35                  40                  45

Ala Lys Gln Gly Leu
    50
```

HIGH AFFINITY ANTIBODIES TARGETING TAU PHOSPHORYLATED AT SERINE 413

CROSS REFERENCE TO RELATED APPLICATIONS

This application claims the benefit of priority to U.S. Provisional Application No. 63/044,291, filed Jun. 25, 2020, the disclosure of which is incorporated by reference in its entirety.

FIELD

The present invention relates to high affinity antibodies or antigen binding fragments thereof that specifically bind to tau-pS413 (e.g., a human tau having the amino acid sequence of SEQ ID NO:1 that is phosphorylated at serine 413). The invention also relates to compositions, kits, methods, and uses involving the high affinity antibodies or antigen binding fragments disclosed herein.

BACKGROUND

Tau is a protein encoded by the MAPT gene, which is located on chromosome 17 (17q21) in the human genome. The tau protein is one of the microtubule-binding proteins abundantly expressed in the central nervous system. Tau has been found to be a major constituent protein in the paired helical filaments and straight filaments forming neurofibrillary tangles (NFT) in Alzheimer's disease (AD), one of the most prominent neurodegenerative diseases, and its intracellular accumulation has been demonstrated in a variety of neuropathological conditions. The diseases caused by such intracellular accumulation of tau are collectively referred to as "tauopathies" (Tetsuaki Arai, "Shinkei Naika" (Japanese document), Vol. 72, special number, (Suppl. 6), 2010, pp. 46-51). Tauopathies include neurodegenerative diseases such as AD, corticobasal degeneration (CBD) or corticobasal syndrome (CBS), progressive supranuclear palsy, Pick's disease, argyrophilic grain dementia (argyrophilic grain disease), multiple system tauopathy with dementia (MSTD), chromosome 17-linked frontotemporal dementia with Parkinsonism (FTDP-17), neurofibrillary tangle dementia, diffuse neurofibrillary tangles with calcification (DNTC), white matter tauopathy with globular glial inclusions (WMT-GGI), frontotemporal lobar degeneration with tau-positive inclusions (FTLD-tau). Tauopathies also include non-neurodegenerative diseases including: infectious diseases such as Economo's encephalitis sequela and subacute sclerosing panencephalitis; and trauma-induced conditions such as boxer's encephalopathy (Tetsuaki Arai, "Shinkei Naika" (Japanese document), Vol. 72, special number, (Suppl. 6), 2010, pp. 46-51).

Tau can be phosphorylated on a large number of amino acid residues, and phosphorylated tau has been believed to be the pathological tau species in tauopathies. While there are many known phosphorylation sites on tau and anti-tau antibodies with different specificities (e.g., targeting total tau, nonphosphorylated tau, or tau that is phosphorylated at various amino acid residues) in the art, it is still uncertain which phosphorylated tau species is the best target for treating tauopathies. Among the known anti-tau antibodies, some do not distinguish between pathological tau species (e.g., tau in the brain of AD patients) and normal tau (e.g., tau in the brain of healthy human beings), and others do not have a sufficiently high affinity and thus have to be administered at very high doses to reach an effective amount in the brain. Thus, there is unmet need to produce high affinity anti-tau antibodies that specifically target pathological tau species (e.g., tau-pS413).

SUMMARY OF THE INVENTION

The present disclosure provides high affinity antibodies or antigen binding fragments thereof that bind to human tau-pS413 (e.g., tau having the amino acid sequence of SEQ ID NO:1 that is phosphorylated at serine 413). Also provided herein are isolated nucleic acids and vectors comprising polynucleotide sequences encoding such high affinity antibodies or antigen binding fragments thereof, cells (e.g., host cells) comprising such isolated nucleic acids or vectors, compositions or kits comprising such high affinity antibodies or antigen binding fragments thereof, and methods or uses involving such high affinity antibodies or antigen binding fragments thereof.

In one aspect, provided herein is an antibody or antigen binding fragment thereof that binds to tau-pS413.

In one embodiment, the antibody or antigen binding fragment thereof that binds to tau-pS413 comprises a heavy chain variable region complementarity determining region 1 (VH-CDR1) comprising the amino acid sequence of SEQ ID NO:41; a heavy chain variable region complementarity determining region 2 (VH-CDR2) comprising the amino acid sequence of SEQ ID NO:42; and a heavy chain variable region complementarity determining region 3 (VH-CDR3) comprising the amino acid sequence of SEQ ID NO:43; and a light chain variable region complementarity determining region 1 (VL-CDR1) comprising the amino acid sequence of SEQ ID NO:29; a light chain variable region complementarity determining region 2 (VL-CDR2) comprising the amino acid sequence of SEQ ID NO:30; and a light chain variable region complementarity determining region 3 (VL-CDR3) comprising the amino acid sequence of SEQ ID NO:31.

In another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In yet another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In still another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In yet another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In still another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In yet another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In still another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In yet another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In still another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In yet another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In still another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In another embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In yet another embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In still another embodiment, the antibody or antigen binding fragment thereof that binds to tau-pS413 comprises a VH-CDR1 comprising the amino acid sequence of SEQ ID NO:86; a VH-CDR2 comprising the amino acid sequence of SEQ ID NO:87; and a VH-CDR3 comprising the amino acid sequence of SEQ ID NO:88; and a VL-CDR1 comprising the amino acid sequence of SEQ ID NO:83; a VL-CDR2 comprising the amino acid sequence of SEQ ID NO:84; and a VL-CDR3 comprising the amino acid sequence of SEQ ID NO:85.

In one embodiment, the antibody or antigen binding fragment thereof that binds to tau-pS413 comprises a VH-CDR1 comprising the amino acid sequence of SEQ ID NO:92; a VH-CDR2 comprising the amino acid sequence of SEQ ID NO:93; and a VH-CDR3 comprising the amino acid sequence of SEQ ID NO:94; and a VL-CDR1 comprising the amino acid sequence of SEQ ID NO:89; a VL-CDR2 comprising the amino acid sequence of SEQ ID NO:90; and a VL-CDR3 comprising the amino acid sequence of SEQ ID NO:91.

In another embodiment, the antibody or antigen binding fragment thereof that binds to tau-pS413 comprises a VH-CDR1 comprising the amino acid sequence of SEQ ID NO:98; a VH-CDR2 comprising the amino acid sequence of SEQ ID NO:99; and a VH-CDR3 comprising the amino acid sequence of SEQ ID NO:100; and a VL-CDR1 comprising the amino acid sequence of SEQ ID NO:95; a VL-CDR2 comprising the amino acid sequence of SEQ ID NO:96; and a VL-CDR3 comprising the amino acid sequence of SEQ ID NO:97.

In yet another embodiment, the antibody or antigen binding fragment thereof that binds to tau-pS413 comprises a VH-CDR1 comprising the amino acid sequence of SEQ ID NO:104; a VH-CDR2 comprising the amino acid sequence of SEQ ID NO:105; and a VH-CDR3 comprising the amino acid sequence of SEQ ID NO:106; and a VL-CDR1 comprising the amino acid sequence of SEQ ID NO:101; a VL-CDR2 comprising the amino acid sequence of SEQ ID NO:102; and a VL-CDR3 comprising the amino acid sequence of SEQ ID NO:103.

In one embodiment, the antibody or antigen binding fragment thereof that binds to tau-pS413 comprises a VH-CDR1, a VH-CDR2, and a VH-CDR3 of a heavy chain variable region (VH) comprising the amino acid sequence of SEQ ID NO:44; and a VL-CDR1, a VL-CDR2, and a VL-CDR3 of a light chain variable region (VL) comprising the amino acid sequence of SEQ ID NO:32.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:36.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:40.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:28.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:20.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:32.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:36.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:40.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:28.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:20.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:32.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:36.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:40.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:28.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:20.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:32.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:36.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:40.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:28.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:20.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:32.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:36.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:40.

In one embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:32.

In another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:36.

In yet another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:40.

In still another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:28.

In one embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:20.

In another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:32.

In yet another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:36.

In still another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:40.

In one embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:28.

In another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:20.

In yet another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:32.

In still another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:36.

In one embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:40.

In another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:28.

In yet another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:20.

In still another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:32.

In one embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:36.

In another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:40.

In yet another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:28.

In still another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:20.

In one embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:32.

In another embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:36.

In yet another embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:40.

In one embodiment, the antibody or antigen binding fragment thereof that binds to tau-pS413 comprises a VH having the amino acid sequence of SEQ ID NO:44, and a VL having the amino acid sequence of SEQ ID NO:32.

In another embodiment, the antibody or antigen binding fragment thereof that binds to tau-pS413 comprises a VH having the amino acid sequence of SEQ ID NO:44, and a VL having the amino acid sequence of SEQ ID NO:36.

In yet another embodiment, the antibody or antigen binding fragment thereof that binds to tau-pS413 comprises a VH having the amino acid sequence of SEQ ID NO:44, and a VL having the amino acid sequence of SEQ ID NO:40.

In still another embodiment, the antibody or antigen binding fragment thereof that binds to tau-pS413 comprises a VH having the amino acid sequence of SEQ ID NO:44, and a VL having the amino acid sequence of SEQ ID NO:28.

In one embodiment, the antibody or antigen binding fragment thereof that binds to tau-pS413 comprises a VH having the amino acid sequence of SEQ ID NO:44, and a VL having the amino acid sequence of SEQ ID NO:20.

In another embodiment, the antibody or antigen binding fragment thereof that binds to tau-pS413 comprises a VH having the amino acid sequence of SEQ ID NO:48, and a VL having the amino acid sequence of SEQ ID NO:32.

In yet another embodiment, the antibody or antigen binding fragment thereof that binds to tau-pS413 comprises a VH having the amino acid sequence of SEQ ID NO:48, and a VL having the amino acid sequence of SEQ ID NO:36.

In still another embodiment, the antibody or antigen binding fragment thereof that binds to tau-pS413 comprises a VH having the amino acid sequence of SEQ ID NO:48, and a VL having the amino acid sequence of SEQ ID NO:40.

In one embodiment, the antibody or antigen binding fragment thereof that binds to tau-pS413 comprises a VH having the amino acid sequence of SEQ ID NO:48, and a VL having the amino acid sequence of SEQ ID NO:28.

In another embodiment, the antibody or antigen binding fragment thereof that binds to tau-pS413 comprises a VH having the amino acid sequence of SEQ ID NO:48, and a VL having the amino acid sequence of SEQ ID NO:20.

In yet another embodiment, the antibody or antigen binding fragment thereof that binds to tau-pS413 comprises a VH having the amino acid sequence of SEQ ID NO:52, and a VL having the amino acid sequence of SEQ ID NO:32.

In still another embodiment, the antibody or antigen binding fragment thereof that binds to tau-pS413 comprises a VH having the amino acid sequence of SEQ ID NO:52, and a VL having the amino acid sequence of SEQ ID NO:36.

In one embodiment, the antibody or antigen binding fragment thereof that binds to tau-pS413 comprises a VH having the amino acid sequence of SEQ ID NO:52, and a VL having the amino acid sequence of SEQ ID NO:40.

In another embodiment, the antibody or antigen binding fragment thereof that binds to tau-pS413 comprises a VH having the amino acid sequence of SEQ ID NO:52, and a VL having the amino acid sequence of SEQ ID NO:28.

In yet another embodiment, the antibody or antigen binding fragment thereof that binds to tau-pS413 comprises a VH having the amino acid sequence of SEQ ID NO:52, and a VL having the amino acid sequence of SEQ ID NO:20.

In still another embodiment, the antibody or antigen binding fragment thereof that binds to tau-pS413 comprises a VH having the amino acid sequence of SEQ ID NO:56, and a VL having the amino acid sequence of SEQ ID NO:32.

In one embodiment, the antibody or antigen binding fragment thereof that binds to tau-pS413 comprises a VH having the amino acid sequence of SEQ ID NO:56, and a VL having the amino acid sequence of SEQ ID NO:36.

In another embodiment, the antibody or antigen binding fragment thereof that binds to tau-pS413 comprises a VH having the amino acid sequence of SEQ ID NO:56, and a VL having the amino acid sequence of SEQ ID NO:40.

In yet another embodiment, the antibody or antigen binding fragment thereof that binds to tau-pS413 comprises a VH having the amino acid sequence of SEQ ID NO:56, and a VL having the amino acid sequence of SEQ ID NO:28.

In still another embodiment, the antibody or antigen binding fragment thereof that binds to tau-pS413 comprises a VH having the amino acid sequence of SEQ ID NO:56, and a VL having the amino acid sequence of SEQ ID NO:20.

In one embodiment, the antibody or antigen binding fragment thereof that binds to tau-pS413 comprises a VH having the amino acid sequence of SEQ ID NO:24, and a VL having the amino acid sequence of SEQ ID NO:32.

In another embodiment, the antibody or antigen binding fragment thereof that binds to tau-pS413 comprises a VH having the amino acid sequence of SEQ ID NO:24, and a VL having the amino acid sequence of SEQ ID NO:36.

In yet another embodiment, the antibody or antigen binding fragment thereof that binds to tau-pS413 comprises a VH having the amino acid sequence of SEQ ID NO:24, and a VL having the amino acid sequence of SEQ ID NO:40.

In various embodiments of the antibody or antigen-binding fragment thereof that binds to tau-pS413 disclosed herein, the antibody or antigen-binding fragment thereof further comprises a heavy chain constant region having the amino acid sequence of SEQ ID NO:59, 60, 61, 62, 63, 64, 65, 66, 67, or 68. In one embodiment, the antibody or antigen-binding fragment thereof further comprises a heavy chain constant region having the amino acid sequence of SEQ ID NO:59. In another embodiment, the antibody or antigen-binding fragment thereof further comprises a heavy chain constant region having the amino acid sequence of SEQ ID NO:60. In yet another embodiment, the antibody or antigen-binding fragment thereof further comprises a heavy chain constant region having the amino acid sequence of SEQ ID NO:61. In still another embodiment, the antibody or antigen-binding fragment thereof further comprises a heavy chain constant region having the amino acid sequence of SEQ ID NO:62. In one embodiment, the antibody or antigen-binding fragment thereof further comprises a heavy chain constant region having the amino acid sequence of SEQ ID NO:63. In another embodiment, the antibody or antigen-binding fragment thereof further comprises a heavy chain constant region having the amino acid sequence of SEQ ID NO:64. In yet another embodiment, the antibody or antigen-binding fragment thereof further comprises a heavy chain constant region having the amino acid sequence of SEQ ID NO:65. In still another embodiment, the antibody or antigen-binding fragment thereof further comprises a heavy chain constant region having the amino acid sequence of SEQ ID NO:66. In one embodiment, the antibody or antigen-binding fragment thereof further comprises a heavy chain constant region having the amino acid sequence of SEQ ID NO:67. In another embodiment, the antibody or antigen-binding fragment thereof further comprises a heavy chain constant region having the amino acid sequence of SEQ ID NO:68.

In certain embodiments, the antibody or antigen-binding fragment thereof further comprises a light chain constant region having the amino acid sequence of SEQ ID NO:57 or 58. In one embodiment, the antibody or antigen-binding fragment thereof further comprises a light chain constant region having the amino acid sequence of SEQ ID NO:57. In one embodiment, the antibody or antigen-binding fragment thereof further comprises a light chain constant region having the amino acid sequence of SEQ ID NO:58.

In some embodiments, the antibody or antigen-binding fragment thereof further comprises a heavy chain constant region having the amino acid sequence of SEQ ID NO:59, 60, 61, 62, 63, 64, 65, 66, 67, or 68, and a light chain constant region having the amino acid sequence of SEQ ID NO:57 or 58. In one embodiment, the antibody or antigen-binding fragment thereof further comprises a heavy chain constant region having the amino acid sequence of SEQ ID NO:60, and a light chain constant region having the amino acid sequence of SEQ ID NO:58. In another embodiment, the antibody or antigen-binding fragment thereof further comprises a heavy chain constant region having the amino acid sequence of SEQ ID NO:63, and a light chain constant region having the amino acid sequence of SEQ ID NO:58. In yet another embodiment, the antibody or antigen-binding fragment thereof further comprises a heavy chain constant region having the amino acid sequence of SEQ ID NO:68, and a light chain constant region having the amino acid sequence of SEQ ID NO:58.

In certain embodiments, the antibody or antigen-binding fragment thereof comprises a light chain comprising the amino acid sequence of SEQ ID NO:71 and a heavy chain comprising the amino acid sequence of SEQ ID NO:72.

In some embodiments, the antibody or antigen-binding fragment thereof comprises a light chain comprising the amino acid sequence of SEQ ID NO:73 and a heavy chain comprising the amino acid sequence of SEQ ID NO:74.

In other embodiments, the antibody or antigen-binding fragment thereof comprises a light chain comprising the amino acid sequence of SEQ ID NO:75 and a heavy chain comprising the amino acid sequence of SEQ ID NO:76.

In yet other embodiments, the antibody or antigen-binding fragment thereof consists of two light chains comprising the amino acid sequence of SEQ ID NO:71 and two heavy chains comprising the amino acid sequence of SEQ ID NO:72.

In still other embodiments, the antibody or antigen-binding fragment thereof consists of two light chains comprising the amino acid sequence of SEQ ID NO:73 and two heavy chains comprising the amino acid sequence of SEQ ID NO:74.

In yet still other embodiments, the antibody or antigen-binding fragment thereof consists of two light chains comprising the amino acid sequence of SEQ ID NO:75 and two heavy chains comprising the amino acid sequence of SEQ ID NO:76.

In certain embodiments, the antibody or antigen-binding fragment thereof consists of two light chains consisting of the amino acid sequence of SEQ ID NO:71 and two heavy chains consisting of the amino acid sequence of SEQ ID NO:72.

In some embodiments, the antibody or antigen-binding fragment thereof consists of two light chains consisting of the amino acid sequence of SEQ ID NO:73 and two heavy chains consisting of the amino acid sequence of SEQ ID NO:74.

In other embodiments, the antibody or antigen-binding fragment thereof consists of two light chains consisting of the amino acid sequence of SEQ ID NO:75 and two heavy chains consisting of the amino acid sequence of SEQ ID NO:76.

In various embodiments of the antibody or antigen binding fragment thereof described herein, the antibody or antigen binding fragment thereof has an equilibrium dissociation constant (KD) of $1\times10^{-8}$ M or less for tau-pS413. In some embodiments, the antibody or antigen binding fragment thereof has an equilibrium dissociation constant (KD) of $9\times10^{-9}$ M or less for tau-pS413. In other embodiments, the antibody or antigen binding fragment thereof has an equilibrium dissociation constant (KD) of $8\times10^{-9}$ M or less for tau-pS413. In yet other embodiments, the antibody or antigen binding fragment thereof has an equilibrium dissociation constant (KD) of $7\times10^{-9}$ M or less for tau-pS413. In some embodiments, the antibody or antigen binding fragment thereof has an equilibrium dissociation constant (KD) of $6\times10^{-9}$ M or less for tau-pS413. In other embodiments, the antibody or antigen binding fragment thereof has an equilibrium dissociation constant (KD) of $5\times10^{-9}$ M or less for tau-pS413. In yet other embodiments, the antibody or antigen binding fragment thereof has an equilibrium dissociation constant (KD) of $4\times10^{-9}$ M or less for tau-pS413. In still other embodiments, the antibody or antigen binding fragment thereof has an equilibrium dissociation constant (KD) of $3\times10^{-9}$ M or less for tau-pS413. In yet still other embodiments, the antibody or antigen binding fragment thereof has an equilibrium dissociation constant (KD) of $2\times10^{-9}$ M or less for tau-pS413. In some embodiments, the KD is measured by Surface Plasmon Resonance (SPR) assay with the antibody or antigen binding fragment thereof being immobilized. In one embodiment, the KD is measured by Biacore. In another embodiment, the KD is measured by KinExA.

In another aspect, provided is an isolated nucleic acid encoding various polypeptides disclosed herein.

In certain embodiments, the isolated nucleic acid encodes the VH of various antibodies or antigen binding fragments thereof disclosed herein. In some embodiments, the isolated nucleic acid encodes the VL of various antibodies or antigen binding fragments thereof disclosed herein. In other embodiments, the isolated nucleic acid encodes the VH and the VL of various antibodies or antigen binding fragments thereof disclosed herein.

In certain embodiments, the isolated nucleic acid encodes the heavy chain of various antibodies or antigen binding fragments thereof disclosed herein. In some embodiments, the isolated nucleic acid encodes the light chain of various antibodies or antigen binding fragments thereof disclosed herein. In other embodiments, the isolated nucleic acid encodes the heavy chain and the light chain of various antibodies or antigen binding fragments thereof disclosed herein.

In yet another aspect, provided is an expression vector comprising the various isolated nucleic acids disclosed herein.

In still another aspect, provided is a host cell comprising one or more of the various isolated nucleic acids or one of more of the various expression vectors disclosed herein. In some embodiments, the host cell comprises one of more of the various isolated nucleic acids disclosed herein. In other embodiments, the host cell comprises one of more of the various expression vectors disclosed herein.

In yet still another aspect, provided is a method of producing the antibody or antigen binding fragment thereof disclosed herein. In certain embodiments, the method of producing the antibody or antigen binding fragment thereof disclosed herein comprises expressing an isolated nucleic acid described herein under conditions wherein the antibody or antigen binding fragment thereof is expressed. In some embodiments, the method of producing the antibody or antigen binding fragment thereof disclosed herein comprises expressing an expression vector described herein under conditions wherein the antibody or antigen binding fragment thereof is expressed. In other embodiments, the method of producing the antibody or antigen binding fragment thereof disclosed herein comprises culturing the host cell comprising an isolated nucleic acid or an expression vector described herein under conditions wherein the antibody or antigen binding fragment thereof is expressed.

In another aspect, provided is a composition comprising the antibodies or antigen binding fragments thereof described herein and a pharmaceutically acceptable carrier.

In some embodiments, the composition further comprises an additional agent.

In particular embodiments, the additional agent is an agent effective to treat the same or different disorder as the anti-tau-pS413 antibodies or antigen-binding fragments thereof disclosed herein are being used to treat. In some embodiments, the additional agent is an agent effective to mitigate one or more side effects of the anti-tau-pS413 antibodies or antigen-binding fragments thereof disclosed herein. Exemplary additional agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide for immunization, phosphodiesterase inhibitors, serotonin receptor antagonists, anti-amyloid beta peptide antibodies, growth hormone, neurotrophic factor, brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, stem cell factor (SCF), or a different anti-tau antibody.

In yet another aspect, provided is a kit comprising the antibodies or antigen binding fragments thereof described herein.

In still another aspect, provided is a method of treating tauopathy in a subject, comprising administering to the subject an effective amount of the antibodies or antigen binding fragments thereof described herein.

In some embodiments, the method further comprises administering to the subject an additional agent.

In particular embodiments, the additional agent is an agent effective to treat the same or different disorder as the anti-tau-pS413 antibodies or antigen-binding fragments thereof disclosed herein are being used to treat. In some embodiments, the additional agent is an agent effective to mitigate one or more side effects of the anti-tau-pS413 antibodies or antigen-binding fragments thereof disclosed herein. Exemplary additional agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide for immunization, phosphodiesterase inhibitors, serotonin receptor antagonists, anti-amyloid beta peptide antibodies, growth hormone, neurotrophic factor, brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, stem cell factor (SCF), or a different anti-tau antibody.

In some embodiments of the method, the tauopathy is a neurodegenerative disease, including but not limited to Alzheimer's disease (AD), corticobasal degeneration (CBD) or corticobasal syndrome (CBS), progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), or frontotemporal lobar degeneration with tau pathology (FTLD-tau). In one embodiment, the tauopathy is AD. In another embodiment, the tauopathy is CBD. In yet another embodiment, the tauopathy is progressive supranuclear palsy. In still another embodiment, the tauopathy is Pick's disease. In one embodiment, the tauopathy is argyrophilic grain dementia. In another embodiment, the tauopathy is MSTD. In yet another embodiment, the tauopathy is FTDP-17. In still another embodiment, the tauopathy is dementia with neurofibrillary tangles. In one embodiment, the tauopathy is DNTC. In another embodiment, the tauopathy is WMT-GGI. In yet another embodiment, the tauopathy is FTLD-tau.

In other embodiments of the method, the tauopathy is a non-neurodegenerative disease, including but not limited to infectious diseases, such as Economo's encephalitis sequela and subacute sclerosing panencephalitis, and trauma-induced conditions, such as boxer's encephalopathy. In one embodiment, the tauopathy is Economo's encephalitis sequela. In another embodiment, the tauopathy is subacute sclerosing panencephalitis. In yet another embodiment, the tauopathy is boxer's encephalopathy.

In yet still another aspect, provided is a method of decreasing the amount of tau-pS413 in the brain of a subject, comprising administering to the subject in need thereof an effective amount of the antibodies or antigen binding fragments thereof of described herein.

In some embodiments, the method further comprises administering to the subject an additional agent.

In particular embodiments, the additional agent is an agent effective to treat the same or different disorder as the anti-tau-pS413 antibodies or antigen-binding fragments thereof disclosed herein are being used to treat. In some embodiments, the additional agent is an agent effective to mitigate one or more side effects of the anti-tau-pS413 antibodies or antigen-binding fragments thereof disclosed herein. Exemplary additional agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide for immunization, phosphodiesterase inhibitors, serotonin receptor antagonists, anti-amyloid beta peptide antibodies, growth hormone, neurotrophic factor, brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, stem cell factor (SCF), or a different anti-tau antibody.

In yet additional embodiments, provided is the use of an antibody or antigen binding fragment thereof as disclosed herein to treat tauopathy in a subject.

In yet additional embodiments, provided is the use of an antibody or antigen binding fragment thereof as disclosed herein for the treatment of tauopathy in a subject.

In yet additional embodiments, provided is the use of an antibody or antigen binding fragment thereof as disclosed herein for the preparation of a medicament to treat tauopathy in a subject.

In some embodiments of the various uses described herein, the tauopathy is Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, or boxer's encephalopathy. In one embodiment, the tauopathy is AD. In another embodiment, the tauopathy is CBD. In yet another embodiment, the tauopathy is progressive supranuclear palsy. In still another embodiment, the tauopathy is Pick's disease. In one embodiment, the tauopathy is argyrophilic grain dementia. In another embodiment, the tauopathy is MSTD. In yet another embodiment, the tauopathy is FTDP-17. In still another embodiment, the tauopathy is dementia with neurofibrillary tangles. In one embodiment, the tauopathy is DNTC. In another embodiment, the tauopathy is WMT-GGI. In yet another embodiment, the tauopathy is FTLD-tau. In one embodiment, the tauopathy is Economo's encephalitis sequela. In another embodiment, the tauopathy is subacute sclerosing panencephalitis. In yet another embodiment, the tauopathy is boxer's encephalopathy.

In yet a further embodiment, provided is an antibody or antigen binding fragment thereof as disclosed herein for use in a method for treating tauopathy in a subject.

In yet additional embodiments, provided is an antibody or antigen binding fragment thereof as disclosed herein for use in a method for diagnosing tauopathy in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows representative graph of curve fits with OD 450 nm as readouts and hIgGs as isotype control. FIG. 3B shows representative graph of curve fits with % of occupancy as readouts.

FIG. 4A illustrates schematic representation of the neutralization protocol. FIGS. 4B and 4C represent AlphaLISA® data used to confirm successful depletion of tau-pS413 and total tau, respectively. FIG. 4D shows representative images demonstrating pathological MC1 tau (red spots) in neurons treated with P2 fraction (right panel) compared to no-treatment control (left panel). FIG. 4E represents the high-content image analysis of MC1 tau pathology in hiPSC neurons 5 days after seeding with immuno-depleted AD brain-derived P2 fractions with various concentration of exemplary anti-tau-pS413 antibodies or IgG control.

FIG. 7A shows A.U. readings in a tau-pS413 MSD assay for CSF samples from AD patients or non-AD humans in the presence of increased concentration of V8-AFM-hIgG1-LALA-YTE. FIG. 7B shows the percentage of reduction of free tau-pS413 (unbound by V8-AFM-hIgG1-LALA-YTE) in CSF samples from AD patients or non-AD humans.

DETAILED DESCRIPTION

Abbreviations

Figure 1A:
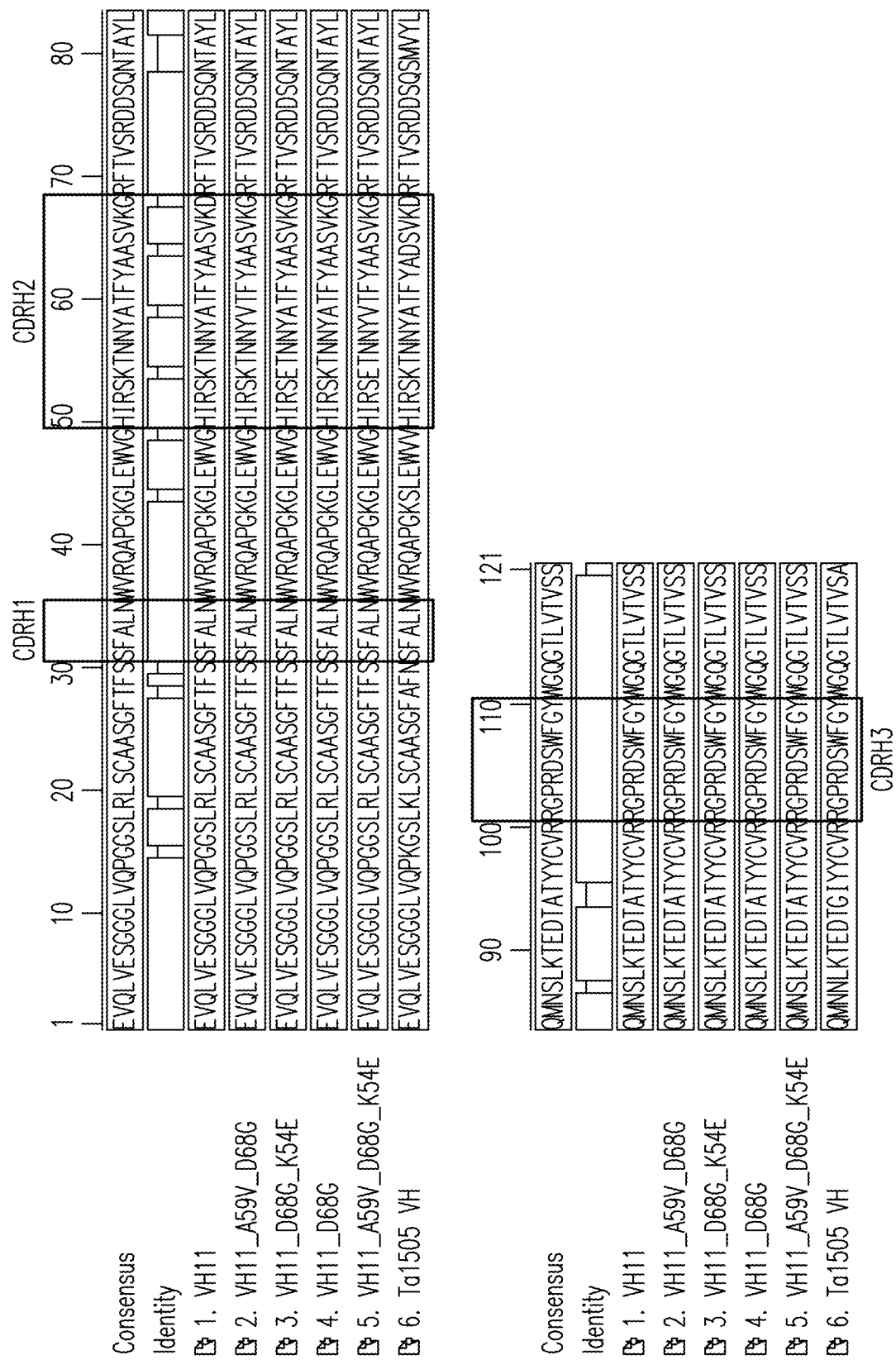
FIGS. 1A and 1B show amino acid sequence alignment of VH (FIG. 1A) and VL (FIG. 1B) of representative antibodies described herein. CDRs shown in these figures are defined by the Kabat numbering system.

Throughout the detailed description and examples of the invention the following abbreviations will be used:

ADCC Antibody-dependent cellular cytotoxicity
CDC Complement-dependent cytotoxicity
CDR Complementarity determining region in the immunoglobulin variable regions
CHO Chinese hamster ovary
EC50 concentration resulting in 50% efficacy or binding
ELISA Enzyme-linked immunosorbent assay
FR Antibody framework region: the immunoglobulin variable regions excluding the CDR regions.
IC50 concentration resulting in 50% inhibition IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb Monoclonal antibody
PK Pharmacokinetics
V region The segment of IgG chains which is variable in sequence between different antibodies. It extends to Kabat residue 109 in the light chain and 113 in the heavy chain.
VH Immunoglobulin heavy chain variable region
VL Immunoglobulin light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise. Similarly, the plural forms of words include their corresponding singular references unless the context clearly indicates otherwise.

The term "tau protein," when used in the context of human species, refers to six isoforms of human tau protein having the amino acid sequences defined in SEQ ID NOs:1 to 6, i.e., 4R2N (defined in SEQ ID NO:1), 4R1N (defined in SEQ ID NO:2), 4R0N (defined in SEQ ID NO:3), 3R2N (defined in SEQ ID NO:4), 3R1N (defined in SEQ ID NO:5), and 3R0N (defined in SEQ ID NO:6), as well as gene variants thereof. The tau protein according to the present invention also encompasses proteins having similarities or identities of 80% or more to the amino acid sequence of the human tau protein defined in SEQ ID NO:1 in accordance with the BLAST method (with default conditions of PBLAST provided by NCBI) and their isoforms. Such tau proteins also include tau derived from non-human species, such as chimpanzees, macaques, horses, pigs, dogs, mice, rabbits, and rats. It is possible to produce a therapeutic or prophylactic agent targeted to tau derived from such a non-human animal for the purpose of improving the cognitive function of the target animal.

The term "tau peptide" used herein means a peptide including a part of the amino acid sequence of a tau protein. The position of the tau peptide derived from a tau protein should not be limited. The length of the tau peptide should also not be limited, but should preferably have an amino acid length of four or more, particularly six or more, more particularly eight or more.

The term "tau" used herein means a tau protein or a tau peptide collectively.

In the context of the present invention, the position of an amino acid residue in a tau protein or a tau peptide is indicated by an amino acid number, which is identified based on the amino acid sequence defined in SEQ ID NO:1 for clarification. For example, "serine 413," "Ser413," or "S413" refers to the amino acid residue corresponding to Ser413 of SEQ ID NO:1, including the serine residue at amino acid position 413 of SEQ ID NO:1 (4R2N), amino acid position 384 of SEQ ID NO:2 (4R1N), amino acid position 355 of SEQ ID NO:3 (4R0N), amino acid position 382 of SEQ ID NO:4 (3R2N), amino acid position 353 of SEQ ID NO:5 (3R1N), or amino acid position 324 of SEQ ID NO:6 (3R0N). Correspondence of the positions of amino acid residues between tau isoforms is shown in TABLE 1 below.

TABLE 1

Isoforms of human tau protein

| Amino acid residue | Isoform | | | | | |
|---|---|---|---|---|---|---|
| | 4R2N | 4R1N | 4R0N | 3R2N | 3R1N | 3R0N |
| | Sequence | | | | | |
| | SEQ ID NO: 1 | SEQ ID NO: 2 | SEQ ID NO: 3 | SEQ ID NO: 4 | SEQ ID NO: 5 | SEQ ID NO: 6 |
| | Amino acid position/number | | | | | |
| Asn | 410 | 381 | 352 | 379 | 350 | 321 |
| Val | 411 | 382 | 353 | 380 | 351 | 322 |
| Ser | 412 | 383 | 354 | 381 | 352 | 323 |
| Ser | 413 | 384 | 355 | 382 | 353 | 324 |
| Thr | 414 | 385 | 356 | 383 | 354 | 325 |
| Gly | 415 | 386 | 357 | 384 | 355 | 326 |
| Ser | 416 | 387 | 358 | 385 | 356 | 327 |
| Ile | 417 | 388 | 359 | 386 | 357 | 328 |
| Asp | 418 | 389 | 360 | 387 | 358 | 329 |
| Met | 419 | 390 | 361 | 388 | 359 | 330 |
| Val | 420 | 391 | 362 | 389 | 360 | 331 |
| Asp | 421 | 392 | 363 | 390 | 361 | 332 |

Figure 1B:
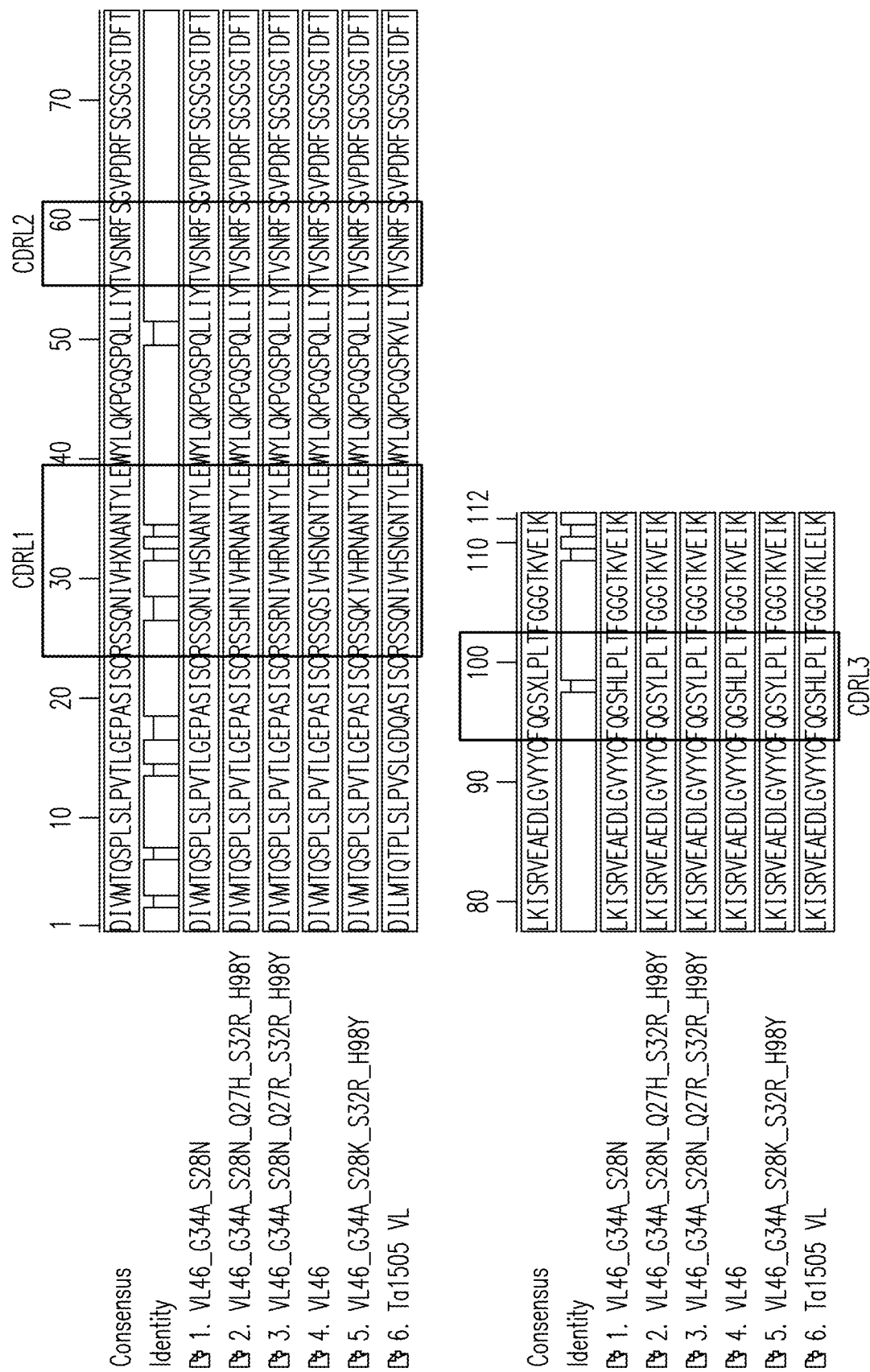

While TABLE 1 shows the positions of amino acid residues of the recited isoforms corresponding to positions 410 to 421 of the amino acid sequence defined in SEQ ID NO:1, correspondence of the positions of amino acid residues in other regions can easily be recognized based on, e.g., FIGS. 1A and 1B of WO 2018/254390, the entirety of which disclosure is incorporated by reference herein. In order to know corresponding positions of amino acids in isoforms or homologues, a person skilled in the art would be able to carry out analysis using pairwise sequence alignment such as Needleman-Wunsch method or Smith-Waterman method, or multiple sequence alignment such as ClustalW method or PRRP method. As an example of analysis of corresponding positions, FIGS. 1A and 1B of WO 2018/254390 show an alignment of the amino acid sequences of the six human isoforms (indicated with one letter codes) based on ClustalW. These figures indicate that the structure surrounding the amino acid residue corresponding to Ser413 of the amino acid sequence defined in SEQ ID NO:1 is conserved among the six isoforms, and also help to identify the amino acids corresponding to one another.

The statement that an amino acid residue is "phosphorylated" as used herein means that a phosphate group is ester-linked to the side chain of the amino acid residue. Typical amino acid residues that may be phosphorylated include serine (Ser), threonine (Thr), and tyrosine (Tyr).

The term "tau-pS413," "tau-PS413," "tau-pSer413," "pS413-tau," "PS413-tau," or "pSer413-tau," as used herein, refers to a tau protein or peptide that is phosphorylated at the amino acid residue corresponding to Ser413 of SEQ ID NO:1, including the serine residue at amino acid position 413 of SEQ ID NO:1 (4R2N), amino acid position 384 of SEQ ID NO:2 (4R1N), amino acid position 355 of SEQ ID NO:3 (4R0N), amino acid position 382 of SEQ ID NO:4 (3R2N), amino acid position 353 of SEQ ID NO:5 (3R1N), or amino acid position 324 of SEQ ID NO:6 (3R0N). In some embodiments, tau-pS413 is phosphorylated only at S413. In certain embodiments, tau-pS413 is phosphorylated at S413 and one or more additional amino acid residues.

"Anti-tau-pS413 antibody" as used herein refers to an antibody that specifically binds to a tau-pS413 protein or a tau-pS413 peptide.

Each of the term "V1-AFM," "V2-AFM," "V3-AFM," "V4-AFM," "V5-AFM," "V6-AFM," "V7-AFM," or "V8-AFM," as used herein, refers to an affinity matured variant of HmzTa1505-hIgG4-S228P as described herein, comprising the defined VH and VL as described in TABLE 4, with SEQ ID NOs disclosed in TABLES 5 and 6. Each term encompasses antibodies with any one of known heavy chain constant region (e.g., IgG1, IgG1-LALA, IgG1-LALA-YTE, IgG2, IgG3, IgG4, IgG4-S228P, etc.) or variant thereof and any one of known light chain constant region (e.g., lambda or kappa) or variant thereof.

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as tau, is the "affinity" of the antibody or functional fragment for that epitope or target. Unless indicated otherwise, as used herein, "binding affinity" refers to intrinsic binding affinity which reflects a 1:1 interaction between members of a binding pair (e.g., antibody and antigen). The ratio of dissociation rate ($k_{off}$) to association rate ($k_{on}$) of an antibody to a monovalent antigen ($k_{off}/k_{on}$) is the "dissociation constant" (or "equilibrium dissociation constant" as used interchangeably) KD, which is inversely related to affinity. The lower the KD value, the higher the affinity of the antibody. The value of KD varies for different complexes of antibody and antigen and depends on both $k_{on}$ and $k_{off}$. The dissociation constant KD for an antibody provided herein can be determined using any method provided herein or any other method well known to those skilled in the art, such as surface plasmon resonance (SPR) assay, including but not limited to Biacore and KinExA. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the "avidity." The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively. Unless indicated otherwise, the term "affinity" or "binding affinity" as used herein refers to monovalent (1:1) interaction between an anti-tau-pS413 antibody and a tau-pS413 protein or peptide. The KD can be measured using SPR with either the anti-tau-pS413 antibody or tau-pS413 immobilized. The KD values disclosed in this specification are measured with the anti-tau-pS413 antibody immobilized.

The terms "antibodies that specifically bind to tau-pS413," "antibodies that specifically bind to a tau-pS413 protein or peptide," and analogous terms are used interchangeably herein and refer to antibodies that specifically bind to a tau-pS413 polypeptide, such as a tau-pS413 protein or peptide (e.g., human tau-pS413 such as a human tau-pS413 protein or peptide). An antibody that specifically binds to tau-pS413 (e.g., human tau-pS413) may be cross-reactive with tau-pS413 derived from another species (e.g., cynomolgus tau-pS413). In certain embodiments, an antibody that specifically binds to tau-pS413 does not cross-react with other [tau] proteins or peptides, such as a tau protein or peptide that is not phosphorylated at S413 or a tau protein or peptide that is phosphorylated at another amino acid residue other than S413. An antibody that specifically binds to tau-pS413 can be identified, for example, by immunoassays, Biacore, or other techniques known to those of skill in the art. An antibody binds specifically to tau-pS413 when it binds to tau-pS413 with higher affinity than to any cross-reactive protein or peptide as determined using experimental techniques, such as radioimmunoassays (MA) and enzyme linked immunosorbent assays (ELISAs). Typically, a specific reaction will be at least twice background signal or noise and may be more than 10 times background. See, e.g., Fundamental Immunology 332-36 (Paul ed., 2d ed. 1989) for a discussion regarding antibody specificity. With regard to the binding of an antibody to a target molecule, the term "specific binding," "specifically binds to," or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding to a target can be determined by competition with a control molecule that is similar to the target, for example, an excess of non-labeled target. In this case, specific binding is indicated if the binding of the labeled target to a probe is competitively inhibited by excess unlabeled target.

"Administrating" or "administration," as it applies to an animal, human, subject, cell, tissue, organ, or biological fluid, refers to contact of an exogenous pharmaceutical, therapeutic, diagnostic agent, or composition to the animal, human, subject, cell, tissue, organ, or biological fluid.

The term "subject" includes any organism, preferably an animal, more preferably a mammal (e.g., human, rat, mouse, dog, cat, or rabbit). In a preferred embodiment, the term "subjects" refers to a human.

The term "antibody," "immunoglobulin," or "Ig" is used interchangeably herein, and is used in the broadest sense and specifically encompasses, for example, individual monoclonal antibodies (including neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments of the antibodies, as described below. An antibody can be human, humanized, chimeric and/or affinity matured, as well as an antibody from other species, for example, mouse and rabbit, etc. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments thereof) of any of the above, which refers to a portion of an antibody heavy or light chain polypeptide that retains some or all of the binding activity of the antibody from which the fragment was derived. Non-limiting examples of functional fragments (e.g., antigen-binding fragments thereof) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a tau-pS413 protein or peptide (e.g., one or more CDRs of an anti-tau-pS413 antibody). Such antibody fragments can be found in, for example, Harlow and Lane, Antibodies: A Laboratory Manual (1989); Mol. Biology and Biotechnology: A Comprehensive Desk Reference (Myers ed., 1995); Huston et al., 1993, Cell Biophysics 22:189-224; Pluckthun and Skerra, 1989, Meth. Enzymol. 178:497-515; and Day, Advanced Immunochemistry (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule.

A "Fab fragment" is comprised of one light chain and the $C_H1$ and variable regions of one heavy chain. The heavy chain of a Fab molecule cannot form a disulfide bond with another heavy chain molecule. An "Fab fragment" can be the product of papain cleavage of an antibody.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the VH domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H^2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

An "Fv fragment" or "Fv region" comprises the variable regions from both the heavy and light chains, but lacks the constant regions.

The term "monoclonal antibody," as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

In general, the basic antibody structural unit comprises a tetramer. Each tetramer includes two identical pairs of polypeptide chains, each pair having one "light" (about 25 kDa) and one "heavy" chain (about 50-70 kDa). The aminoterminal portion of each chain includes a variable region of about 100 to 110 or more amino acids primarily responsible for antigen recognition. The carboxy-terminal portion of the heavy chain may define a constant region primarily responsible for effector function.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

"Variable region," "variable domain," or "V region" or "V chain" as used herein means the segment of IgG chains which is variable in sequence between different antibodies. A "variable region" of an antibody refers to the variable region of the antibody light chain or the variable region of the antibody heavy chain, either alone or in combination. The variable region of the heavy chain may be referred to as "VH." The variable region of the light chain may be referred to as "VL." Typically, the variable regions of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of Sequences of Proteins of Immunological Interest, Kabat, et al.; National Institutes of Health, Bethesda, Md.; 5th ed.; NIH Publ. No. 91-3242 (1991) ("Kabat 1"); Kabat (1978) Adv. Prot. Chem. 32:1-75 ("Kabat 2"); Kabat, et al., (1977) J. Biol. Chem. 252:6609-6616 ("Kabat 3"); Chothia, et al., (1987) J Mol. Biol. 196:901-917 ("Chothia 1") or Chothia, et al., (1989) Nature 342:878-883 ("Chothia 2").

A "CDR" refers to one of three hypervariable regions (H1, H2, or H3) within the non-framework region of the antibody $V_H$ β-sheet framework, or one of three hypervariable regions (L1, L2, or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable domains (see Kabat 1-3, supra). CDR region sequences also have been defined structurally by Chothia as those residues that are not part of the conserved β-sheet framework, and thus are able to adapt to a different conformation (see Chothia 1-2, supra). Both Kabat and Chothia methodologies for defining CDR sequences within antibody variable regions are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art. Correspondence between the numbering system, including, for example, the Kabat numbering and the IMGT unique numbering system, is well known to one skilled in the art and shown below in TABLE 2. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system. In yet still other embodiments, the CDRs are as defined by any numbering system that is known to those skilled in the art.

TABLE 2

Correspondence of Amino Acid Positions Between CDR Numbering Systems

|  | IMGT | Kabat | AbM | Chothia | Contact |
|---|---|---|---|---|---|
| $V_H$ CDR1 | 27-38 | 31-35 | 26-35 | 26-32 | 30-35 |
| $V_H$ CDR2 | 56-65 | 50-65 | 50-58 | 52-56 | 47-58 |
| $V_H$ CDR3 | 105-117 | 95-102 | 95-102 | 95-102 | 93-101 |
| $V_L$ CDR1 | 27-38 | 24-34 | 24-34 | 24-34 | 30-36 |
| $V_L$ CDR2 | 56-65 | 50-56 | 50-56 | 50-56 | 46-55 |
| $V_L$ CDR3 | 105-117 | 89-97 | 89-97 | 89-97 | 89-96 |

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in TABLE 3.

TABLE 3

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The term "epitope," as used herein, is defined in the context of a molecular interaction between an "antigen binding molecule," such as an antibody (Ab), and its corresponding "antigen" (Ag). Generally, "epitope" refers to the area or region on an Ag to which an Ab specifically binds, i.e. the area or region in physical contact with the Ab. Physical contact may be defined through distance criteria (e.g. a distance cut-off of 4 Å) for atoms in the Ab and Ag molecules. Epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three-dimensional structure of the protein is in an altered conformation, such as following activation or binding of another protein or ligand.

"Isolated nucleic acid" means a DNA or RNA polynucleotide of genomic, mRNA, cDNA, or synthetic origin or some combination thereof which is not associated with all or a portion of a polynucleotide in which the isolated polynucleotide is found in nature, or is linked to a polynucleotide to which it is not linked in nature. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences or non-coding sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "host cell," "cell line," and "cell culture" are used interchangeably and all such designations include progeny.

"Treat" or "treatment" means to administer an agent, such as a composition containing any of the antibodies or antigen binding fragments thereof of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting, delaying or slowing the progression of such symptom(s) by any clinically measurable degree. The amount of an agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

Tau-pS413

Tau is a protein encoded by the MAPT gene, which is located on chromosome 17 (17q21) in the human genome. The tau protein is one of the microtubule-binding proteins abundantly expressed in the central nervous system. The tau protein has been found to be a major constituent protein in the paired helical filaments and straight filaments forming NFT in AD, one of the most prominent neurodegenerative diseases, and its intracellular accumulation has been demonstrated in a variety of neuropathological conditions. The diseases caused by such intracellular accumulation of tau are collectively referred to as "tauopathies" (Tetsuaki Arai, "Shinkei Naika" (Japanese document), Vol. 72, special number, (Suppl. 6), 2010, pp. 46-51). Tauopathies include neurodegenerative diseases such as Alzheimer's disease (AD), corticobasal degeneration (CBD) or corticobasal syndrome (CBS), progressive supranuclear palsy, Pick's disease, argyrophilic grain dementia (argyrophilic grain disease), multiple system tauopathy with dementia (MSTD), chromosome 17-linked frontotemporal dementia with Parkinsonism (FTDP-17), neurofibrillary tangle dementia, diffuse neurofibrillary tangles with calcification (DNTC), white matter tauopathy with globular glial inclusions (WMT-GGI), frontotemporal lobar degeneration with tau-positive inclusions (FTLD-tau). Tauopathies also include non-neurodegenerative diseases including: infectious diseases such as Economo's encephalitis sequela and subacute sclerosing panencephalitis; and trauma-induced conditions such as boxer's encephalopathy (Tetsuaki Arai, "Shinkei Naika" (Japanese document), Vol. 72, special number, (Suppl. 6), 2010, pp. 46-51).

The MAPT gene has been identified as consisting of 13 exons disposed on the genome, which can be expressed as multiple different protein isoforms via alternative splicing (Tetsuaki Arai, "Shinkei Naika" (Japanese document), Vol. 72, special number, (Suppl. 6), 2010, pp. 46-51). The structure of tau comprises an N-terminal acidic domain containing 0-2 repetitive sequences (N) of 29 amino acids depended on alternative splicing of exon 2 and exon 3 (N0-N2), an intermediate domain rich in proline, and a C-terminal microtubule-binding domain (encoded by exons 9 to 12) containing 3 (3R) or 4 (4R) repetitive sequences (R) that contribute to microtubule binding (Alistair Burns et al. (Edit.), Dementia, 3rd Edition, 2005, CRC Press, pp. 408-464; Tetsuaki Arai, "Shinkei Naika" (Japanese document), Vol. 72, special number, (Suppl. 6), 2010, pp. 46-51). Therefore, human tau has six representative isoforms: 3R0N (352 amino acids), 3R1N (381 amino acids), 3R2N (410 amino acids), 4R0N (383 amino acids), 4R1N (412 amino acids), and 4R2N (441 amino acids), depending on the number of 29 amino acid repetitive sequences (N) and microtubule-binding repetitive sequences (R) that it contains. In order to unambiguously identify the position of an amino acid residue in any of these tau isoforms, the amino acid numbers (1 to 441) of the longest isoform, i.e., 4R2N (defined in SEQ ID NO:1), are used as a reference herein. For example, "Ser413" refers to the serine residue at the 413th amino acid position in 4R2N (defined in SEQ ID NO:1), which corresponds to the serine at the 384th amino acid position in 4R1N (defined in SEQ ID NO:2), the 355th amino acid position in 4R0N (defined in SEQ ID NO:3), the 382nd amino acid position in 3R2N (defined in SEQ ID NO:4), the 353rd amino acid position in 3R1N (defined in SEQ ID NO:5), and the 324th amino acid position in 3R0N (defined in SEQ ID NO:6).

In addition, tau accumulated in neurodegenerative diseases is characterized by being highly modified via phosphorylation. In patients exhibiting mild cognitive impairment, a correlation is observed between the level of phosphorylated tau in the spinal fluid and the degree of pituitary atrophy, suggesting phosphorylated tau as a highly reliable biomarker for neurodegeneration in patients with tauopathy (Wendy Noble et al., Expert Opinion on Drug Discovery, 2011, Vol. 6, No. 8, pp. 797-810). However, there are a large number of sites which can be phosphorylated in tau, while virtually no information exists regarding which antibodies for which phosphorylation sites are effective to treat tauopathy.

Furthermore, when using an antibody as an active compound for a therapeutic or prophylactic agent, it is necessary to consider the amount of the antibody to be administered in patients, in order to avoid side effects and minimize problems such as, immunogenicity, manufacture capacity, and medical cost. This is especially important in relation to doses for chronic diseases or genetic diseases. In addition, while the brain is the target organ to be treated in cognitive disorders such as AD, systemic administration by intravenous or subcutaneous routes is generally thought to result in a low migration rate of antibodies from the blood to the brain, due to the presence of the blood-brain barrier. Accordingly, there is a significant problem that antibodies used for treatment of cognitive disorders are expected to require high dosages, compared to treatment for diseases involving other organs. Thus, against the backdrop of these challenges, it is particularly unexpected and surprising for the inventors to have generated high affinity anti-tau-pS413 antibodies that can achieve sufficient therapeutic effects without affecting non-pathological tau or having to be administered at very high dosages.

High Affinity Anti-Tau-pS413 Antibodies or Antigen Binding Fragments Thereof

Previous disclosures of anti-tau-pS413 antibodies include WO 2013/180238 and WO 2018/254390, the entirety of which disclosures are incorporated by reference herein. Distinct from the prior disclosures, the present invention provides higher affinity anti-tau-pS413 antibodies (e.g., various isotypes of V1-AFM, V2-AFM, V3-AFM, V4-AFM, V5-AFM, V6-AFM, V7-AFM, or V8-AFM) or antigen binding fragments thereof. These high affinity anti-tau-pS413 antibodies or antigen binding fragments thereof show increased binding potency compared to previously disclosed anti-tau-pS413 antibodies (e.g., at least 10- to 40-fold increase) to recombinant tau-pS413 protein or peptide, tau transgenic mouse brains, AD patients' brain homogenates, and AD patients' CSF samples. Such high affinity antibodies (e.g., various isotypes of V1-AFM, V2-AFM, V3-AFM, V4-AFM, V5-AFM, V6-AFM, V7-AFM, or V8-AFM) or antigen binding fragments thereof can also effectively prevent the development of tau pathology in hu-iPSC neurons induced by seeding of AD brain homogenates.

In this disclosure, optimized (e.g., higher affinity) versions of the previously disclosed anti-tau-pS413 antibodies were obtained by affinity maturation to improve potency or by structure-based modeling to identify one or more amino acid mutations (e.g., K54E or K54D) that lowers pI (isoelectric point), improves affinity, and increases production of the antibody molecule. In some embodiments, the optimized (e.g., higher affinity) anti-tau-pS413 antibodies can be obtained by affinity maturation. In certain embodiments, the optimized (e.g., higher affinity) anti-tau-pS413 antibodies can be obtained by structure-based modeling to identify one or more amino acid mutations (e.g., K54E or K54D) that lowers pI, improves affinity, and increases production of the antibody molecule. In other embodiments, the optimized (e.g., higher affinity) anti-tau-pS413 antibodies can be obtained by affinity maturation and structure-based modeling to identify one or more amino acid mutations (e.g., K54E or K54D) that lowers pI, improves affinity, and increases production of the antibody molecule. In additional embodiments, the heavy chain constant region of the optimized (e.g., higher affinity) anti-tau-pS413 antibodies is switched from IgG4-S228P isotype to IgG1-LALA to improve colloidal stability and lower viscosity while maintaining reduced Fc effector function. In further embodiments, a half-life extension YTE mutation is integrated into the Fc region to increase half-life of the optimized (e.g., higher affinity) anti-tau-pS413 antibodies. In yet other embodiments, the heavy chain constant region of the optimized (e.g., higher affinity) anti-tau-pS413 antibodies is switched from IgG4-S228P isotype to IgG1-LALA and a half-life extension YTE mutation is integrated into the Fc region. In a preferred embodiment, an optimized (e.g., higher affinity) anti-tau-pS413 antibody (e.g., V1-AFM-hIgG1-LALA-YTE, V2-AFM-hIgG1-LALA-YTE, V3-AFM-hIgG1-LALA-YTE, V4-AFM-hIgG1-LALA-YTE, V5-AFM-hIgG1-LALA-YTE, V6-AFM-hIgG1-LALA-YTE, V7-AFM-hIgG1-LALA-YTE, or V8-AFM-hIgG1-LALA-YTE) is obtained by 1) affinity maturation, 2) structure-based modeling to identify a mutation (e.g., K54E or K54D) that lowers pI, improves affinity, and increases production of the antibody molecule, 3) switching isotype to IgG1-LALA to improve colloidal stability and lower viscosity while maintaining reduced Fc effector function, and 4) integrating a YTE mutation into the Fc region to extend half-life.

In one embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In yet another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In still another embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, the antibody or antigen binding fragment thereof that binds to tau-pS413 comprises a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In yet another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In still another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In another embodiment, the antibody or antigen binding fragment thereof that binds to tau-pS413 comprises a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In yet another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In still another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In yet another embodiment, the antibody or antigen binding fragment thereof that binds to tau-pS413 comprises a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In still another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In yet another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In still another embodiment, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In another embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In yet another embodiment, the antibody or antigen binding fragment thereof that binds to tau-pS413 comprises a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In still another embodiment, the antibody or antigen binding fragment thereof that binds to tau-pS413 comprises a VH-CDR1 comprising the amino acid sequence of SEQ ID NO:86; a VH-CDR2 comprising the amino acid sequence of SEQ ID NO:87; and a VH-CDR3 comprising the amino acid sequence of SEQ ID NO:88; and a VL-CDR1 comprising the amino acid sequence of SEQ ID NO:83; a VL-CDR2 comprising the amino acid sequence of SEQ ID NO:84; and a VL-CDR3 comprising the amino acid sequence of SEQ ID NO:85.

In one embodiment, the antibody or antigen binding fragment thereof that binds to tau-pS413 comprises a VH-CDR1 comprising the amino acid sequence of SEQ ID NO:92; a VH-CDR2 comprising the amino acid sequence of SEQ ID NO:93; and a VH-CDR3 comprising the amino acid sequence of SEQ ID NO:94; and a VL-CDR1 comprising the amino acid sequence of SEQ ID NO:89; a VL-CDR2 comprising the amino acid sequence of SEQ ID NO:90; and a VL-CDR3 comprising the amino acid sequence of SEQ ID NO:91.

In another embodiment, the antibody or antigen binding fragment thereof that binds to tau-pS413 comprises a VH-CDR1 comprising the amino acid sequence of SEQ ID NO:98; a VH-CDR2 comprising the amino acid sequence of SEQ ID NO:99; and a VH-CDR3 comprising the amino acid sequence of SEQ ID NO:100; and a VL-CDR1 comprising the amino acid sequence of SEQ ID NO:95; a VL-CDR2 comprising the amino acid sequence of SEQ ID NO:96; and a VL-CDR3 comprising the amino acid sequence of SEQ ID NO:97.

In yet another embodiment, the antibody or antigen binding fragment thereof that binds to tau-pS413 comprises a VH-CDR1 comprising the amino acid sequence of SEQ ID NO:104; a VH-CDR2 comprising the amino acid sequence of SEQ ID NO:105; and a VH-CDR3 comprising the amino acid sequence of SEQ ID NO:106; and a VL-CDR1 comprising the amino acid sequence of SEQ ID NO:101; a VL-CDR2 comprising the amino acid sequence of SEQ ID NO:102; and a VL-CDR3 comprising the amino acid sequence of SEQ ID NO:103.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:32. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:36. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:40. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:28. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:20. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:32. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:36. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:40. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:28. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:20. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:32. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:36. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:40. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:28. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:20. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:32. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:36. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:40. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:28. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In still another embodiment, the antibody or antigen binding fragment thereof that binds to tau-pS413 comprises a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:20. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:32. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In another embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:36. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In yet another embodiment, the antibody or antigen binding fragment thereof that binds to tau-pS413 comprises a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:40. In some embodiments, the CDRs are as defined by the Kabat numbering system. In other embodiments, the CDRs are as defined by the IMGT numbering system. In yet other embodiments, the CDRs are as defined by the AbM numbering system. In still other embodiments, the CDRs are as defined by the Chothia numbering system. In yet other embodiments, the CDRs are as defined by the Contact numbering system.

In one embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:32.

In another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:36.

In yet another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:40.

In still another embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:28.

In one embodiment, the antibody or antigen binding fragment thereof that binds to tau-pS413 comprises a VH having at least 90% amino acid sequence identity to the amino acid sequence of SEQ ID NO:44, and a VL having at least 90% amino acid sequence identity to the amino acid sequence of SEQ ID NO:20.

In another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:32.

In yet another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:36.

In still another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:40.

In one embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:28.

In another embodiment, the antibody or antigen binding fragment thereof that binds to tau-pS413 comprises a VH having at least 90% amino acid sequence identity to the amino acid sequence of SEQ ID NO:48, and a VL having at least 90% amino acid sequence identity to the amino acid sequence of SEQ ID NO:20.

In yet another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:32.

In still another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:36.

In one embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:40.

In another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:28.

In yet another embodiment, the antibody or antigen binding fragment thereof that binds to tau-pS413 comprises a VH having at least 90% amino acid sequence identity to the amino acid sequence of SEQ ID NO:52, and a VL having at least 90% amino acid sequence identity to the amino acid sequence of SEQ ID NO:20.

In still another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:32.

In one embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:36.

In another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:40.

In yet another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:28.

In still another embodiment, the antibody or antigen binding fragment thereof that binds to tau-pS413 comprises a VH having at least 90% amino acid sequence identity to the amino acid sequence of SEQ ID NO:56, and a VL having at least 90% amino acid sequence identity to the amino acid sequence of SEQ ID NO:20.

In one embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:32.

In another embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:36.

In yet another embodiment, the antibody or antigen binding fragment thereof that binds to tau-pS413 comprises a VH having at least 90% amino acid sequence identity to the amino acid sequence of SEQ ID NO:24, and a VL having at least 90% amino acid sequence identity to the amino acid sequence of SEQ ID NO:40.

In one embodiment, the antibody or antigen binding fragment thereof that binds to tau-pS413 comprises a VH having the amino acid sequence of SEQ ID NO:44, and a VL having the amino acid sequence of SEQ ID NO:32.

In another embodiment, the antibody or antigen binding fragment thereof that binds to tau-pS413 comprises a VH having the amino acid sequence of SEQ ID NO:44, and a VL having the amino acid sequence of SEQ ID NO:36.

In yet another embodiment, the antibody or antigen binding fragment thereof that binds to tau-pS413 comprises a VH having the amino acid sequence of SEQ ID NO:44, and a VL having the amino acid sequence of SEQ ID NO:40.

In still another embodiment, the antibody or antigen binding fragment thereof that binds to tau-pS413 comprises a VH having the amino acid sequence of SEQ ID NO:44, and a VL having the amino acid sequence of SEQ ID NO:28.

In one embodiment, the antibody or antigen binding fragment thereof that binds to tau-pS413 comprises a VH having the amino acid sequence of SEQ ID NO:44, and a VL having the amino acid sequence of SEQ ID NO:20.

In another embodiment, the antibody or antigen binding fragment thereof that binds to tau-pS413 comprises a VH having the amino acid sequence of SEQ ID NO:48, and a VL having the amino acid sequence of SEQ ID NO:32.

In yet another embodiment, the antibody or antigen binding fragment thereof that binds to tau-pS413 comprises a VH having the amino acid sequence of SEQ ID NO:48, and a VL having the amino acid sequence of SEQ ID NO:36.

In still another embodiment, the antibody or antigen binding fragment thereof that binds to tau-pS413 comprises a VH having the amino acid sequence of SEQ ID NO:48, and a VL having the amino acid sequence of SEQ ID NO:40.

In one embodiment, the antibody or antigen binding fragment thereof that binds to tau-pS413 comprises a VH having the amino acid sequence of SEQ ID NO:48, and a VL having the amino acid sequence of SEQ ID NO:28.

In another embodiment, the antibody or antigen binding fragment thereof that binds to tau-pS413 comprises a VH having the amino acid sequence of SEQ ID NO:48, and a VL having the amino acid sequence of SEQ ID NO:20.

In yet another embodiment, the antibody or antigen binding fragment thereof that binds to tau-pS413 comprises a VH having the amino acid sequence of SEQ ID NO:52, and a VL having the amino acid sequence of SEQ ID NO:32.

In still another embodiment, the antibody or antigen binding fragment thereof that binds to tau-pS413 comprises a VH having the amino acid sequence of SEQ ID NO:52, and a VL having the amino acid sequence of SEQ ID NO:36.

In one embodiment, the antibody or antigen binding fragment thereof that binds to tau-pS413 comprises a VH having the amino acid sequence of SEQ ID NO:52, and a VL having the amino acid sequence of SEQ ID NO:40.

In another embodiment, the antibody or antigen binding fragment thereof that binds to tau-pS413 comprises a VH having the amino acid sequence of SEQ ID NO:52, and a VL having the amino acid sequence of SEQ ID NO:28.

In yet another embodiment, the antibody or antigen binding fragment thereof that binds to tau-pS413 comprises a VH having the amino acid sequence of SEQ ID NO:52, and a VL having the amino acid sequence of SEQ ID NO:20.

In still another embodiment, the antibody or antigen binding fragment thereof that binds to tau-pS413 comprises a VH having the amino acid sequence of SEQ ID NO:56, and a VL having the amino acid sequence of SEQ ID NO:32.

In one embodiment, the antibody or antigen binding fragment thereof that binds to tau-pS413 comprises a VH having the amino acid sequence of SEQ ID NO:56, and a VL having the amino acid sequence of SEQ ID NO:36.

In another embodiment, the antibody or antigen binding fragment thereof that binds to tau-pS413 comprises a VH having the amino acid sequence of SEQ ID NO:56, and a VL having the amino acid sequence of SEQ ID NO:40.

In yet another embodiment, the antibody or antigen binding fragment thereof that binds to tau-pS413 comprises a VH having the amino acid sequence of SEQ ID NO:56, and a VL having the amino acid sequence of SEQ ID NO:28.

In still another embodiment, the antibody or antigen binding fragment thereof that binds to tau-pS413 comprises a VH having the amino acid sequence of SEQ ID NO:56, and a VL having the amino acid sequence of SEQ ID NO:20.

In one embodiment, the antibody or antigen binding fragment thereof that binds to tau-pS413 comprises a VH having the amino acid sequence of SEQ ID NO:24, and a VL having the amino acid sequence of SEQ ID NO:32.

In another embodiment, the antibody or antigen binding fragment thereof that binds to tau-pS413 comprises a VH having the amino acid sequence of SEQ ID NO:24, and a VL having the amino acid sequence of SEQ ID NO:36.

In yet another embodiment, the antibody or antigen binding fragment thereof that binds to tau-pS413 comprises a VH having the amino acid sequence of SEQ ID NO:24, and a VL having the amino acid sequence of SEQ ID NO:40.

In various embodiments of the antibody or antigen-binding fragment thereof that binds to tau-pS413 disclosed herein, the antibody or antigen-binding fragment thereof further comprises a heavy chain constant region having the amino acid sequence of SEQ ID NO:59, 60, 61, 62, 63, 64, 65, 66, 67, or 68. In one embodiment, the antibody or antigen-binding fragment thereof further comprises a heavy chain constant region having the amino acid sequence of SEQ ID NO:59. In another embodiment, the antibody or antigen-binding fragment thereof further comprises a heavy chain constant region having the amino acid sequence of SEQ ID NO:60. In yet another embodiment, the antibody or antigen-binding fragment thereof further comprises a heavy chain constant region having the amino acid sequence of SEQ ID NO:61. In still another embodiment, the antibody or antigen-binding fragment thereof further comprises a heavy chain constant region having the amino acid sequence of SEQ ID NO:62. In one embodiment, the antibody or antigen-binding fragment thereof further comprises a heavy chain constant region having the amino acid sequence of SEQ ID NO:63. In another embodiment, the antibody or antigen-binding fragment thereof further comprises a heavy chain constant region having the amino acid sequence of SEQ ID NO:64. In yet another embodiment, the antibody or antigen-binding fragment thereof further comprises a heavy chain constant region having the amino acid sequence of SEQ ID NO:65. In still another embodiment, the antibody or antigen-binding fragment thereof further comprises a heavy chain constant region having the amino acid sequence of SEQ ID NO:66. In one embodiment, the antibody or antigen-binding fragment thereof further comprises a heavy chain constant region having the amino acid sequence of SEQ ID NO:67. In another embodiment, the antibody or antigen-binding fragment thereof further comprises a heavy chain constant region having the amino acid sequence of SEQ ID NO:68. In certain embodiments, the lysine residue at the C-terminus of the heavy chain constant region is present. In other embodiments, the lysine residue at the C-terminus of the heavy chain constant region is absent.

In certain embodiments, the antibody or antigen-binding fragment thereof further comprises a light chain constant region having the amino acid sequence of SEQ ID NO:57 or 58. In one embodiment, the antibody or antigen-binding fragment thereof further comprises a light chain constant region having the amino acid sequence of SEQ ID NO:57. In one embodiment, the antibody or antigen-binding fragment thereof further comprises a light chain constant region having the amino acid sequence of SEQ ID NO:58.

In some embodiments, the antibody or antigen-binding fragment thereof further comprises a heavy chain constant region having the amino acid sequence of SEQ ID NO:59, 60, 61, 62, 63, 64, 65, 66, 67, or 68, and a light chain constant region having the amino acid sequence of SEQ ID NO:57 or 58. In one embodiment, the antibody or antigen-binding fragment thereof further comprises a heavy chain constant region having the amino acid sequence of SEQ ID NO:59, and a light chain constant region having the amino acid sequence of SEQ ID NO:57. In another embodiment, the antibody or antigen-binding fragment thereof further comprises a heavy chain constant region having the amino acid sequence of SEQ ID NO:60, and a light chain constant region having the amino acid sequence of SEQ ID NO:57. In yet another embodiment, the antibody or antigen-binding fragment thereof further comprises a heavy chain constant region having the amino acid sequence of SEQ ID NO:61, and a light chain constant region having the amino acid sequence of SEQ ID NO:57. In still another embodiment, the antibody or antigen-binding fragment thereof further comprises a heavy chain constant region having the amino acid sequence of SEQ ID NO:62, and a light chain constant region having the amino acid sequence of SEQ ID NO:57. In one embodiment, the antibody or antigen-binding fragment thereof further comprises a heavy chain constant region having the amino acid sequence of SEQ ID NO:63, and a light chain constant region having the amino acid sequence of SEQ ID NO:57. In another embodiment, the antibody or antigen-binding fragment thereof further comprises a heavy chain constant region having the amino acid sequence of SEQ ID NO:64, and a light chain constant region having the amino acid sequence of SEQ ID NO:57. In yet another embodiment, the antibody or antigen-binding fragment thereof further comprises a heavy chain constant region having the amino acid sequence of SEQ ID NO:65, and a light chain constant region having the amino acid sequence of SEQ ID NO:57. In still another embodiment, the antibody or antigen-binding fragment thereof further comprises a heavy chain constant region having the amino acid sequence of SEQ ID NO:66, and a light chain constant region having the amino acid sequence of SEQ ID NO:57. In one embodiment, the antibody or antigen-binding fragment thereof further comprises a heavy chain constant region having the amino acid sequence of SEQ ID NO:67, and a light chain constant region having the amino acid sequence of SEQ ID NO:57. In another embodiment, the antibody or antigen-binding fragment thereof further comprises a heavy chain constant region having the amino acid sequence of SEQ ID NO:68, and a light chain constant region having the amino acid sequence of SEQ ID NO:57. In yet another embodiment, the antibody or antigen-binding fragment thereof further comprises a heavy chain constant region having the amino acid sequence of SEQ ID NO:59, and a light chain constant region having the amino acid sequence of SEQ ID NO:58. In still another embodiment, the antibody or antigen-binding fragment thereof further comprises a heavy chain constant region having the amino acid sequence of SEQ ID NO:60, and a light chain constant region having the amino acid sequence of SEQ ID NO:58. In one embodiment, the antibody or antigen-binding fragment thereof further comprises a heavy chain constant region having the amino acid sequence of SEQ ID NO:61, and a light chain constant region having the amino acid sequence of SEQ ID NO:58. In another embodiment, the antibody or antigen-binding fragment thereof further comprises a heavy chain constant region having the amino acid sequence of SEQ ID NO:62, and a light chain constant region having the amino acid sequence of SEQ ID NO:58. In yet another embodiment, the antibody or antigen-binding fragment thereof further comprises a heavy chain constant region having the amino acid sequence of SEQ ID NO:63, and a light chain constant region having the amino acid sequence of SEQ ID NO:58. In still another embodiment, the antibody or antigen-binding fragment thereof further comprises a heavy chain constant region having the amino acid sequence of SEQ ID NO:64, and a light chain constant region having the amino acid sequence of SEQ ID NO:58. In one embodiment, the antibody or antigen-binding fragment thereof further comprises a heavy chain constant region having the amino acid sequence of SEQ ID NO:65, and a light chain constant region having the amino acid sequence of SEQ ID NO:58. In another embodiment, the antibody or antigen-binding fragment thereof further comprises a heavy chain constant region having the amino acid sequence of SEQ ID NO:66, and a light chain constant region having the amino acid sequence of SEQ ID NO:58. In yet another embodiment, the antibody or antigen-binding fragment thereof further comprises a heavy chain constant region having the amino acid sequence of SEQ ID NO:67, and a light chain constant region having the amino acid sequence of SEQ ID NO:58. In still another embodiment, the antibody or antigen-binding fragment thereof further comprises a heavy chain constant region having the amino acid sequence of SEQ ID NO:68, and a light chain constant region having the amino acid sequence of SEQ ID NO:58. In certain embodiments, the lysine residue at the C-terminus of the heavy chain constant region is present. In other embodiments, the lysine residue at the C-terminus of the heavy chain constant region is absent.

In certain embodiments, the antibody or antigen-binding fragment thereof comprises a light chain comprising the amino acid sequence of SEQ ID NO:71 and a heavy chain comprising the amino acid sequence of SEQ ID NO:72. In certain embodiments, the lysine residue at the C-terminus of the heavy chain constant region is present. In other embodiments, the lysine residue at the C-terminus of the heavy chain constant region is absent.

In some embodiments, the antibody or antigen-binding fragment thereof comprises a light chain comprising the amino acid sequence of SEQ ID NO:73 and a heavy chain comprising the amino acid sequence of SEQ ID NO:74. In certain embodiments, the lysine residue at the C-terminus of the heavy chain constant region is present. In other embodiments, the lysine residue at the C-terminus of the heavy chain constant region is absent.

In other embodiments, the antibody or antigen-binding fragment thereof comprises a light chain comprising the amino acid sequence of SEQ ID NO:75 and a heavy chain comprising the amino acid sequence of SEQ ID NO:76. In certain embodiments, the lysine residue at the C-terminus of the heavy chain constant region is present. In other embodiments, the lysine residue at the C-terminus of the heavy chain constant region is absent.

In yet other embodiments, the antibody or antigen-binding fragment thereof consists of two light chains comprising the amino acid sequence of SEQ ID NO:71 and two heavy chains comprising the amino acid sequence of SEQ ID NO:72. In certain embodiments, the lysine residue at the C-terminus of the heavy chain constant region is present. In other embodiments, the lysine residue at the C-terminus of the heavy chain constant region is absent.

In still other embodiments, the antibody or antigen-binding fragment thereof consists of two light chains comprising the amino acid sequence of SEQ ID NO:73 and two heavy chains comprising the amino acid sequence of SEQ ID NO:74. In certain embodiments, the lysine residue at the C-terminus of the heavy chain constant region is present. In other embodiments, the lysine residue at the C-terminus of the heavy chain constant region is absent.

In yet still other embodiments, the antibody or antigen-binding fragment thereof consists of two light chains comprising the amino acid sequence of SEQ ID NO:75 and two heavy chains comprising the amino acid sequence of SEQ ID NO:76. In certain embodiments, the lysine residue at the C-terminus of the heavy chain constant region is present. In other embodiments, the lysine residue at the C-terminus of the heavy chain constant region is absent.

In certain embodiments, the antibody or antigen-binding fragment thereof consists of two light chains consisting of the amino acid sequence of SEQ ID NO:71 and two heavy chains consisting of the amino acid sequence of SEQ ID NO:72. In certain embodiments, the lysine residue at the C-terminus of the heavy chain constant region is present. In other embodiments, the lysine residue at the C-terminus of the heavy chain constant region is absent.

In some embodiments, the antibody or antigen-binding fragment thereof consists of two light chains consisting of the amino acid sequence of SEQ ID NO:73 and two heavy chains consisting of the amino acid sequence of SEQ ID NO:74. In certain embodiments, the lysine residue at the C-terminus of the heavy chain constant region is present. In other embodiments, the lysine residue at the C-terminus of the heavy chain constant region is absent.

In other embodiments, the antibody or antigen-binding fragment thereof consists of two light chains consisting of the amino acid sequence of SEQ ID NO:75 and two heavy chains consisting of the amino acid sequence of SEQ ID NO:76. In certain embodiments, the lysine residue at the C-terminus of the heavy chain constant region is present. In other embodiments, the lysine residue at the C-terminus of the heavy chain constant region is absent.

In various embodiments of the antibody or antigen binding fragment thereof described herein, the antibody or antigen binding fragment thereof has an equilibrium dissociation constant (KD) of $1\times10^{-8}$ M or less, $9\times10^{-9}$ M or less, $8\times10^{-9}$ M or less, $7\times10^{-9}$ M or less, $6\times10^{-9}$ M or less, $5\times10^{-9}$ M or less, $4\times10^{-9}$ M or less, $3\times10^{-9}$ M or less, or $2\times10^{-9}$ M or less for tau-pS413. In certain embodiments, the antibody or antigen binding fragment thereof has an equilibrium dissociation constant (KD) of $1\times10^{-8}$ M or less for tau-pS413. In some embodiments, the antibody or antigen binding fragment thereof has an equilibrium dissociation constant (KD) of $9\times10^{-9}$ M or less for tau-pS413. In other embodiments, the antibody or antigen binding fragment thereof has an equilibrium dissociation constant (KD) of $8\times10^{-9}$ M or less for tau-pS413. In certain embodiments, the antibody or antigen binding fragment thereof has an equilibrium dissociation constant (KD) of $7\times10^{-9}$ M or less for tau-pS413. In some embodiments, the antibody or antigen binding fragment thereof has an equilibrium dissociation constant (KD) of $6\times10^{-9}$ M or less for tau-pS413. In other embodiments, the antibody or antigen binding fragment thereof has an equilibrium dissociation constant (KD) of $5\times10^{-9}$ M or less for tau-pS413. In yet other embodiments, the antibody or antigen binding fragment thereof has an equilibrium dissociation constant (KD) of $4\times10^{-9}$ M or less for tau-pS413. In still other embodiments, the antibody or antigen binding fragment thereof has an equilibrium dissociation constant (KD) of $3\times10^{-9}$ M or less for tau-pS413. In yet still other embodiments, the antibody or antigen binding fragment thereof has an equilibrium dissociation constant (KD) of $2\times10^{-9}$ M or less for tau-pS413. In some embodiments, the KD is measured by Surface Plasmon Resonance (SPR) assay. In certain embodiments, the KD is measured by Surface Plasmon Resonance (SPR) assay with the antibody or antigen binding fragment thereof being immobilized. In other embodiments, the KD is measured by Surface Plasmon Resonance (SPR) assay with the antigen being immobilized. In one embodiment, the KD is measured by Biacore. In another embodiment, the KD is measured by KinExA. In one specific embodiment, the KD is measured by Biacore with the antibody or antigen binding fragment thereof being immobilized.

In certain embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $1\times10^{-8}$ M or less for tau-pS413. In some embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $9\times10^{-9}$ M or less for tau-pS413. In other embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $8\times10^{-9}$ M or less for tau-pS413. In certain embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $7\times10^{-9}$ M or less for tau-pS413. In some embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $6\times10^{-9}$ M or less for tau-pS413. In other embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $5\times10^{-9}$ M or less for tau-pS413. In yet other embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $4\times10^{-9}$ M or less for tau-pS413. In still other embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $3\times10^{-9}$ M or less for tau-pS413. In yet still other embodiments, the antibody or antigen binding fragment thereof that binds to tau-pS413 comprises a VH-CDR1 comprising the amino acid sequence of SEQ ID NO:53; a VH-CDR2 comprising the amino acid sequence of SEQ ID NO:54; a VH-CDR3 comprising the amino acid sequence of SEQ ID NO:55; a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; and has a KD of $2\times10^{-9}$ M or less for tau-pS413. In a specific embodiment, the KD is measured by Biacore with the antibody or antigen binding fragment thereof being immobilized.

In some embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $1\times10^{-8}$ M or less for tau-pS413. In certain embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $9\times10^{-9}$ M or less for tau-pS413. In other embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $8\times10^{-9}$ M or less for tau-pS413. In some embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $7\times10^{-9}$ M or less for tau-pS413. In certain embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $6\times10^{-9}$ M or less for tau-pS413. In other embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $5\times10^{-9}$ M or less for tau-pS413. In yet other embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $4\times10^{-9}$ M or less for tau-pS413. In still other embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $3\times10^{-9}$ M or less for tau-pS413. In yet still other embodiments, the antibody or antigen binding fragment thereof that binds to tau-pS413 comprises a VH-CDR1, a VH-CDR2, and a VH-CDR3 of a VH comprising the amino acid sequence of SEQ ID NO:56 and a VL-CDR1, a VL-CDR2, and a VL-CDR3 of a VL comprising the amino acid sequence of SEQ ID NO:36; and has a KD of $2\times10^{-9}$ M or less for tau-pS413. In a specific embodiment, the KD is measured by Biacore with the antibody or antigen binding fragment thereof being immobilized.

In certain embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $1\times10^{-8}$ M or less for tau-pS413. In some embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $9\times10^{-9}$ M or less for tau-pS413. In other embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $8\times10^{-9}$ M or less for tau-pS413. In certain embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $7\times10^{-9}$ M or less for tau-pS413. In some embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $6\times10^{-9}$ M or less for tau-pS413. In other embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $5\times10^{-9}$ M or less for tau-pS413. In yet other embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $4\times10^{-9}$ M or less for tau-pS413. In still other embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $3\times10^{-9}$ M or less for tau-pS413. In yet still embodiments, the antibody or antigen binding fragment thereof that binds to tau-pS413 comprises a VH comprising at least 90% amino acid sequence identity to the amino acid sequence of SEQ ID NO:56 and a VL comprising at least 90% amino acid sequence identity to the amino acid sequence of SEQ ID NO:36; and has a KD of $2\times10^{-9}$ M or less for tau-pS413. In a specific embodiment, the KD is measured by Biacore with the antibody or antigen binding fragment thereof being immobilized.

The present disclosure further includes functional fragments of the anti-tau-pS413 antibodies disclosed herein. Non-limiting examples of functional fragments (e.g., antigen-binding fragments such as tau-pS413-binding fragments) include single-chain Fvs (scFv) (e.g., including monospecific, bispecific, etc.), Fab fragments, F(ab') fragments, F(ab)$_2$ fragments, F(ab') 2 fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a tau-pS413 antigen (e.g., one or more CDRs of an anti-tau-pS413 antibody). Such antibody fragments can be found in, for example, Harlow and Lane, Antibodies: A Laboratory Manual (1989); Mol. Biology and Biotechnology: A Comprehensive Desk Reference (Myers ed., 1995); Huston et al., 1993, Cell Biophysics 22:189-224; Pluckthun and Skerra, 1989, Meth. Enzymol. 178:497-515; Day, Advanced Immunochemistry (2d ed. 1990); Hudson et al., 2003, Nature Med. 9:129-34.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention comprises antibodies and antigen binding fragments of any of these classes or subclasses of antibodies.

In one embodiment, the antibody or antigen binding fragment comprises a heavy chain constant region, e.g. a human constant region, such as γ1, γ2, γ3, or γ4 human heavy chain constant region or a variant thereof. In another embodiment, the antibody or antigen binding fragment comprises a light chain constant region, e.g. a human light chain constant region, such as lambda or kappa human light chain region or variant thereof.

Antibody Engineering of the Fc Region

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. See Presta (2005) *J. Allergy Clin. Immunol.* 116:731 at 734-35.

In one embodiment, the constant domain (CH1-hinge-CH2-CH3) of human wild type IgG1 is modified with two amino acid substitutions, L234A and L235A (sometimes referred to as "LALA" mutations) that reduce/ablate effector function. In another embodiment, the constant domain (CH1-hinge-CH2-CH3) of human wild type IgG1 is modified with three amino acid substitutions, L234A, L235A and D265S that reduce/ablate effector function. In yet another embodiment, the constant domain (CH1-hinge-CH2-CH3) of human wild type IgG1 is modified with three amino acid substitutions, M252Y, S254T, and T256E that increase half-life of the antibody in serum. In still another embodiment, the constant domain (CH1-hinge-CH2-CH3) of human wild type IgG1 is modified with five amino acid substitutions, L234A, L235A, M252Y, S254T, and T256E that reduce/ablate effector function and increase half-life of the antibody in serum. In yet still another embodiment, the constant domain (CH1-hinge-CH2-CH3) of human wild type IgG1 is modified with six amino acid substitutions, L234A, L235A, D265S, M252Y, S254T, and T256E that reduce/ablate effector function and increase half-life of the antibody in serum. In another embodiment, the constant domain (CH1-hinge-CH2-CH3) of human wild type IgG1 is modified with the amino acid substitution N297A, which eliminates a glycosylation site and reduces/ablates effector function. In still another embodiment, the constant domain (CH1-hinge-CH2-CH3) of human wild type IgG1 with the amino acid substitution N297Q, which eliminates a glycosylation site and reduces/ablates effector function.

In one embodiment, the antibody is an IgG4 isotype antibody comprising a Serine to Proline mutation at an amino acid position corresponding to position 228 (S228P;

EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the antibody is modified to increase its biological half-life. Various approaches are possible. For example, one or more of the following amino acid mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues at positions 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues at positions 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase or decrease the ability of the antibody to mediate antibody dependent cellular cytotoxicity (ADCC) and/or to increase or decrease the affinity of the antibody for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibody to mediate effector function and/or to increase anti-inflammatory properties by modifying amino acid residues at positions 243 and 264. In one embodiment, the Fc region of the antibody is modified by changing the amino acid residues at positions 243 and 264 to alanine. In one embodiment, the Fc region is modified to decrease the ability of the antibody to mediate effector function and/or to increase anti-inflammatory properties by modifying amino acid residues at positions 243, 264, 267 and 328.

In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibody may also include glycans having an increased amount of bisecting GlcNAc structures. Such altered glycosylation patterns have been demonstrated to increase the ADCC ability of antibodies. Such modifications can be accomplished by, for example, expressing the antibody in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1176195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as

*Lemna* (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Alternatively, the fucose residues of the antibody can be cleaved off using a fucosidase enzyme; e.g., the fucosidase α-L-fucosidase removes fucosyl residues from antibodies (Tarentino et al. (1975) *Biochem.* 14:5516-23).

Antibodies disclosed herein further include those produced in lower eukaryote host cells, in particular fungal host cells such as yeast and filamentous fungi have been genetically engineered to produce glycoproteins that have mammalian- or human-like glycosylation patterns (see, for example, Choi et al, (2003) *Proc. Natl. Acad. Sci.* 100: 5022-5027; Hamilton et al., (2003) *Science* 301: 1244-1246; Hamilton et al., (2006) Science 313: 1441-1443). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (see, for example, Li et al., (2006) *Nat. Biotechnol.* 24: 210-215).

Antibody Conjugates

The anti-tau-pS413 antibodies or antigen binding fragments thereof disclosed herein can also be conjugated to one or more agents (e.g., a peptide or chemical moiety). The chemical moiety may be, inter alia, a polymer, a radionuclide, or a therapeutic or prophylactic agent. In particular embodiments, the chemical moiety is a polymer which increases the half-life of the antibody molecule in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG-conjugated single-chain antibodies. Wen, et al., (2001) (*Bioconj. Chem.* 12:545-553) disclose conjugating antibodies with PEG that is attached to a radiometal chelator (diethylenetriaminpentaacetic acid (DTPA)).

The antibodies and antibody fragments disclosed herein may be pegylated, for example to increase its biological (e.g., serum) half-life. To pegylate an antibody, the antibody, or fragment thereof, typically is reacted with a reactive form of polyethylene glycol (PEG), such as a reactive ester or aldehyde derivative of PEG, under conditions in which one or more PEG groups become attached to the antibody or antibody fragment. In particular embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

The antibodies and antibody fragments disclosed herein may also be conjugated to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as but not limited to iodine ($^{131}$I $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga and $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, or $^{117}$Sn; positron emitting metals using various positron emission tomographies; and non-radioactive paramagnetic metal ions.

In other embodiments, the antibodies or antigen binding fragments thereof can be recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins. In particular, provided herein are fusion proteins comprising an antigen-binding fragment of an antibody provided herein (e.g., a Fab fragment, Fc fragment, Fv fragment, F(ab)$_2$ fragment, a VH domain, a VH CDR, a VL domain, or a VL CDR) and a heterologous protein, polypeptide, or peptide. In one embodiment, the heterologous protein, polypeptide, or peptide that the antibody is fused to is useful for targeting the antibody to a particular cell type, such as a neuron cell. For example, an antibody that binds to a cell surface receptor expressed by a particular neuron cell type may be fused or conjugated to a modified antibody provided herein.

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407.

Methods of Using High Affinity Anti-Tau-pS413 Antibodies or Antigen Binding Fragments Thereof The present disclosure also includes methods of using the high affinity anti-tau-pS413 antibodies (e.g., various isotypes of V1-AFM, V2-AFM, V3-AFM, V4-AFM, V5-AFM, V6-AFM, V7-AFM, or V8-AFM) or antigen binding fragments thereof described herein. These antibodies can be used in treating, diagnosing, or monitoring progress of tauopathy, or decreasing the amount of tau-pS413 in the brain of a subject having tauopathy.

In one aspect, provided is a method of treating tauopathy in a subject, comprising administering to the subject an effective amount of the antibodies (e.g., various isotypes of V1-AFM, V2-AFM, V3-AFM, V4-AFM, V5-AFM, V6-AFM, V7-AFM, or V8-AFM) or antigen binding fragments thereof described herein.

In yet still another aspect, provided is a method of decreasing the amount of tau-pS413 in the brain of a subject having tauopathy, comprising administering to the subject in need thereof an effective amount of the antibodies (e.g., various isotypes of V1-AFM, V2-AFM, V3-AFM, V4-AFM, V5-AFM, V6-AFM, V7-AFM, or V8-AFM) or antigen binding fragments thereof of described herein.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein to treat tauopathy in a subject.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein to decrease the amount of tau-pS413 in the brain of a subject having tauopathy.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for the treatment of tauopathy in a subject.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for the preparation of a medicament to treat tauopathy in a subject.

In yet a further embodiment, provided is an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for use in a method for treating tauopathy in a subject.

In yet another embodiment, provided is an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for use in a method for decreasing the amount of tau-pS413 in the brain of a subject having tauopathy.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39.

In another embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:86; a VH-CDR2 comprising the amino acid sequence of SEQ ID NO:87; and a VH-CDR3 comprising the amino acid sequence of SEQ ID NO:88; and a VL-CDR1 comprising the amino acid sequence of SEQ ID NO:83; a VL-CDR2 comprising the amino acid sequence of SEQ ID NO:84; and a VL-CDR3 comprising the amino acid sequence of SEQ ID NO:85.

In yet another embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:92; a VH-CDR2 comprising the amino acid sequence of SEQ ID NO:93; and a VH-CDR3 comprising the amino acid sequence of SEQ ID NO:94; and a VL-CDR1 comprising the amino acid sequence of SEQ ID NO:89; a VL-CDR2 comprising the amino acid sequence of SEQ ID NO:90; and a VL-CDR3 comprising the amino acid sequence of SEQ ID NO:91.

In still another embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:98; a VH-CDR2 comprising the amino acid sequence of SEQ ID NO:99; and a VH-CDR3 comprising the amino acid sequence of SEQ ID NO:100; and a VL-CDR1 comprising the amino acid sequence of SEQ ID NO:95; a VL-CDR2 comprising the amino acid sequence of SEQ ID NO:96; and a VL-CDR3 comprising the amino acid sequence of SEQ ID NO:97.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1 comprising the amino acid sequence of SEQ ID NO:104; a VH-CDR2 comprising the amino acid sequence of SEQ ID NO:105; and a VH-CDR3 comprising the amino acid sequence of SEQ ID NO:106; and a VL-CDR1 comprising the amino acid sequence of SEQ ID NO:101; a VL-CDR2 comprising the amino acid sequence of SEQ ID NO:102; and a VL-CDR3 comprising the amino acid sequence of SEQ ID NO:103.

In another embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:32.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:36.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:40.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:28.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:44; and a VL-CDR1, a VL-CDR2, and a VL-CDR3 of a VL comprising the amino acid sequence of SEQ ID NO:20.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:32.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:36.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:40.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:28.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:48; and a VL-CDR1, a VL-CDR2, and a VL-CDR3 of a VL comprising the amino acid sequence of SEQ ID NO:20.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:32.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:36.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:40.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:28.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:52; and a VL-CDR1, a VL-CDR2, and a VL-CDR3 of a VL comprising the amino acid sequence of SEQ ID NO:20.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:32.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:36.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:40.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:28.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:20.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:32.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:36.

In one embodiment, provided is a method of treating tauopathy in a subject, comprising administering to the subject an effective amount of an antibody or antigen binding fragment thereof, wherein the antibody or antigen binding fragment thereof comprises: a VH-CDR1, a VH-CDR2, and a VH-CDR3 of a VH comprising the amino acid sequence of SEQ ID NO:24; and a VL-CDR1, a VL-CDR2, and a VL-CDR3 of a VL comprising the amino acid sequence of SEQ ID NO:40.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:44, and a VL having the amino acid sequence of SEQ ID NO:32.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:44, and a VL having the amino acid sequence of SEQ ID NO:36.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:44, and a VL having the amino acid sequence of SEQ ID NO:40.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:44, and a VL having the amino acid sequence of SEQ ID NO:28.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:44, and a VL having the amino acid sequence of SEQ ID NO:20.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:48, and a VL having the amino acid sequence of SEQ ID NO:32.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:48, and a VL having the amino acid sequence of SEQ ID NO:36.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:48, and a VL having the amino acid sequence of SEQ ID NO:40.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:48, and a VL having the amino acid sequence of SEQ ID NO:28.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:48, and a VL having the amino acid sequence of SEQ ID NO:20.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:52, and a VL having the amino acid sequence of SEQ ID NO:32.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:52, and a VL having the amino acid sequence of SEQ ID NO:36.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:52, and a VL having the amino acid sequence of SEQ ID NO:40.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:52, and a VL having the amino acid sequence of SEQ ID NO:28.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:52, and a VL having the amino acid sequence of SEQ ID NO:20.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:56, and a VL having the amino acid sequence of SEQ ID NO:32.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:56, and a VL having the amino acid sequence of SEQ ID NO:36.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:56, and a VL having the amino acid sequence of SEQ ID NO:40.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:56, and a VL having the amino acid sequence of SEQ ID NO:28.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:56, and a VL having the amino acid sequence of SEQ ID NO:20.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:24, and a VL having the amino acid sequence of SEQ ID NO:32.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:24, and a VL having the amino acid sequence of SEQ ID NO:36.

In yet another embodiment, provided is a method of treating tauopathy in a subject, comprising administering to the subject an effective amount of an antibody or antigen binding fragment thereof, wherein the antibody or antigen binding fragment thereof comprises: a VH having the amino acid sequence of SEQ ID NO:24, and a VL having the amino acid sequence of SEQ ID NO:40.

In still another embodiment, provided is a method of treating tauopathy in a subject, comprising administering to the subject an effective amount of an antibody or antigen binding fragment thereof, wherein the antibody or antigen binding fragment thereof comprises: a light chain comprising the amino acid sequence of SEQ ID NO:71 and a heavy chain comprising the amino acid sequence of SEQ ID NO:72.

In still another embodiment, provided is a method of treating tauopathy in a subject, comprising administering to the subject an effective amount of an antibody or antigen binding fragment thereof, wherein the antibody or antigen binding fragment thereof comprises: a light chain comprising the amino acid sequence of SEQ ID NO:73 and a heavy chain comprising the amino acid sequence of SEQ ID NO:74.

In still another embodiment, provided is a method of treating tauopathy in a subject, comprising administering to the subject an effective amount of an antibody or antigen binding fragment thereof, wherein the antibody or antigen binding fragment thereof comprises: a light chain comprising the amino acid sequence of SEQ ID NO:75 and a heavy chain comprising the amino acid sequence of SEQ ID NO:76.

In some embodiments, the method further comprises administering to the subject an additional agent.

In particular embodiments, the additional agent is an agent effective to treat the same or different disorder as the anti-tau-pS413 antibodies or antigen-binding fragments thereof disclosed herein are being used to treat. In some embodiments, the additional agent is an agent effective to mitigate one or more side effects of the anti-tau-pS413 antibodies or antigen-binding fragments thereof disclosed herein. Exemplary additional agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide for immunization, phosphodiesterase inhibitors, serotonin receptor antagonists, anti-amyloid beta peptide antibodies, growth hormone, neurotrophic factor, brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, stem cell factor (SCF), or a different anti-tau antibody.

Such combination therapies noted above encompass combined administration (where two or more agents are included in the same or separate formulations), and separate administration, in which case, administration of the anti-tau-pS413 antibody or antigen binding fragment thereof can occur prior to, simultaneously, and/or following, administration of the additional agent and/or adjuvant. The anti-tau-pS413 antibodies or antigen-binding fragments thereof disclosed herein can also be used in combination with other interventional therapies such as, but not limited to, radiation therapy, behavioral therapy, or other therapies known in the art and appropriate for the neurological disorder to be treated or prevented, for example, regenerative medicine approaches that use biotechnologies including gene therapy, gene-modified cell therapy, cell therapy and tissue engineering to restore or establish normal brain function.

Anti-tau-pS413 antibodies or fragments thereof may also be useful in diagnostic assays for tau-pS413, e.g., detecting its existence in specific neuron cells, brain tissues, CSF, or interstitial fluid (ISF). Such diagnostic methods may be useful in various disease diagnoses or monitoring progress of the disease.

For example, particular embodiments include ELISA assays incorporating the use of an anti-tau-pS413 antibody or antigen binding fragment thereof disclosed herein.

An exemplary method comprises the following steps:

(a) coat a substrate (e.g., surface of a microtiter plate well, e.g., a plastic plate) with a first antibody or antigen binding fragment thereof;

(b) apply a sample to be tested for the presence of tau-pS413 to the substrate;

(c) wash the plate, so that unbound material in the sample is removed;

(d) apply a detectably labeled second antibody (e.g., enzyme-linked antibody);

(e) wash the substrate, so that the unbound labeled second antibody is removed;

(f) if the labeled second antibody is enzyme linked, apply a chemical which is converted by the enzyme into a fluorescent signal; and (g) detect the presence of the labeled second antibody.

The anti-tau-pS413 antibodies described herein can be the first antibody or the second antibody, or both the first and the second antibodies in the above exemplary method. In one embodiment, the anti-tau-pS413 antibody described herein is the first antibody, and the second antibody is a different antibody that is specific to tau or phosphorylated tau. In another embodiment, the anti-tau-pS413 antibody described herein is the second antibody, and the first antibody is a different that is specific to tau or phosphorylated tau.

In a further embodiment, the labeled anti-tau-pS413 antibody is labeled with peroxidase which reacts with ABTS (e.g., 2,2'-azino-bis(3-ethylbenzothiazoline-6-sulphonic acid)) or 3,3',5,5'-tetramethylbenzidine to produce a color change which is detectable. Alternatively, the labeled anti-tau-pS413 antibody is labeled with a detectable radioisotope (e.g., $^3$H) which can be detected by scintillation counter in the presence of a scintillant.

An anti-tau-pS413 antibody described herein may be used in a Western blot or immune-protein blot procedure.

An exemplary method comprises the following steps:

(1) contacting a membrane or other solid substrate to be tested for the presence of tau-pS413 or a fragment thereof with an anti-tau-pS413 antibody or fragment described herein;

(2) washing the membrane one or more times to remove unbound anti-tau-pS413 antibody or fragment and other unbound substances; and (3) detecting the bound anti-tau-pS413 antibody or fragment.

Such a membrane may take the form of a nitrocellulose or vinyl-based (e.g., polyvinylidene fluoride (PVDF)) membrane to which proteins to be tested for the presence of tau-pS413 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the anti-tau-pS413 antibody or fragment, the membrane is optionally blocked, e.g., with non-fat dry milk or the like so as to block non-specific protein binding sites on the membrane.

Detection of the bound antibody or fragment may be by binding the antibody or fragment with a secondary antibody (an anti-immunoglobulin antibody) which is detectably labeled and, then, detecting the presence of the secondary antibody.

The anti-tau-pS413 antibodies and antigen binding fragments thereof disclosed herein may also be used for immunohistochemistry. Such a method forms part of the present disclosure and comprises, e.g., (1) contacting a cell or tissue to be tested for the presence of tau-pS413 with an anti-tau-pS413 antibody or antigen binding fragment thereof described herein; and (2) detecting the anti-tau-pS413 antibody or antigen binding fragment thereof on or in the cell or in the tissue. If the anti-tau-pS413 antibody or fragment itself is detectably labeled, it can be detected directly. Alternatively, the anti-tau-pS413 antibody or fragment may be bound by a detectably labeled secondary antibody which is detected.

The anti-tau-pS413 antibodies and antigen binding fragments thereof disclosed herein may also be used for in vivo imaging. Such a method may include injection of a radiolabeled anti-tau-pS413 antibodies or antigen-binding fragment thereof into the body of a patient to be tested for the presence of tauopathy associated with the presence of tau-pS413 followed by nuclear imaging of the body of the patient to detect the presence of the labeled anti-tau-pS413 antibody or fragment, e.g., at loci comprising a high concentration of the anti-tau-pS413 antibody or fragment which are bound to tau-pS413 in the brain.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) *International Rev. Neurobiol.* 67:385-440).

Thus, in additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein to diagnose tauopathy in a subject.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein to monitor progress of tauopathy in a subject.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for the diagnosis of tauopathy in a subject.

In yet additional embodiments, provided is the use of an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for the monitor of progress of tauopathy in a subject.

In yet additional embodiments, provided is an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for use in a method for diagnosing tauopathy in a subject.

In yet additional embodiments, provided is an antibody (e.g., various isotypes of V1-AFM, V2-AFM, V3-AFM, V4-AFM, V5-AFM, V6-AFM, V7-AFM, or V8-AFM) or antigen binding fragment thereof as disclosed herein for use in a method for monitoring progress of tauopathy in a subject.

In some embodiments, the method of diagnosing tauopathy in a subject comprises administering to the subject an effective amount of the antibodies (e.g., various isotypes of V1-AFM, V2-AFM, V3-AFM, V4-AFM, V5-AFM, V6-AFM, V7-AFM, or V8-AFM) or antigen binding fragments thereof described herein; and imaging the brain of the subject.

In other embodiments, the method of diagnosing tauopathy in a subject comprises obtaining a sample of CSF or ISF from a subject; running an immunodiagnostic assay (e.g., ELISA) with the antibodies (e.g., various isotypes of V1-AFM, V2-AFM, V3-AFM, V4-AFM, V5-AFM, V6-AFM, V7-AFM, or V8-AFM) or antigen binding fragments thereof described herein; and determining whether the subject has tauopathy.

In certain embodiments, the method of monitoring progress of tauopathy in a subject comprises administering to the subject an effective amount of the antibodies (e.g., various isotypes of V1-AFM, V2-AFM, V3-AFM, V4-AFM, V5-AFM, V6-AFM, V7-AFM, or V8-AFM) or antigen binding fragments thereof described herein; and imaging the brain of the subject.

In other embodiments, the method of monitoring progress of tauopathy in a subject comprises obtaining a sample of CSF or ISF from a subject; running an immunodiagnostic assay (e.g., ELISA) with the antibodies (e.g., various isotypes of V1-AFM, V2-AFM, V3-AFM, V4-AFM, V5-AFM, V6-AFM, V7-AFM, or V8-AFM) or antigen binding fragments thereof described herein; and determining progress of tauopathy in the subject.

In some embodiments of the various methods and uses described herein, the tauopathy is a neurodegenerative disease, including but not limited to Alzheimer's disease (AD), corticobasal degeneration (CBD) or corticobasal syndrome (CBS), progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), or frontotemporal lobar degeneration with tau pathology (FTLD-tau). In one embodiment, the tauopathy is AD. In another embodiment, the tauopathy is CBD. In yet another embodiment, the tauopathy is progressive supranuclear palsy. In still another embodiment, the tauopathy is Pick's disease. In one embodiment, the tauopathy is argyrophilic grain dementia. In another embodiment, the tauopathy is MSTD. In yet another embodiment, the tauopathy is FTDP-17. In still another embodiment, the tauopathy is dementia with neurofibrillary tangles. In one embodiment, the tauopathy is DNTC. In another embodiment, the tauopathy is WMT-GGI. In yet another embodiment, the tauopathy is FTLD-tau.

In other embodiments of the various methods and uses described herein, the tauopathy is a non-neurodegenerative disease, including but not limited to infectious diseases, such as Economo's encephalitis sequela and subacute sclerosing panencephalitis, and trauma-induced conditions, such as boxer's encephalopathy. In one embodiment, the tauopathy is Economo's encephalitis sequela. In another embodiment, the tauopathy is subacute sclerosing panencephalitis. In yet another embodiment, the tauopathy is boxer's encephalopathy.

Nucleic Acids, Expression Vectors, Cells, and Methods of Making Anti-Tau-pS413 Antibodies or Antigen Binding Fragments Thereof Also provided herein are isolated nucleic acids and vectors comprising polynucleotide sequences encoding such high affinity antibodies (e.g., various isotypes of V1-AFM, V2-AFM, V3-AFM, V4-AFM, V5-AFM, V6-AFM, V7-AFM, or V8-AFM) disclosed herein or antigen binding fragments thereof, cells (e.g., host cells) comprising such isolated nucleic acids or vectors, and methods of making such high affinity antibodies (e.g., various isotypes of V1-AFM, V2-AFM, V3-AFM, V4-AFM, V5-AFM, V6-AFM, V7-AFM, or V8-AFM) or antigen binding fragments thereof.

In one aspect, provided is an isolated nucleic acid encoding various polypeptides disclosed herein.

In certain embodiments, the isolated nucleic acid encodes the VH (e.g., SEQ ID NO:44, 48, 52, 56, or 24) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein. In some embodiments, the isolated nucleic acid encodes the VL (e.g., SEQ ID NO:32, 36, 40, 28, or 20) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein. In other embodiments, the isolated nucleic acid encodes the VH (e.g., SEQ ID NO:44, 48, 52, 56, or 24) and the VL (e.g., SEQ ID NO:32, 36, 40, 28, or 20) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein.

In certain embodiments, the isolated nucleic acid encodes the heavy chain (e.g., SEQ ID NO:72, 74 or 76) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein. In some embodiments, the isolated nucleic acid encodes the light chain (e.g., SEQ ID NO:71, 73, or 75) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein. In other embodiments, the isolated nucleic acid encodes the heavy chain (e.g., SEQ ID NO:72, 74 or 76) and the light chain (e.g., SEQ ID NO:71, 73, or 75) of various antibodies (e.g., various isotypes of V1-AFM, V2-AFM, V3-AFM, V4-AFM, V5-AFM, V6-AFM, V7-AFM, or V8-AFM) or antigen binding fragments thereof disclosed herein.

In one embodiment, the isolated nucleic acid encodes a VH domain comprising the VH-CDR1, VH-CDR2 and VH-CDR3 as disclosed in TABLE 5.

In another embodiment, the isolated nucleic acid encodes a VL domain comprising the VL-CDR1, VL-CDR2 and VL-CDR3 as disclosed in TABLE 6.

In yet another embodiment, the isolated nucleic acid encodes a VH domain comprising the VH-CDR1, VH-CDR2 and VH-CDR3 as disclosed in TABLE 5 and a VL domain comprising the VL-CDR1, VL-CDR2 and VL-CDR3 as disclosed in TABLE 6.

In a specific embodiment, the isolated nucleic acid comprises a nucleotide sequence as set forth in SEQ ID NO:107. In another specific embodiment, the isolated nucleic acid comprises a nucleotide sequence as set forth in SEQ ID NO:108.

In still another embodiment, the nucleic acids further encode a signal sequence.

In another aspect, provided is an expression vector comprising one or more of the various isolated nucleic acids disclosed herein, wherein the nucleic acid(s) is operably linked to control sequences that are recognized by a host cell when the host cell is transfected with the expression vector.

In yet another aspect, provided is host cell comprising one or more of the various isolated nucleic acids or the various expression vectors disclosed herein. In some embodiments, the host cell comprises one or more of the various isolated nucleic acids disclosed herein. In other embodiments, the host cell comprises one or more of the various expression vectors disclosed herein.

In still another aspect, provided are methods of making the antibody (e.g., various isotypes of V1-AFM, V2-AFM, V3-AFM, V4-AFM, V5-AFM, V6-AFM, V7-AFM, or V8-AFM) or antigen binding fragment thereof disclosed herein, comprising: culturing a host cell comprising an expression vector encoding the antibody or antigen binding fragment thereof in culture medium under conditions wherein the antibody or antigen binding fragment thereof is expressed.

Also provided are methods of making the antibody (e.g., various isotypes of V1-AFM, V2-AFM, V3-AFM, V4-AFM, V5-AFM, V6-AFM, V7-AFM, or V8-AFM) or antigen binding fragment thereof disclosed herein, comprising: expressing an expression vector that comprises one or more isolated nucleic acid(s) disclosed herein under conditions wherein the antibody or antigen binding fragment thereof is expressed.

Further provided are methods of making the antibody (e.g., various isotypes of V1-AFM, V2-AFM, V3-AFM, V4-AFM, V5-AFM, V6-AFM, V7-AFM, or V8-AFM) or antigen binding fragment thereof disclosed herein, comprising: expressing one or more isolated nucleic acid(s) disclosed herein under conditions wherein the antibody or antigen binding fragment thereof is expressed.

In certain embodiments of various methods of making the antibody (e.g., various isotypes of V1-AFM, V2-AFM, V3-AFM, V4-AFM, V5-AFM, V6-AFM, V7-AFM, or V8-AFM) or antigen binding fragment thereof disclosed herein, the method further comprises isolating the antigen or antigen binding fragment thereof from the host cell or culture medium, or in vitro expression system.

Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Other cell lines that may be used are insect cell lines, such as Sf9 cells, amphibian cells, bacterial cells, plant cells and fungal cells. Various modifications can be introduced into the genome of these cell lines (e.g., glutamine synthetase knockout, auxotrophic mutations, etc.) to achieve desired properties of the host cells and/or desired properties of the expressed antibodies or antigen binding fragments thereof.

When recombinant expression vectors encoding the heavy chain or antigen binding fragment thereof and/or the light chain or antigen binding fragment thereof are introduced into host cells, the antibody or antigen binding fragment thereof is produced by culturing the host cells for a period of time sufficient to allow for expression of the antibody or antigen binding fragment thereof in the host cells or, more preferably, secretion of the antibody or antigen binding fragment thereof into the culture medium in which the host cells are grown.

Antibodies can be recovered from the culture medium using standard protein purification methods.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

Pharmaceutical Compositions and Administration

In another aspect, provided is a composition comprising the anti-tau-pS413 antibodies (e.g., various isotypes of V1-AFM, V2-AFM, V3-AFM, V4-AFM, V5-AFM, V6-AFM, V7-AFM, or V8-AFM) or antigen binding fragments thereof described herein and a pharmaceutically acceptable carrier.

In some embodiments, the composition further comprises an additional agent.

In particular embodiments, the additional agent is an agent effective to treat the same or different disorder as the anti-tau-pS413 antibodies or antigen-binding fragments thereof disclosed herein are being used to treat. In some embodiments, the additional agent is an agent effective to relieve side effects of the anti-tau-pS413 antibodies or antigen-binding fragments thereof disclosed herein. Exemplary additional agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide for immunization, phosphodiesterase inhibitors, serotonin receptor antagonists, anti-amyloid beta peptide antibodies, growth hormone, neurotrophic factor, brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, stem cell factor (SCF), or a different anti-tau antibody.

To prepare pharmaceutical or sterile compositions of the anti-tau-pS413 antibody or antigen binding fragment thereof described herein, the antibody or antigen binding fragment thereof is admixed with a pharmaceutically acceptable carrier or excipient. See, e.g., Remington's Pharmaceutical Sciences and U.S. Pharmacopeia: National Formulary, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a composition comprising an antibody or antibody fragment disclosed herein is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral, intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-tau-pS413 antibody or antigen binding fragment thereof can be administered by an invasive route such as by injection (see above). In further embodiments of the invention, the anti-tau-pS413 antibody or antigen binding fragment thereof, or pharmaceutical composition thereof, is administered intravenously, subcutaneously, intrathecally, intramuscularly, or intracerebrally. In one specific embodiment, the anti-tau-pS413 antibody or antigen binding fragment thereof, or pharmaceutical composition thereof, is administered intravenously. In another specific embodiment, the anti-tau-pS413 antibody or antigen binding fragment thereof, or pharmaceutical composition thereof, is administered subcutaneously. In yet another specific embodiment, the anti-tau-pS413 antibody or antigen binding fragment thereof, or pharmaceutical composition thereof, is administered intrathecally. In still another specific embodiment, the anti-tau-pS413 antibody or antigen binding fragment thereof, or pharmaceutical composition thereof, is administered intramuscularly. In still another specific embodiment, the anti-tau-pS413 antibody or antigen binding fragment thereof, or pharmaceutical composition thereof, is administered intracerebrally.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered by infusion.

The administration regimen depends on several factors, including the serum or tissue turnover rate of the therapeutic antibody, the ratio of the therapeutic antibody that crosses the blood-brain barrier, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348: 24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

As previously described, the anti-tau-pS413 antibodies or antigen binding fragments thereof may be coadministered with one or more additional agents. The antibody may be linked to the agent (as an immunocomplex) or can be administered separately from the agent (fixed dose). In the latter case (separate administration), the antibody can be administered before, after, or concurrently with the agent or can be co-administered with other known therapies.

Kits

Also provided herein are kits comprising an antibody (e.g., an anti-tau-pS413 antibody) provided herein, or a composition (e.g., a pharmaceutical composition) thereof, packaged into suitable packaging material. A kit optionally includes a label or packaging insert including a description of the components or instructions for use in vitro, in vivo, or ex vivo, of the components therein.

The term "packaging material" refers to a physical structure housing the components of the kit. The packaging material can maintain the components sterilely, and can be made of material commonly used for such purposes (e.g., paper, corrugated fiber, glass, plastic, foil, ampoules, vials, tubes, etc.).

Kits provided herein can include labels or inserts. Labels or inserts include "printed matter," e.g., paper or cardboard, separate or affixed to a component, a kit or packing material (e.g., a box), or attached to, for example, an ampoule, tube, or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media, or memory type cards. Labels or inserts can include information identifying manufacturer information, lot numbers, manufacturer location, and date.

Kits provided herein can additionally include other components. Each component of the kit can be enclosed within an individual container, and all of the various containers can be within a single package. Kits can also be designed for cold storage. A kit can further be designed to contain antibodies provided herein, or cells that contain nucleic acids encoding the antibodies provided herein. The cells in the kit can be maintained under appropriate storage conditions until ready to use.

General Methods

Standard methods in molecular biology are described in Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992)*J Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, $2^{nd}$ ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput.*

*Methods Programs Biomed.* 68:177-181; von Heijne (1983) *Eur. J. Biochem.* 133:17-21; von Heijne (1986) *Nucleic Acids Res.* 14:4683-4690).

Example 1. Affinity Maturation and Point Mutation

HmzTa1505-hIgG4-S228P is a humanized antibody that was generated from the mouse parental antibody Ta1505-mIgG2a, the details of which are documented in WO 2018/254390.

Affinity maturation of HmzTa1505-hIgG4-S228P was performed via yeast display screening of a structure-based designed affinity maturation library. The library design was guided by the apo Ta1505 Fab crystal structure with the introduction of 79:7:7:7 non-equimolar (doped) partially randomized mutations at the DNA level to solvent-exposed heavy chain and light chain CDR residues. Three initial libraries were created and screened; the libraries consisted of mutations in CDR-H1/H2 (9 residues total), CDR-H3 (8 residues total), and CDR-VL (12 residues total). FACS sorting of yeast cells labeled with biotinylated tau-pS413 peptide and anti-kappa light chain was used to isolate leads with increased affinity while maintaining phospho-specificity. FACS sorted outputs from the initial libraries were later combined to generate a final combined VH/VL yeast display library for synergistic improvement and screened in the same manner. Thirty hits from the combined library were reformatted to hIgG4-S228P isotype and produced recombinantly, followed by Biacore and protein analytics. One of the top hits was V1-AFM-hIgG4-S228P, which showed a 10-fold improvement in monovalent affinity and >40× improvement in binding to phosphorylated Tau in AD patient cerebrospinal fluid (CSF), compared to HmzTa1505-hIgG4-S228P (see TABLE 8).

VH or VL from the top hits of affinity maturation were switched and matched with VL or VH of another top hit to generate more antibody variants.

An additional mutation (K54E or K54D) in various VHs was identified via structure-based design with the goal of identifying mutations that lowered the isoelectric point (pI) while maintaining or improving the affinity. The designs were guided by computational saturation mutagenesis and a co-crystal of Ta1505 Fab bound to a tau-pS413 peptide.

Figure 6:
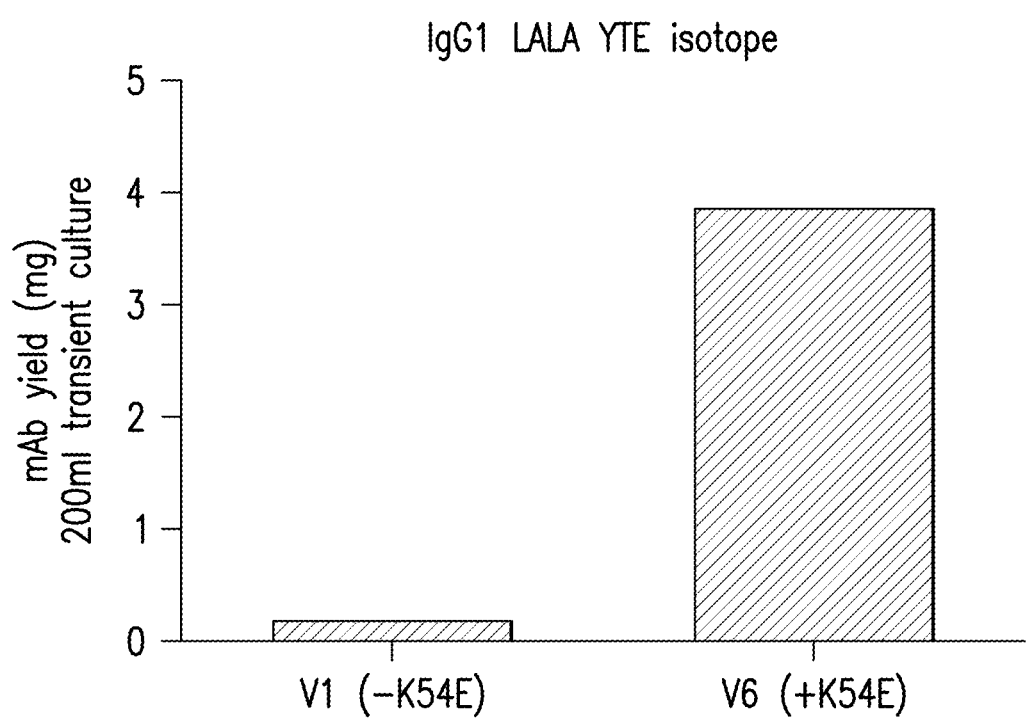
FIG. 6 shows that V6-AFM-hIgG1-LALA-YTE, which includes a K54E mutation in the VH, had improved production of the antibody molecule compared to V1-AFM-hIgG1-LALA-YTE, which does not include the K54E mutation in its VH.

For example, addition of K54E to the VH of V1-AFM generated V6-AFM. V6-AFM-hIgG1-LALA-YTE showed lower pI (8.54) compared to V1-AFM-hIgG1-LALA-YTE (pI=8.87). Compared to V1-AFM, V6-AFM exhibited improved monovalent affinity to tau-pS413 on all 3 isotypes tested (hIgG1-LALA, hIgG1-LALA-YTE, and hIgG4-S228P) (see TABLE 8). Surprisingly, V6-AFM even exhibited improved production of the antibody molecules on IgG1-LALA isotype (data not shown) and IgG1-LALA-YTE isotype (FIG. 6), compared with V1-AFM.

In another embodiment, K54E mutation in the VH of V2-AFM was replaced with K54D. Compared with a reference antibody (pI=8.28) having K at position 54 of the VH of V2-AFM, both E and D mutations at position 54 reduced the pI to 7.58. In addition, K54E and K54D mutations increased the KD of the reference antibody by 1.9- and 1.4-fold, respectively.

Finally, different heavy chain isotype constant regions (e.g., IgG1, IgG1-LALA, IgG1-LALA-YTE, IgG4, IgG4-S228P) were added to the VH of various exemplary antibodies.

Exemplary antibodies generated are described in TABLE 4. Corresponding SEQ ID NOs for various VH and VH-CDRs (defined by the Kabat numbering system) are listed in TABLE 5 and SEQ ID NOs for various VL and VL-CDRs (defined by the Kabat numbering system) are listed in TABLE 6. To illustrate how different CDR numbering systems affect the sequences of CDRs in an antibody, CDRs of V8-AFM defined by commonly used numbering systems are listed in TABLE 7.

TABLE 4

Exemplary antibodies

| Antibody Name | Heavy Chain Isotype | VH | VL | Description (heavy chain/light chain) |
|---|---|---|---|---|
| Ta1505-mIgG2a | mIgG2a | Ta1505-VH | Ta1505-VL | Mouse × [MAPT_H] mAb (Ta1505) IgG2a/Kappa |
| V0-hIgG1 | hIgG1 | VH11 | VL46 | Humanized × [MAPT_H] mAb (Ta1505 VL46/VH11) IgG1/Kappa (CX) |
| V0-hIgG4-S228P | hIgG4 (S228P) | VH11 | VL46 | Humanized × [MAPT_H] mAb (Ta1505 VL46/VH11) IgG4 S228P/Kappa (CX) |
| HmzTa1505-hIgG4-S228P | hIgG4 (S228P) | VH11 | VL46_G34A_S28N | Humanized × [MAPT_H] mAb (Ta1505-VL46_G34A_S28N/VH11) IgG4 S228P/Kappa (CX) |
| V1-AFM-hIgG4-S228P | hIgG4 (S228P) | VH11_A59V_VD68G | VL46_G34A_S28N_Q27H_S32R_H98Y | Humanized Modified × [MAPT_H] mAb (Ta1505-VH11_A59V_D68G/ VL46_G34A_S28N_Q27H_S32R_H98Y) IgG4 S228P/Kappa (CX) |
| V1-AFM-hIgG1-LALA | hIgG1 (LALA) | VH11_A59V_VD68G | VL46_G34A_S28N_Q27H_S32R_H98Y | Humanized × [MAPT_H] mAb (Ta1505-VH11_A59V_D68G/ VL46_G34A_S28N_Q27H_S32R_H98Y) IgG1 L234A L235A/Kappa (CX) |
| V1-AFM-hIgG1-LALA-YTE | hIgG1 (LALA YTE) | VH11_A59V_VD68G | VL46_G34A_S28N_Q27H_S32R_H98Y | Humanized × [MAPT_H] mAb (Ta1505-VH11_A59V_D68G/ VL46_G34A_S28N_Q27H_S32R_H98Y) IgG1 L234A L235A YTE/Kappa (CX) |

TABLE 4-continued

Exemplary antibodies

| Antibody Name | Heavy Chain Isotype | VH | VL | Description (heavy chain/light chain) |
|---|---|---|---|---|
| V2-hIgG1-LALA | hIgG1 (LALA) | VH11_D68G_K54E | VL46_G34A_S28N_Q27H_S32R_H98Y | Humanized Modified × [MAPT_H] mAb (Ta1505-VH11_D68G_K54E/ VL46_G34A_S28N_Q27H_S32R_H98Y) IgG1 L234A L235A/Kappa (CX) |
| V2-hIgG1-LALA-YTE | hIgG1 (LALA YTE) | VH11_D68G_K54E | VL46_G34A_S28N_Q27H_S32R_H98Y | Humanized Modified × [MAPT_H] mAb (Ta1505-VH11_D68G_K54E/ VL46_G34A_S28N_Q27H_S32R_H98Y) IgG1 L234A L235A YTE/Kappa (CX) |
| V3-AFM-hIgG4-S228P | hIgG4 (S228P) | VH11_D68G | VL46_G34A_S28K_S32R_H98Y | Humanized × [MAPT_H] mAb (Ta1505-VH11_D68G/Ta1505-VL46_G34A_S28K_S32R_H98Y) IgG4 S228P/Kappa (CX) |
| V4-AFM-hIgG1-LALA | hIgG1 (LALA) | VH11_D68G_K54E | VL46_G34A_S28K_S32R_H98Y | Humanized Modified × [MAPT_H] mAb (Ta1505-VH11_D68G_K54E/ VL46_G34A_S28K_S32R_H98Y) IgG1 L234A L235A/Kappa (CX) |
| V4-AFM-hIgG1-LALA-YTE | hIgG1 (LALA YTE) | VH11_D68G_K54E | VL46_G34A_S28K_S32R_H98Y | Humanized Modified × [MAPT_H] mAb (Ta1505-VH11_D68G_K54E/ VL46_G34A_S28K_S32R_H98Y) IgG1 L234A L235A YTE/Kappa (CX) |
| V5-AFM-hIgG4-S228P | hIgG4 (S228P) | VH11_A59V_VD68G | VL46_G34A_S28K_S32R_H98Y | Humanized × [MAPT_H] mAb (Ta1505-VH11_A59V_D68G/ VL46_G34A_S28K_S32R_H98Y) IgG4 S228P/Kappa (CX) |
| V6-AFM-hIgG4-S228P | hIgG4 (S228P) | VH11_A59V_D68G_K54E | VL46_G34A_S28N_Q27H_S32R_H98Y | Humanized Modified × [MAPT_H] mAb (Ta1505-VH11_A59V_D68G_K54E/ VL46_G34A_S28N_Q27H_S32R_H98Y) IgG4 S228P/Kappa (CX) |
| V6-AFM-hIgG1-LALA | hIgG1 (LALA) | VH11_A59V_D68G_K54E | VL46_G34A_S28N_Q27H_S32R_H98Y | Humanized Modified × [MAPT_H] mAb (Ta1505-VH11_A59V_D68G_K54E/ VL46_G34A_S28N_Q27H_S32R_H98Y) IgG1 L234A L235A/Kappa (CX) |
| V6-AFM-hIgG1-LALA-YTE | hIgG1 (LALA YTE) | VH11_A59V_D68G_K54E | VL46_G34A_S28N_Q27H_S32R_H98Y | Humanized Modified × [MAPT_H] mAb (Ta1505-VH11_A59V_D68G_K54E/ VL46_G34A_S28N_Q27H_S32R_H98Y) IgG1 L234A L235A YTE/Kappa (CX) |
| V7-AFM-hIgG4-S228P | hIgG4 (S228P) | VH11 | VL46_G34A_S28N_Q27R_S32R_H98Y | Humanized × [MAPT_H] mAb (Ta1505-VH11/ VL46_G34A_S28N_Q27R_S32R_H98Y) IgG4 S228P/Kappa (CX) |
| V7-AFM-hIgG1-LALA | hIgG1 (LALA) | VH11 | VL46_G34A_S28N_Q27R_S32R_H98Y | Humanized × [MAPT_H] mAb (Ta1505-VH11/ VL46_G34A_S28N_Q27R_S32R_H98Y) IgG1 L234A L235A/Kappa (CX) |
| V7-AFM-hIgG1-LALA-YTE | hIgG1 (LALA YTE) | VH11 | VL46_G34A_S28N_Q27R_S32R_H98Y | Humanized × [MAPT_H] mAb (Ta1505-VH11/ VL46_G34A_S28N_Q27R_S32R_H98Y) IgG1 L234A L235A YTE/Kappa (CX) |
| V8-AFM-hIgG4-S228P | hIgG4 (S228P) | VH11_A59V_D68G_K54E | VL46_G34A_S28K_S32R_H98Y | Humanized Modified × [MAPT_H] mAb (Ta1505-VH11_A59V_D68G_K54E/ VL46_G34A_S28K_S32R_H98Y) IgG4 S228P/Kappa (CX) |
| V8-AFM-hIgG1-LALA | hIgG1 (LALA) | VH11_A59V_D68G_K54E | VL46_G34A_S28K_S32R_H98Y | Humanized Modified × [MAPT_H] mAb (Ta1505-VH11_A59V_D68G_K54E/ VL46_G34A_S28K_S32R_H98Y) IgG1 L234A L235A/Kappa (CX) |
| V8-AFM-hIgG1-LALA-YTE | hIgG1 (LALA YTE) | VH11_A59V_D68G_K54E | VL46_G34A_S28K_S32R_H98Y | Humanized Modified × [MAPT_H] mAb (Ta1505-VH11_A59V_D68G_K54E/ VL46_G34A_S28K_S32R_H98Y) IgG1 L234A L235A YTE/Kappa (CX) |

TABLE 5

SEQ ID NOs for VH and VH-CDRs (defined by the Kabat numbering system)

| Heavy chain name | VH-CDR1 | VH-CDR2 | VH-CDR3 | VH |
|---|---|---|---|---|
| VH11_D68G | SEQ ID NO: 41 | SEQ ID NO: 42 | SEQ ID NO: 43 | SEQ ID NO: 44 |
| VH11_A59V_D68G | SEQ ID NO: 45 | SEQ ID NO: 46 | SEQ ID NO: 47 | SEQ ID NO: 48 |
| VH11_D68G_K54E | SEQ ID NO: 49 | SEQ ID NO: 50 | SEQ ID NO: 51 | SEQ ID NO: 52 |
| VH11_A59V_D68G_K54E | SEQ ID NO: 53 | SEQ ID NO: 54 | SEQ ID NO: 55 | SEQ ID NO: 56 |
| VH11 | SEQ ID NO: 21 | SEQ ID NO: 22 | SEQ ID NO: 23 | SEQ ID NO: 24 |

TABLE 6

SEQ ID NOs for VL and VL-CDRs (defined by the Kabat numbering system)

| Light chain name | VL-CDR1 | VL-CDR2 | VL-CDR3 | VL |
|---|---|---|---|---|
| VL46_G34A_S28N_Q27R_S32R_H98Y | SEQ ID NO: 29 | SEQ ID NO: 30 | SEQ ID NO: 31 | SEQ ID NO: 32 |
| VL46_G34A_S28K_S32R_H98Y | SEQ ID NO: 33 | SEQ ID NO: 34 | SEQ ID NO: 35 | SEQ ID NO: 36 |
| VL46_G34A_S28N_Q27H_S32R_H98Y | SEQ ID NO: 37 | SEQ ID NO: 38 | SEQ ID NO: 39 | SEQ ID NO: 40 |
| VL46_G34A_S28N | SEQ ID NO: 25 | SEQ ID NO: 26 | SEQ ID NO: 27 | SEQ ID NO: 28 |
| VL46 | SEQ ID NO: 17 | SEQ ID NO: 18 | SEQ ID NO: 19 | SEQ ID NO: 20 |

TABLE 7

CDR sequences of V8-AFM defined by different numbering systems CDR

| name | Kabat | AbM | Chothia | Contact | IMGT |
|---|---|---|---|---|---|
| VL-CDR1 | RSSQKIVHRNANTYLE (SEQ ID NO: 33) | RSSQKIVHRNANTYLE (SEQ ID NO: 83) | RSSQKIVHRNANTYLE (SEQ ID NO: 89) | VHRNANTYLEWY (SEQ ID NO: 95) | QKIVHRNANTY (SEQ ID NO: 101) |
| VL-CDR2 | TVSNRFS (SEQ ID NO: 34) | TVSNRFS (SEQ ID NO: 84) | TVSNRFS (SEQ ID NO: 90) | LLIYTVSNRF (SEQ ID NO: 96) | TV (SEQ ID NO: 102) |
| VL-CDR3 | FQGSYLPLT (SEQ ID NO: 35) | FQGSYLPLT (SEQ ID NO: 85) | FQGSYLPLT (SEQ ID NO: 91) | FQGSYLPL (SEQ ID NO: 97) | FQGSYLPLT (SEQ ID NO: 103) |
| VH-CDR1 | SFALN (SEQ ID NO: 53) | GFTFSSFALN (SEQ ID NO: 86) | GFTFSSF (SEQ ID NO: 92) | SSFALN (SEQ ID NO: 98) | GFTFSSFA (SEQ ID NO: 104) |
| vH-CDR2 | HIRSETNNYVTFYAASVKG (SEQ ID NO: 54) | HIRSETNNYVTF (SEQ ID NO: 87) | RSETNNYVTF (SEQ ID NO: 93) | WVGHIRSETNNYVTF (SEQ ID NO: 99) | IRSETNNYV (SEQ ID NO: 105) |
| VH-CDR3 | RGPRDSWFGY (SEQ ID NO: 55) | RGPRDSWFGY (SEQ ID NO: 88) | RGPRDSWFGY (SEQ ID NO: 94) | VRRGPRDSWFG (SEQ ID NO: 100) | VRRGPRDSWFGY (SEQ ID NO: 106) |

Sequence alignment among exemplary VHs is shown in FIG. 1A, and sequence alignment among exemplary VLs is shown in FIG. 1B.

Example 2. Determination of Binding Affinity to Tau-pS413 Peptide by Surface Plasmon Resonance (SPR)

SPR assay was used to determine the monovalent binding affinities of mAbs to a tau-pS413 peptide (SEQ ID NO:109). Antibodies were amine coupled to a CMS sensor chip at approximately 1000 RUs each. Binding assays were performed using HBS-EP running buffer containing 3 mM EDTA and 0.05% Tween-20, pH 7.4. Titrating concentrations (200 nM top for HmzTa1505-hIgG4-S228P, 80 nM top for all other mAbs, 6-point, 2.5-fold dilution series and two zeros) of the tau-pS413 peptide were injected over the immobilized mAbs. For each injection, the tau-pS413 peptide was allowed to associate for 180 seconds, followed by dissociation for 900 seconds. Each sample injection was followed by an injection of 20 mM sodium acetate, pH 3.5, for 60 seconds to regenerate the surface for subsequent injection. All assays were run on Biacore T200 and/or 4000 instruments (GE Healthcare) and the data were fit to a 1:1 binding model using Biaevaluation software. Affinity was calculated from association and dissociation rate constants as $K_D = k_{off}/k_{on}$.

All mAbs bound the tau-pS413 peptide (TABLE 8). All affinity matured antibody variants (V1-AFM through V8-AFM) exhibited about 2- to about 30-fold affinity increase compared to HmzTa1505-hIgG4-S228P.

TABLE 8

Binding affinity of exemplary antibodies to tau-pS413 peptide

| Antibody name | KD (M) mean | KD of HmzTa1505-hIgG4-S228P/KD (fold-change) |
| --- | --- | --- |
| Ta1505-mIgG2a | 9.40E−09 | 3.09 |
| V0-hIgG1 | 2.43E−08 | 1.19 |
| V0-hIgG4-S228P | 3.93E−08 | 0.74 |
| HmzTa1505-hIgG4-S228P | 2.90E−08 | 1.00 |
| V1-AFM-hIgG4-S228P | 2.81E−09 | 10.31 |
| V1-AFM-hIgG1-LALA | 1.40E−09 | 20.66 |
| V1-AFM-hIgG1-LALA-YTE | 1.74E−09 | 16.67 |
| V2-AFM-hIgG1-LALA | 1.87E−09 | 15.51 |
| V2-AFM-hIgG1-LALA-YTE | 1.96E−09 | 14.80 |
| V3-AFM-hIgG4-S228P | 1.31E−08 | 2.22 |
| V4-AFM-hIgG1-LALA | 6.83E−09 | 4.25 |
| V4-AFM-hIgG1-LALA-YTE | 3.26E−09 | 8.89 |
| V5-AFM-hIgG4-S228P | 3.57E−09 | 8.12 |
| V6-AFM-hIgG4-S228P | 1.35E−09 | 21.43 |
| V6-AFM-hIgG1-LALA | 1.02E−09 | 28.50 |
| V6-AFM-hIgG1-LALA-YTE | 9.75E−10 | 29.77 |
| V7-AFM-hIgG4-S228P | 4.34E−09 | 6.69 |
| V7-AFM-hIgG1-LALA | 4.36E−09 | 6.65 |
| V7-AFM-hIgG1-LALA-YTE | 3.82E−09 | 7.59 |
| V8-AFM-hIgG4-S228P | 2.26E−09 | 12.81 |
| V8-AFM-hIgG1-LALA | 1.76E−09 | 16.52 |
| V8-AFM-hIgG1-LALA-YTE | 1.92E−09 | 15.13 |

Example 3. The High Affinity Anti-Tau-pS413 Antibodies Bind Specifically to Tau Peptide Phosphorylated at Serine 413

Binding specificity of the high affinity antibodies described herein was assessed with various tau peptides by a peptide-coated ELISA. Plates were coated with 50 μl of 1 μg/ml peptides 69AXY, 70AXY, 74AXY, 84AWK, 25AWF, or 24AWF in PBS for overnight at 4° C. On the next day, the plates were washed 3 times, blocked with 200 μl of superblock for 1 hr at room temperature, then washed 3 times again. Antibodies were diluted at 1:5 serial dilution in ELISA buffer starting from 10 μg/ml. The plates were incubated with 50 μl of serially diluted antibodies at room temperature for 1 hr and washed 3 times. Then the plates were incubated with 50 μl of goat anti-mouse IgG-HRP (Southern Biotech, cat #1030-05) or goat anti-human IgG-HRP (Jackson Immunologics, cat #109-036-0980) diluted 1:3000 in ELISA buffer for 45 minutes at room temperature, washed 5 times, then developed with ABTS for 5 mins at room temperature and read at OD 405 nM.

Figure 2A:
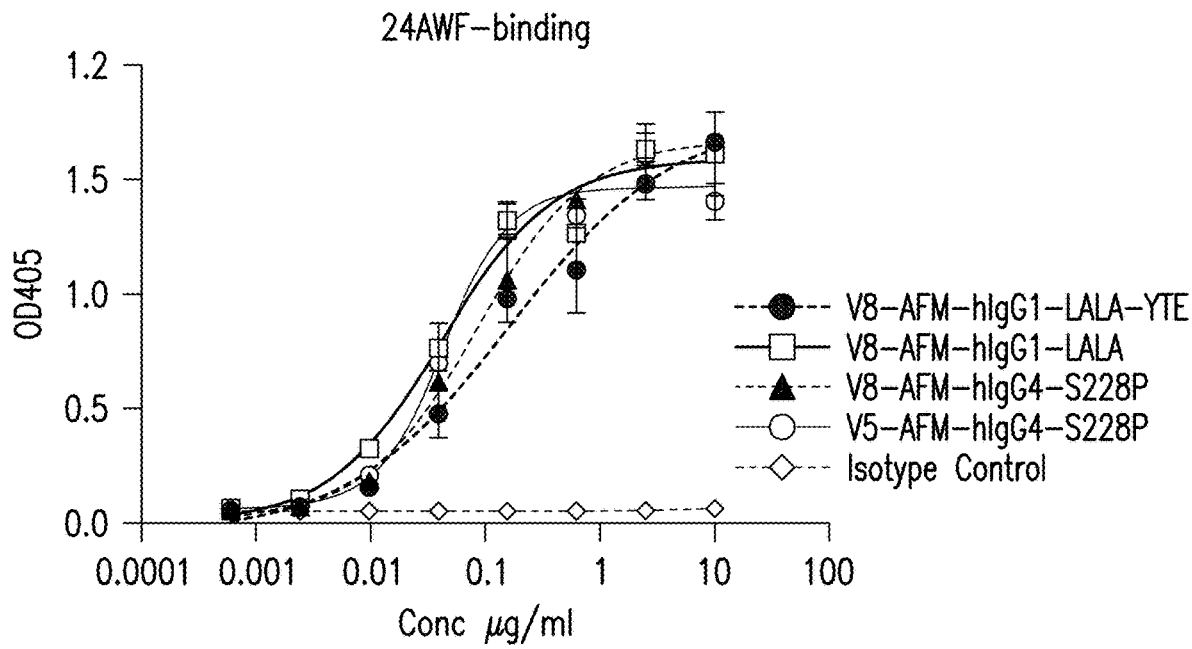
FIGS. 2A-2F demonstrate that exemplary high affinity anti-tau-pS413 antibodies V8-AFM and V5-AFM bind specifically to tau-pS413 peptide. V8-AFM (e.g., V8-AFM-hIgG1-LALA-YTE, V8-AFM-hIgG1-LALA, V8-AFM-hIgG4-S228P) and V5-AFM (e.g., V5-AFM-hIgG4-S228P) bind to a peptide that has phosphorylated serine 413 (FIG. 2A) but do not bind to the same peptide without serine 413 phosphorylated (FIG. 2B) or peptides that are phosphorylated at other positions in the tau protein (FIGS. 2C-2F).
Figure 2B:
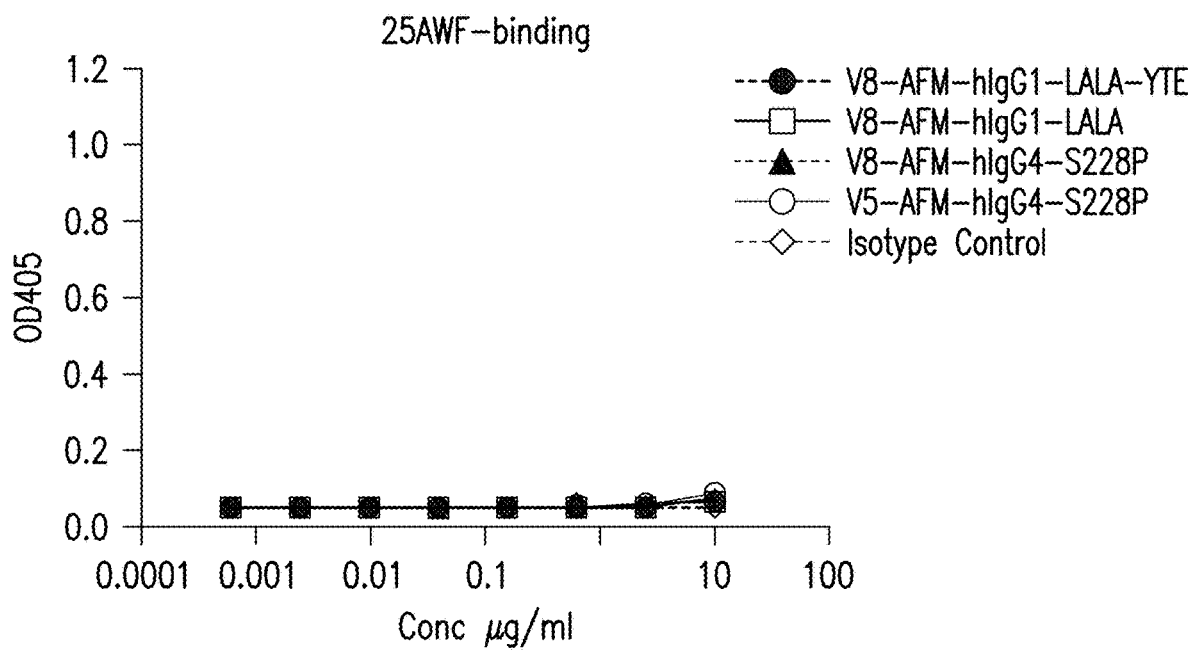
Figure 2C:
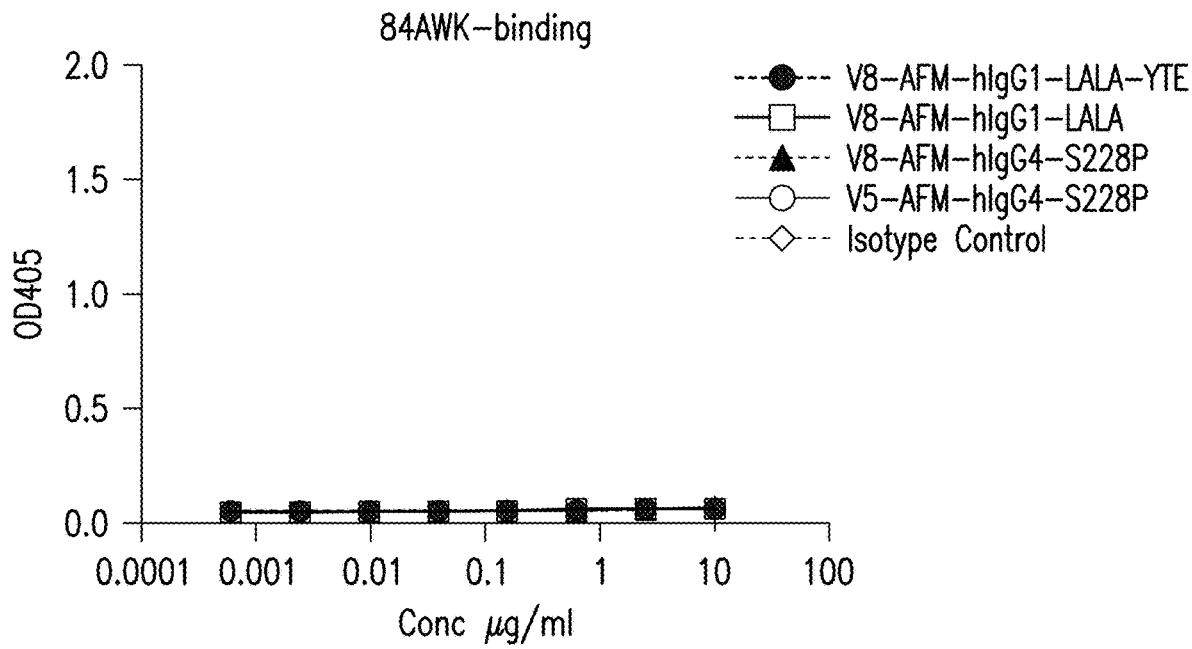
Figure 2D:
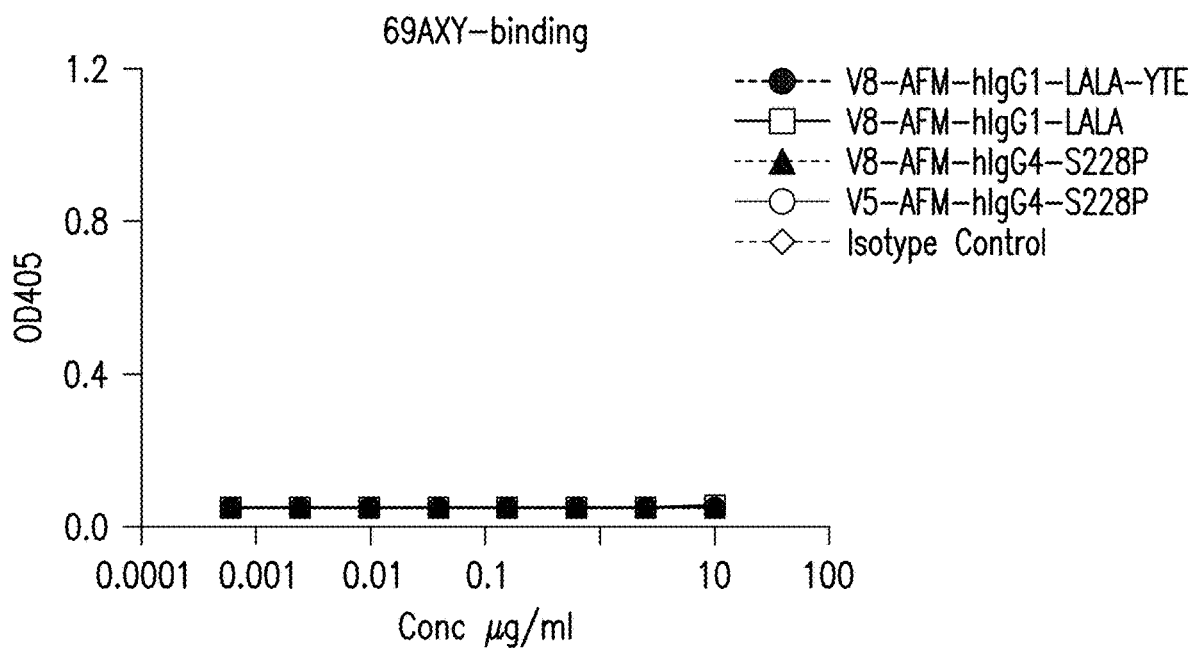
Figure 2E:
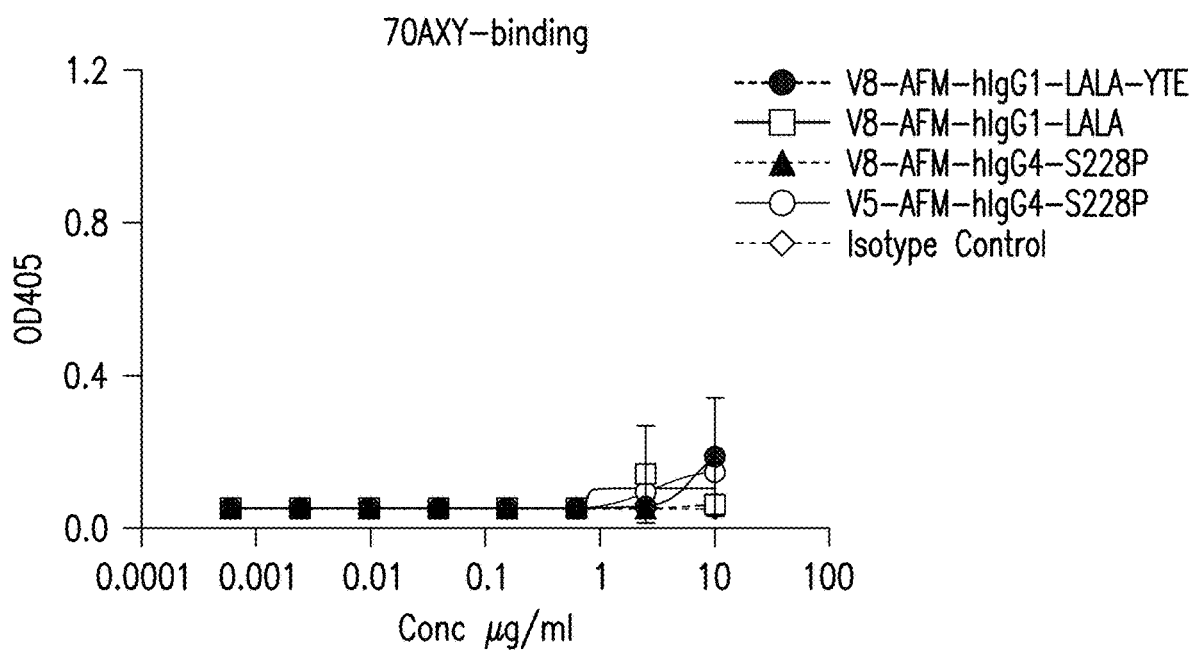
Figure 2F:
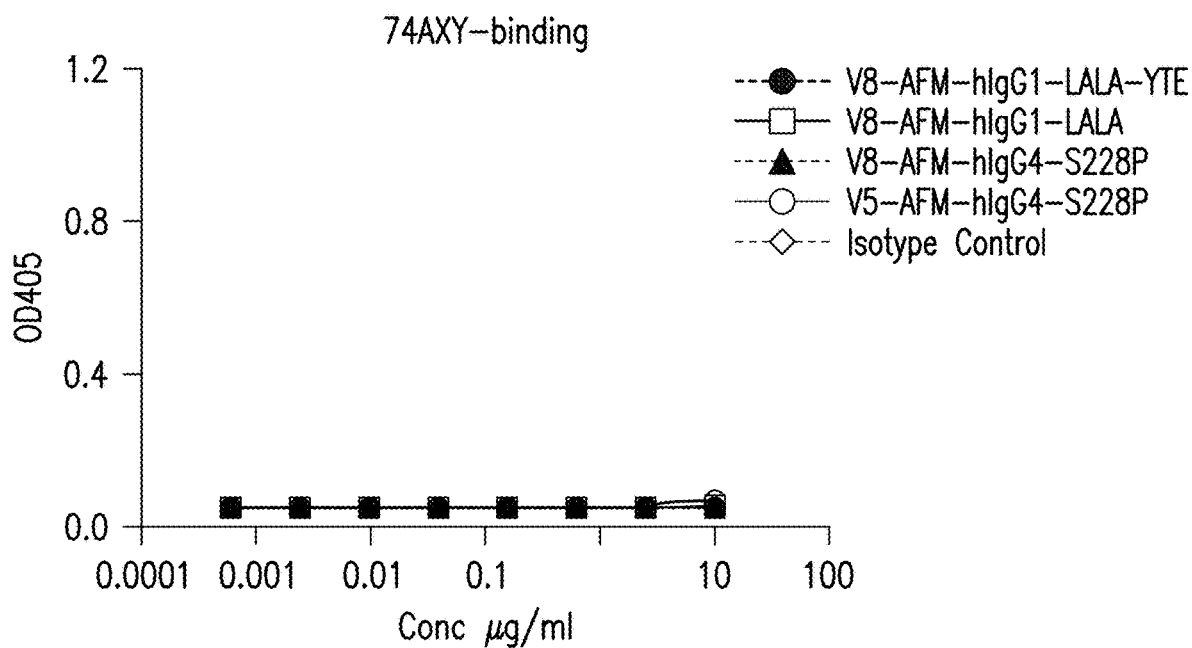

The bindings of exemplary antibodies (V8-AFM-IgG1-LALA, V8-AFM-IgG1-LALA-YTE, V8-AFM-IgG4-S228P, V5-AFM-IgG4-S228P) are shown in FIGS. 2A-2F. For example, they all specifically bind to a tau peptide with phosphorylated serine 413 [PD17(p)PS413 (24AWF), SEQ ID NO:77] (FIG. 2A) but do not bind to the same peptide without phosphorylated serine 413, [PD17 (25AWF), SEQ ID NO:78] (FIG. 2B). Additionally, they do not bind to peptides that are phosphorylated at positions other than serine 413, such as pS396/400/404GC (84AWK, SEQ ID NO:79), pT212/pS214GC (69AXY, SEQ ID NO:80), T-pT217GC (70AXY, SEQ ID NO:82) or pSer412Cys (74AXY, SEQ ID NO:81) (FIGS. 2C-2F). A control antibody, humanized antibody against RSV does not bind to any of the tested peptides (FIGS. 2A-2F).

Example 4. Binding Affinity of the High Affinity Anti-Tau-pS413 Antibodies to FcRn at pH 6 and pH 7.4

SPR assay was used to determine the binding affinity of the high affinity antibodies described herein to human and cynomolgus monkey (cyno) FcRn at pH 6.0 and 7.4. Anti-human kappa antibody was amine coupled to a CMS chip. Each antibody was captured to 200-300 RUs. Binding assays were performed using PBS running buffer containing 0.05% Tween-20, adjusted to either pH 6.0 or 7.4. Titration samples were also prepared using the corresponding pH buffer for the assay. Titrating concentrations (1200 nM top, 6-point, 3-fold dilution series and two zeros) of human or cyno FcRn were injected over the captured mAbs. Each sample injection was followed by two 30-second injections of 10 mM glycine, pH 1.5 and a 12-second injection of 10 mM NaOH to regenerate the surface for subsequent antibody capture and injection. All assays were run on Biacore T200 and/or 4000 instruments (GE Healthcare) and the data were fit to a steady-state approximation model using Biaevaluation software. Affinity at pH 6.0 was calculated as equivalent to concentration at half maximal binding signal in the steady-state approximation (TABLE 9). At pH 7.4, no binding was detectable as expected (data not shown).

Affinities for the high affinity anti-tau-pS413 antibodies at pH 6.0 were in a typical range for FcRn. Due to YTE mutation, V8-AFM-IgG1-LALA-YTE showed about 6.5- and about 11-fold higher affinities against human and cyno FcRn, respectively (TABLE 9).

TABLE 9

Binding affinities of anti-tau-pS413 antibodies to human and cyno FcRn

| Antibody name | Human FcRn | Human FcRn fold change (relative to HmzTa1505-hIgG4-S228P) | Cyno FcRn | Cyno FcRn fold change (relative to HmzTa1505-hIgG4-S228P) |
|---|---|---|---|---|
| V8-AFM-hIgG1 LALA | 2.3E−07 | 1 | 1.6E−07 | 1.6 |
| V8-AFM-hIgG1 LALA-YTE | 3.4E−08 | 6.5 | 2.4E−08 | 11 |
| V8-AFM-hIgG4-S228P | 2.1E−07 | 1 | 2.6E−07 | 1 |
| HmzTa1505-hIgG4-S228P | 2.2E−07 | 1 | 2.6E−07 | 1 |

Example 5. Binding Affinities of the High Affinity Anti-Tau-pS413 Antibodies to Brain Homogenates and CSF Samples from AD Patients and Preclinical Models by Competitive ELISA Binding affinities of various anti-tau-pS413 antibodies described herein for endogenous tau species were determined in brain homogenates and CSF samples from AD patients and preclinical models. Briefly, samples were pre-incubated with different concentrations of various anti-tau-pS413 antibodies, or respective isotype controls. Following a one-hour pre-incubation period, the antigen-antibody (Ag-Ab) mixture was added to plates pre-coated with a total tau capture antibody (Innotest ELISA kit). Unbound ("free") tau-pS413 in the brain homogenate or CSF sample was then detected by biotinylated Ta1505-mIgG2a antibody.

P2 extracts (fractions) were prepared as follows. Ten grams of pre-frontal cortex tissue (ABS Inc) were immersed in artificial CSF buffer (aCSF: 119 mM NaCl, 2.5 mM KCl, 1 mM $NaH_2PO_4$, 1.3 mM $MgSO_4$, 2.5 mM $CaCl_2$, 26 mM $NaHCO_3$, 11 mM glucose, 10 mM HEPES, pH 7.4 and sterile water) with protease and phosphatase inhibitors (Pierce) at the dilution of tissue/buffer 1:5 (w/v). Tissue was homogenized by GentleMACS Dissociator. The lysed tissue was centrifuged at 3000 g for 20 minutes at 4° C. The supernatants were transferred to polycarbonate 50 ml centrifuge tubes and spun at 27,000 g for 20 minutes at 4° C. The supernatants were collected (S1 fraction) and further centrifuged at 150,000 g for 20 minutes at 4° C. The pellets were resuspended, P2 fraction, in aCSF buffer with protease and phosphatase inhibitors and sonicated for a few seconds using a probe sonicator. The concentration of the P2 fraction was determined by BCA protein assay (Pierce) and the P2 fraction were aliquoted and stored at −80° C.

Figure 3A:
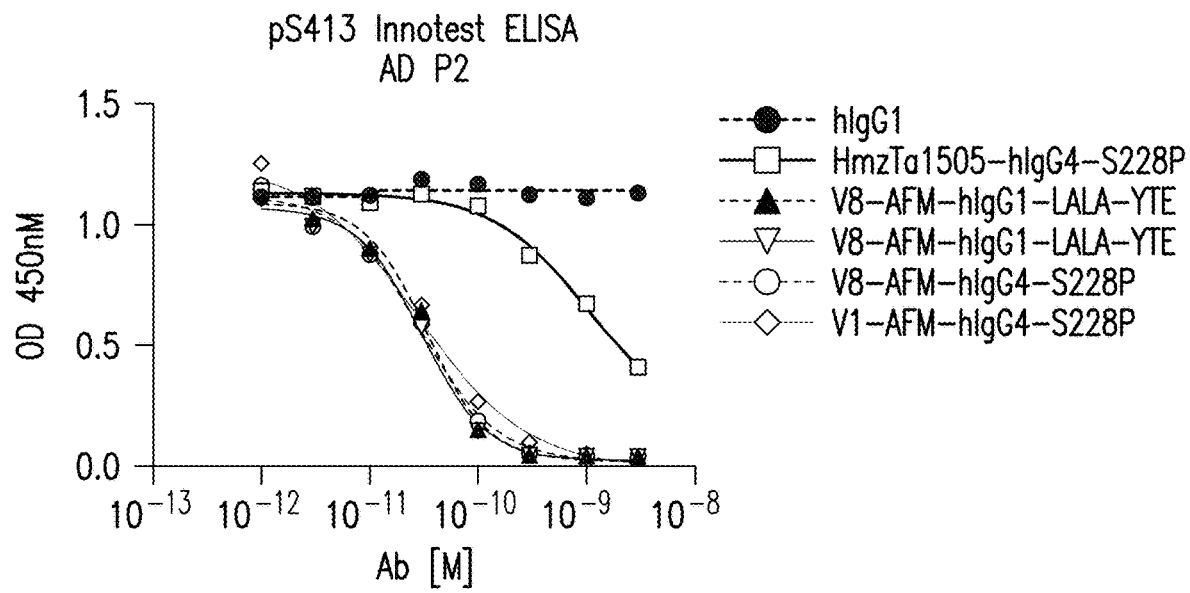
FIGS. 3A and 3B show competitive tau-pS413 immunoassay demonstrating binding of various exemplary anti-tau-pS413 antibodies to AD patient brain homogenates.
Figure 3B:
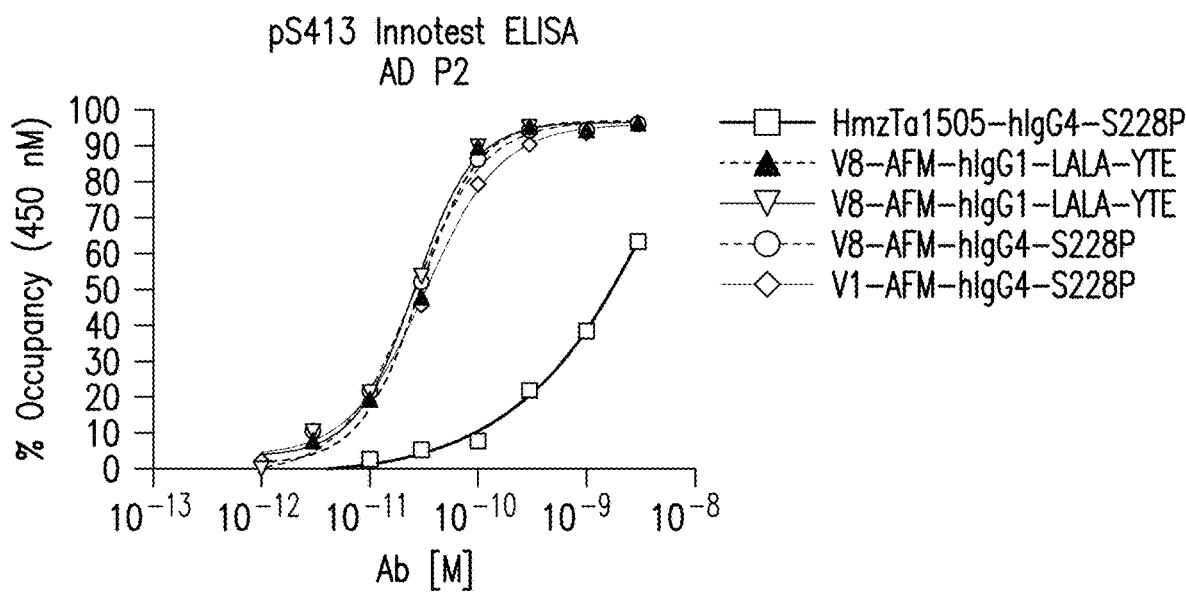

FIG. 3A illustrates the raw data showing the decreased levels of "free" unbound antigen in P2 extracts of AD brain homogenates with increasing concentrations of mAbs, but not isotype control. FIG. 3B illustrates the transformed data where the absorbance (OD) values of isotype control hIgG OD values ("total") were subtracted from test mAbs ("free") and normalized to calculate the occupancy EC50's of the profiled mAbs (TABLE 10). These studies demonstrate that representative high affinity anti-tau-pS413 antibodies binds to AD brain homogenates comparably, with significantly higher affinity than HmzTa1505-hIgG4-S228P.

TABLE 10

Binding affinity of anti-tau-pS413 antibodies to AD brain homogenates

| Antibody name | EC50 (M) |
|---|---|
| HmzTa1505-hIgG4-S228P | 6.50E−10 |
| V1-AFM-hIgG4-S228P | 3.23E−11 |
| V1-AFM-hIgG1-LALA-YTE | 3.10E−11 |
| V2-AFM-hIgG1-LALA | 3.90E−11 |
| V3-AFM-hIgG4-S228P | 2.55E−11 |
| V5-AFM-hIgG4-S228P | 3.10E−11 |
| V6-AFM-hIgG4-S228P | 2.23E−11 |
| V7-AFM-hIgG1-LALA-YTE | 4.10E−11 |
| V8-AFM-hIgG1-LALA-YTE | 2.60E−11 |
| V8-AFM-hIgG1-LALA | 2.60E−11 |
| V8-AFM-hIgG4-S228P | 2.50E−11 |

The high affinity anti-tau-pS413 antibodies described herein also bind to tau species in brain homogenates from mutant tau mice (rTg(tauP301L)4510) (Ramsden M et al., 2005, *J. Neurosci.* 25 (46) 10637-10647) and in the CSF from post-mortem AD patients and African Green Monkeys. Tissue homogenates were prepared using 1% sarkosyl buffer with several high-speed centrifugation steps to enrich for insoluble proteins including tau. Binding measures could not be assessed in CSF of the tau mutant mice because of the limited volume. The "effective" binding potencies of HmzTa1505-hIgG4-S228P and V8-AFM-hIgG1-LALA-YTE for the endogenous tau in the various biological specimens are about 2- to about 10-fold higher than the respective potencies for recombinant phosphorylated tau protein monomer used as standard (TABLE 11). These results suggest anti-tau-pS413 antibodies bind with an avidity component to the target tau species. The binding potencies of V8-AFM-hIgG1-LALA-YTE for these biological tau species are also about 30- to about 200-fold higher than those of HmzTa1505-hIgG4-S228P (TABLE 11).

TABLE 11

Binding potencies to tau species in brain homogenates and CSF samples from AD patients and preclinical models

| Samples | Description | HmzTa1505-hIgG4-S228P EC50 (nM) | V8-AFM-hIgG1-LALA-YTE EC50 (nM) |
|---|---|---|---|
| phosphorylated tau protein monomer | 35 AWM (1 ng) | 6.73 | 0.055 |
| AD brain | P2 high speed pellet (50 ng proteins) | 0.65 | 0.022 |
| Tau mutant mice brain | S1 Tau seeds (4 ng protein) | 0.67 | 0.004 |
| AD post mortem CSF | AD patients (75 μl of neat CSF) | 0.82 (average, n = 3) | 0.004 (average, n = 2) |
| Fresh African Green Monkey (AGM) CSF | 4 AGMs (75 μl of neat CSF) | 2.08 (average, n = 4) | 0.008 (average, n = 2) |

Figure 4A:
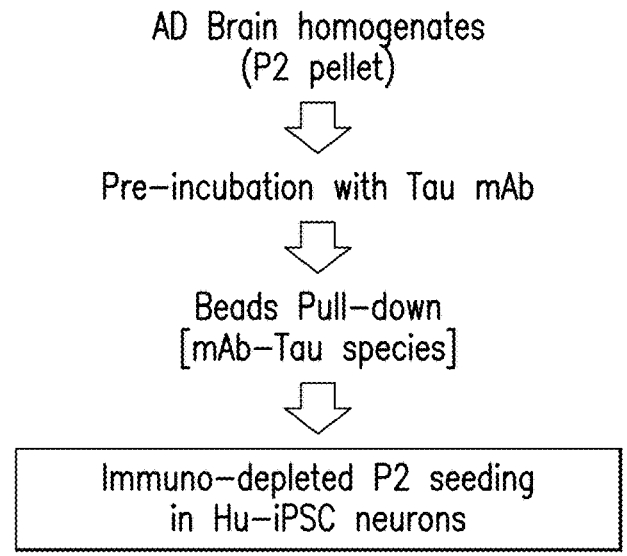
FIGS. 4A-4E demonstrate that immuno-depletion of P2 extract of AD brain homogenates with various exemplary anti-tau-pS413 antibodies prevents the induction of tau pathology in hiPSC neurons.

Example 6. In Vitro Cellular Potency of Neutralization of Seeding Assay in Hu-iPSC Neurons To evaluate and compare the activities of HmzTa1505-hIgG4-S228P and representative high affinity antibodies V1-AFM-hIgG4-S228P and V8-AFM-hIgG1-LALA-YTE in disease cellular system, a model of tau pathology seeding was developed in human iPSC-derived neurons using (P2)

extracts from brain homogenates of AD patients. This neutralization assay consisted of immunodepleting Tau species from P2 AD brain homogenates with tau antibodies or isotype control before seeding the P2 extract in hu-iPSC neuronal culture. The immunodepletion was performed using Dynabeads protein G after pre-incubation of 4 µg of total protein of P2 extract with various concentration of mAbs or corresponding isotype control (3 nM to 3 pM) of tau antibodies or isotype control for 4 hours. Five days after treatment, neurons were immuno-stained with MC1 antibody, a tau mAb specific for pathological tau conformation (provided by Dr. Peter Davies, Department of Pathology; Albert Einstein College of Medicine). Tau pathology was quantified with high-content image analysis based on immuno-staining of MC1 antibody (Representative images in FIG. 4D). This neutralization assay consists of immunodepleting tau species from P2 extracts with HmzTa1505-hIgG4-S228P, V1-AFM-hIgG4-S228P, V8-AFM-hIgG1-LALA-YTE, or corresponding isotype control before seeding the P2 extract in hiPSC neurons (as described in the schematic representation of FIG. 4A).

Figure 4B:
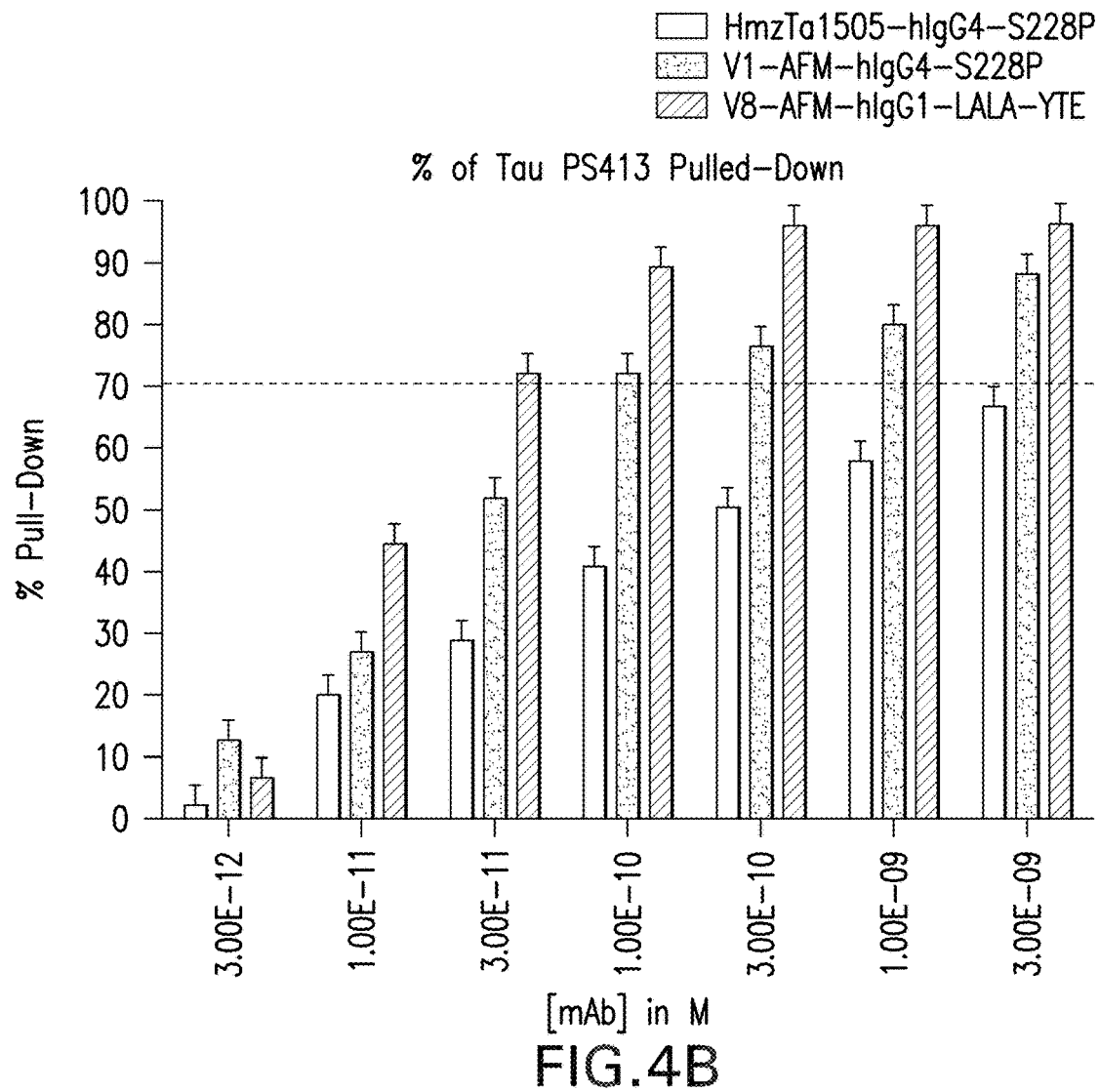
Figure 4C:
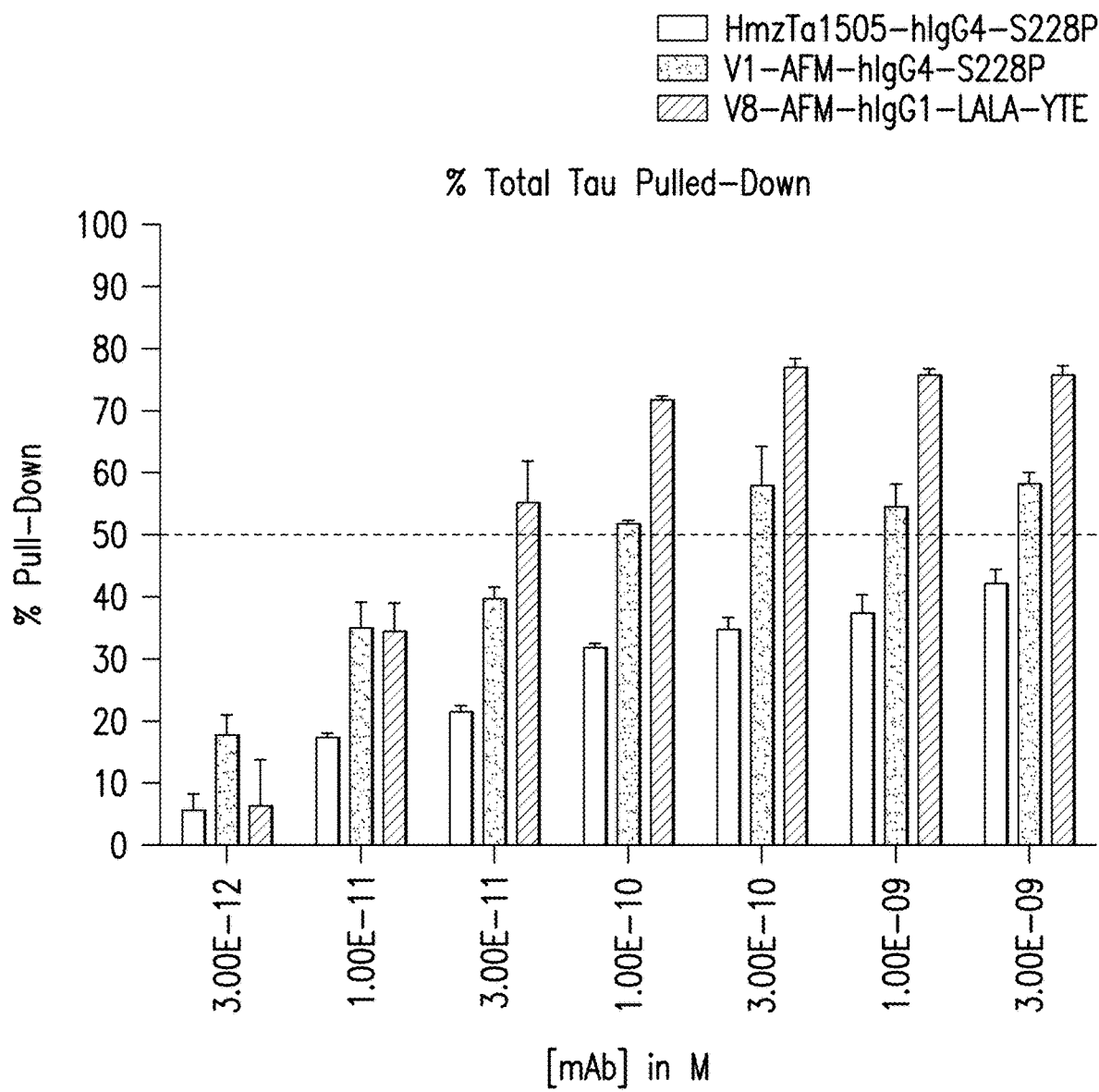
Figure 4D:
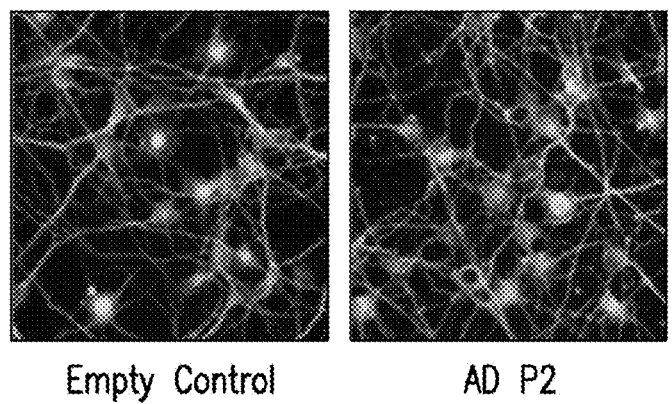

The immuno-depleted samples were tested in AlphaLISA® assay to confirm the successful immuno-depletion of total tau (Tau5/HT7 antibody pair, FIG. 4C) or tau-pS413 species (pTa1505 IgG2a/HT7 antibody pair, FIG. 4B) with HmzTa1505-hIgG4-S228P, V1-AFM-hIgG4-S228P, or V8-AFM-hIgG1-LALA-YTE. Briefly, immunodepleted samples were incubated with HT7 (Thermofisher) acceptor beads (final concentration 20 µg/mL) and Tau5 (Thermofisher) or Ta1505 biotinylated antibody (0.6 µg/mL) for 2 hrs in immunoassay buffer at room temperature. Next, streptavidin donor beads (final concentration 40 µg/mL) were added to the plate and incubated for an additional 1 hr at room temperature with gentle shaking and then the plates were read on Envision plate reader (Perkin Elmer). Results demonstrated an effective pull-down of 70-90% of the tau-pS413 species and 50% of total tau species obtained with 0.1 nM of high affinity variant V1-AFM-hIgG4-S228P or V8-AFM-hIgG1-LALA-YTE versus 3 nM of HmzTa1505-hIgG4-S228P (FIGS. 4B and 4C).

Figure 4E:
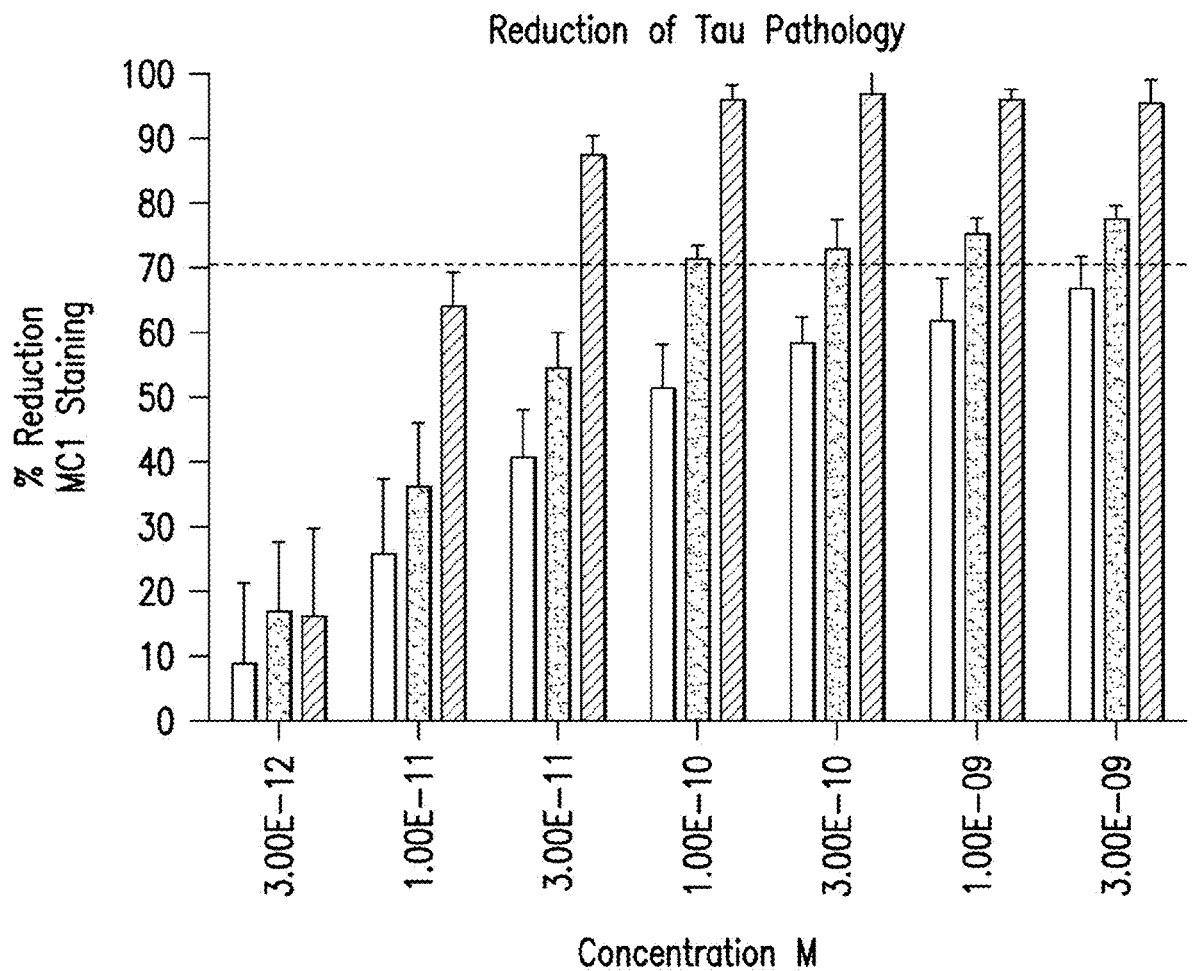

Five days after treatment, neurons were immuno-stained with MC1 antibody. High-content image analysis showed that neutralization with HmzTa1505-hIgG4-S228P, V1-AFM-hIgG4-S228P, or V8-AFM-hIgG1-LALA-YTE significantly decreased MC1 tau pathology in neurons; however, maximum inhibition ~70-90% of tau pathology was observed with 0.1 nM of high affinity variant V1-AFM-hIgG4-S228P or V8-AFM-hIgG1-LALA-YTE versus 3 nM of HmzTa1505-hIgG4-S228P (FIG. 4E). These results demonstrate that anti-tau-pS413 mAb can effectively recognize the toxic tau species found in the AD patient brains. In addition, the high affinity variants V1-AFM-hIgG4-S228P and V8-AFM-hIgG1-LALA-YTE are 30-fold more potent than HmzTa1505-hIgG4-S228P to neutralize the effects of the toxic tau species in inducing tau pathology in the human neuronal cell model.

Example 7. Efficacy of Anti-Tau-pS413 Antibodies in an AD-Derived Tau Hippocampal Injection Model Using Tau Transgenic Mice Previous studies demonstrated a significant reduction in tau pathology following administration of Ta1505-mIgG2a with a trend towards decreases in pathology with increasing doses (see WO 2018/254390). The aim of this study was to determine if the murinized high affinity anti-tau-pS413 antibodies (e.g., V8-AFM-mIgG1), which showed a 40-fold increase binding potency for AD P2 brain extracts (0.013 nM for AFM-mIgG1 versus 0.51 nM for pTa1505, data not shown), was able to reduce tau pathology at lower doses than the parental antibody. An in vivo seeding model was used to evaluate the effect of Ta1505-mIgG1 (40 mg/kg, 10 mg/kg, 5 mg/kg), V8-AFM-mIgG1 (40 mg/kg, 10 mg/kg, 5 mg/kg, 1 mg/kg), or mIgG1 isotype control (40 mg/kg) on the development of tau pathology. Following the antibody treatment, Tg4510 mice (WT:Car) mice were injected into the hippocampus with Sarkosyl Insoluble (SI) Tau preparation from rTg(tauP301L)4510 mice (Car:Car) mice to elicit the transmission and of tau pathology around the injection site and spreading to other brain regions. Mice were then treated weekly with antibody injections. Thirty days after the initial dose, animals were necropsied and brain tissues were stained for tau hyperphosphorylated at amino acid positions S202 and T205 (AT-8 at a dilution of 1:1500 revealed with chromogenic staining). Tau pathology was evaluated in the injected region of the hippocampus. Seven sections of each animal's hippocampus were quantified by Halo software for % of positive staining per area.

Figure 5:
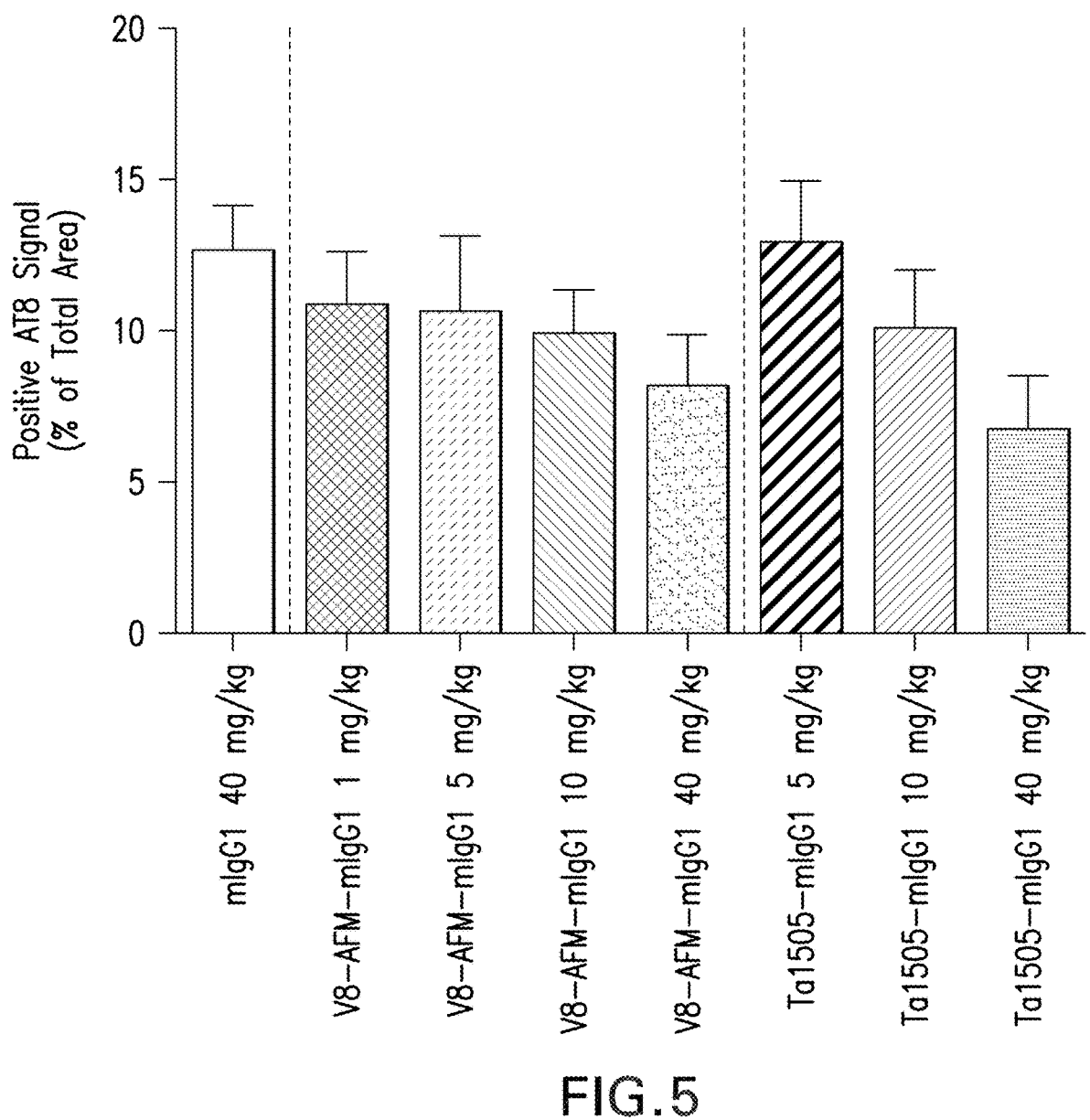
FIG. 5 demonstrates dose response upon administration of an exemplary high affinity anti-tau-pS413 antibody V8-AFM-mIgG1 versus the mouse parental anti-tau-pS413 antibody pTa1505-mIgG1 on the reduction of tau pathology.

FIG. 5 showed a reduced pathology with high doses of both V8-AFM-mIgG1 and Ta1505-mIgG1 and a trend towards a dose response reduction in tau pathology in the ipsilateral hippocampus. While administration of V8-AFM-mIgG1 did not show significantly better reduction in tau pathology, drug exposures were unexpectedly lower in the V8-AFM-mIgG1 groups. In particular, for each dose level, the V8-AFM-mIgG1 group showed 20-fold lower PK levels than the Ta1505-mIgG1 group (TABLE 12). As a result, we could not directly compare the efficacious doses. However, at 40 mg/kg dose, a 35% reduction in pathology was observed for the V8-AFM-mIgG1 group at –300 nM plasma levels whereas a 45% reduction was observed at 20-fold higher plasma exposure for Ta1505-mIgG1 (TABLE 13), suggesting the enhanced potency for the high affinity variant V8-AFM-mIgG1.

TABLE 12

Plasma and CSF concentrations for mAb treatments groups at day 30

| Antibody name | Dose (mg/kg) | Plasma (nM) Mean | SD | CSF (nM) Mean | SD | CSF/plasma ratio |
|---|---|---|---|---|---|---|
| V8-AFM-mIgG1 | 40 | 307.8 | 157..4 | 0.30 | 0.23 | 0.10% |
| V8-AFM-mIgG1 | 10 | 116.7 | 76.3 | 0.35 | 0.65 | 0.30% |
| V8-AFM-mIgG1 | 5 | 41.5 | 48.4 | 0.06 | 0.02 | 0.144% |
| V8-AFM-mIgG1 | 1 | 38.8 | 45.8 | BLQ | BLQ | BLQ |
| Ta1505-mIgG1 | 40 | 6203 | 786.6 | 6.05 | 3.70 | 0.098% |
| Ta1505-mIgG1 | 10 | 1558 | 383.3 | 1.21 | 0.50 | 0.078% |
| Ta1505-mIgG1 | 5 | 1019 | 315.5 | 1.28 | 1.79 | 0.13% |

TABLE 13

Percentage of reduction in tau pathology

| Treatment (antibody, dose) | Percent reduction from mIgG1 control |
|---|---|
| V8-AFM-mIgG1, 40 mg/kg | 35% |
| V8-AFM-mIgG1, 10 mg/kg | 22% |
| V8-AFM-mIgG1, 5 mg/kg | 16% |
| V8-AFM-mIgG1, 1 mg/kg | 14% |
| Ta1505-mIgG1, 40 mg/kg | 45% |

TABLE 13-continued

Percentage of reduction in tau pathology

| Treatment (antibody, dose) | Percent reduction from mIgG1 control |
|---|---|
| Ta1505-mIgG1, 10 mg/kg | 20% |
| Ta1505-mIgG1, 5 mg/kg | −2% |

Example 8. Ex-Vivo Detection of Target Engagement by Anti-Tau-pS413 Antibodies in CSF Samples from Heathy Volunteers and AD Patients An ultra-sensitive electro-chemiluminescent (ECL) assay on the Meso Scale Discovery S-Plex Platform was developed to measure a baseline level of tau-pS413 in human CSF and free (i.e., unbound) tau-pS413 in the presence of tau-pS413-specific antibodies. The method can be used to demonstrate target engagement by anti-tau-pS413 antibodies as a reduction in free tau-pS413 signal. In this sandwich immunoassay, biotinylated mouse monoclonal anti-tau-pS413 antibody Ta1505 was coated onto MSD 96-well S-PLEX SECTOR Plates (Mesoscale Discovery, cat No. L45SA) at 1 µg/mL with 1×S-PLEX Coating Reagent C1 (Mesoscale Discovery Cat No C20H0). CSF samples were diluted 1:2 in Diluent 100 (Mesoscale Discovery Cat. No R50AA) with 0.12 mg/mL Heterophilic S Blocking Reagent 1 (Scantibodies Cat No. 3KC534-075). After washing the coated plate with 1×PBST, 75 µL samples were loaded per well in addition to 75 µL Diluent 100 with 1×S-PLEX Blocking Reagent 51 (Mesoscale Discovery Cat No. R93AG). Samples were incubated overnight at 4° C. on an orbital shaker (700 rpm). After wash steps, the detection antibody, Turbo Boost-tagged Ta1505, was added to each well at 0.2 µg/mL in MSD Diluent 101 (Mesoscale Discovery Cat No. R51AD) and incubated for 1 hour at room temperature on orbital shaker (700 rpm). Color enhancement and development steps were performed following MSD S-PLEX protocol. Plates were read on MESO SECTOR™ 5600 instrument for electro-chemiluminescent signal (A.U.).

Figure 7A:
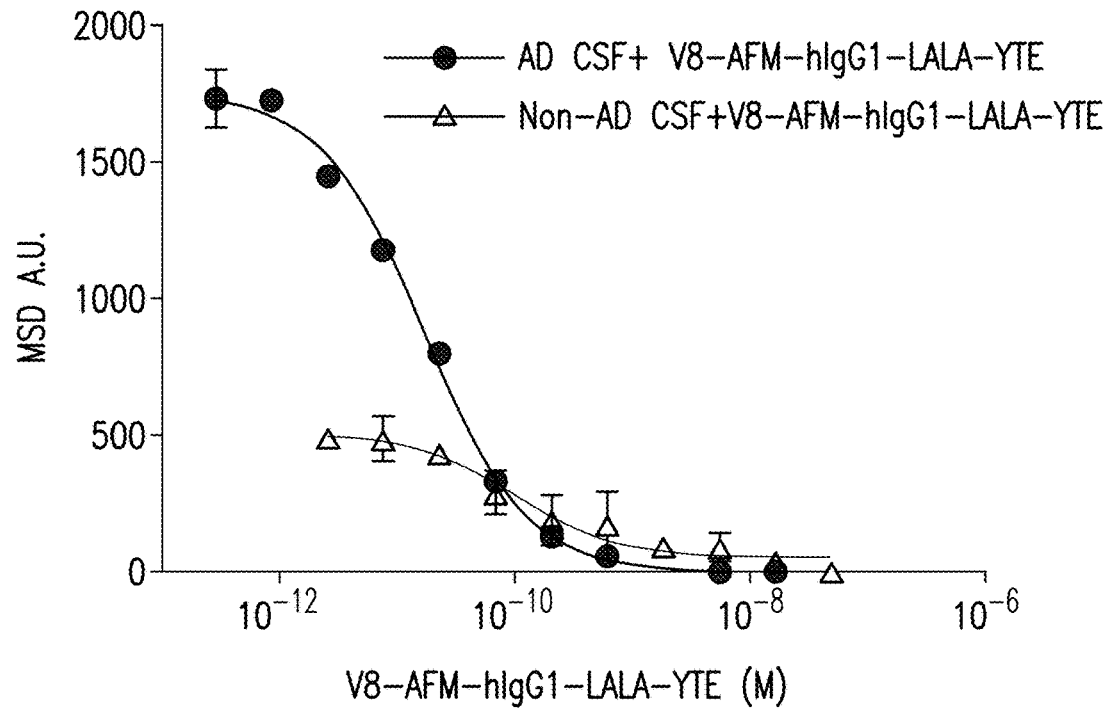
FIGS. 7A and 7B demonstrate ex vivo target engagement by V8-AFM-hIgG1-LALA-YTE in CSF samples from AD patients or non-AD humans.
Figure 7B:
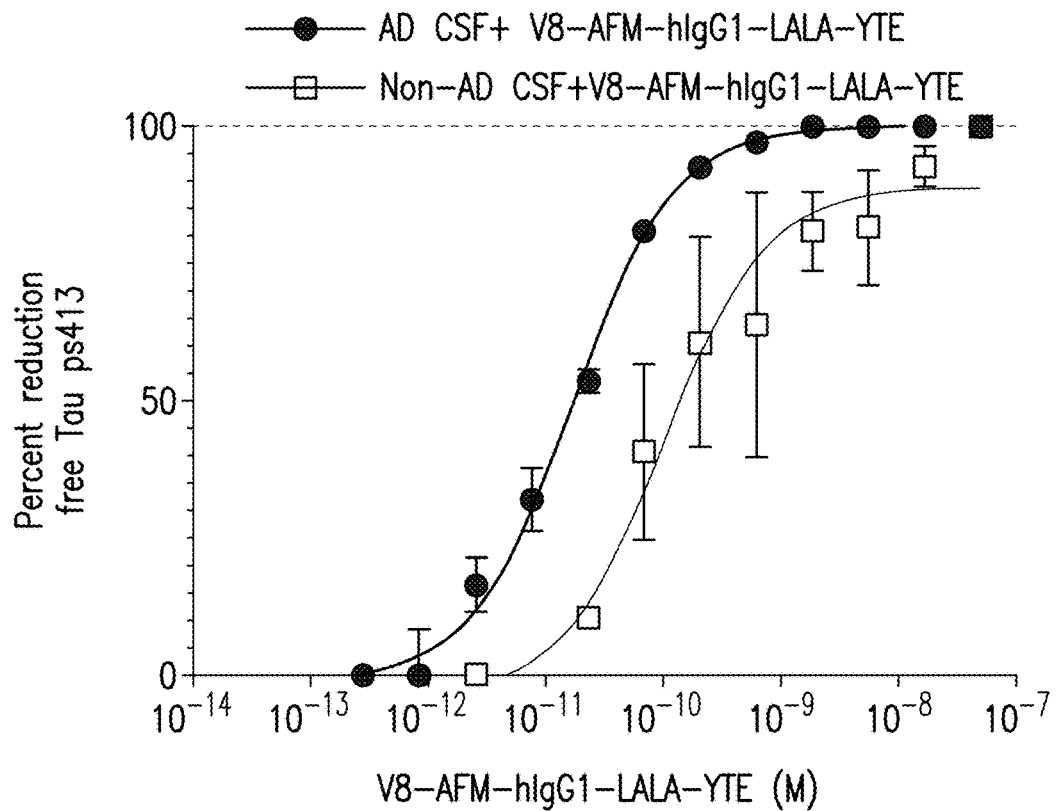

The ex-vivo binding of anti-tau-pS413 antibody was evaluated by quantitating tau-pS413 after incubating human non-AD or AD CSF samples with V8-AFM-hIgG1-LALA-YTE at titrated concentrations (0.085 fM to 50 nM) using the tau-pS413 MSD S-PLEX assay. The assay signal reduced with increasing concentration of V8-AFM-hIgG1-LALA-YTE (FIG. 7A). The antibody reached 100% target occupancy at a concentration from about 1.85 nM to about 50 nM. The percent reduction of the free tau-pS413 (not bound by V8-AFM-hIgG1-LALA-YTE) levels was calculated based on a maximum signal produced without V8-AFM-hIgG1-LALA-YTE and a minimum signal produced without 50 nM V8-AFM-hIgG1-LALA-YTE (both the maximum level and the minimum level subtracted a background level without CSF samples but with the buffer only). The non-linear regression of the concentration-percent of reduction allows the determination of the ex-vivo potency of V8-AFM-hIgG1-LALA-YTE, $IC_{50}$=0.0169 nM (95% confidence 0.0141 to 0.0204 nM), in CSF from AD patients (FIG. 7B). Due to the low tau-pS413 baseline signal and narrow reduction window in non-AD CSF samples, the $IC_{50}$=0.101 nM in CSF from non-AD patients had a larger 95% confidence range (0.045 to 0.243 nM).

All references cited herein are incorporated by reference to the same extent as if each individual publication, database entry (e.g. GenBank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. GenBank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

SEQUENCE LISTING

The present specification is being filed with a computer readable form (CRF) copy of Sequence Listing The CRF entitled 24996USNP-SEQTXT-21MAY2021-ST25.txt, which was created on May 21, 2021 and is 113,796 bytes in size, is identical to the paper copy of the Sequence Listing and is incorporated herein by reference in its entirety. TABLE 14 below summaries all sequences disclosed in the specification.

TABLE 14

Sequences disclosed in the specification

| SEQ ID NO | Sequence Description | Sequence (SEQ ID NO: 107 and 108 are nucleotide sequences, the rest are amino acid sequences) |
|---|---|---|
| 1 | Human tau isoform 4R2N | MAEPRQEFEVMEDHAGTYGLGDRKDQG-GYTMHQDQEGDTDAG LKESPLQTPTEDGSEEPGSETSDAKSTPTAEDVTAPLV-DEGA PGKQAAAQPHTEIPEGTTAEEA-GIGDTPSLEDEAAGHVTQAR |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | MVSKSKDGTGSDDKKAKGADGKTKIATPR-GAAPPGQKGQANATRIPAKTP-PAPKTPPSSGEPPKSGDRSGYSSPGSPGTPGSRSRTPSLPTPPTREPKKVAVVRTPPKSPS-SAKSRLQTAPVPMPDLKNVKSKIGSTENLKHQPGGGKVQIINKKLDL-SNVQSKCGSKDNIKHVPGGGSVQIVYKPVDL-SKVTSKCGSLGNIHHKPGGGQVEVKSEKLDFKDRVQSKIGSLDNITHVPGGGNKKI-ETHKLTFRENAKAKTDHGAEIVYKSPVVSGDTSPRHL-SNVSSTGSIDMVDSPQLATLADEVSASLAKQGL |
| 2 | Human tau isoform 4R1N | MAEPRQEFEVMEDHAGTYGLGDRKDQG-GYTMHQDQEGDTDAGLKESPLQTPTEDGSEEPGSETSDAKSTPTAEAEEA-GIGDTPSLEDEAAGHVTQARMVSKSKDGTGSDDKKAKGADGKTKI-ATPRGAAPPGQKGQANATRIPAKTP-PAPKTPPSSGEPPKSGDRSGYSSPGSPGTPGSRSRTPSLPTPPTREPKKVAVVRTPPK-SPSSAKSRLQTAPVPMPDLKNVKSKIGSTENLKHQPGGGKVQI-INKKLDLSNVQSKCGSKDNIKHVPGGGSVQIVYKPVDL-SKVTSKCGSLGNIHHKPGGGQVEVKSEKLDFKDRVQSKIGSLD-NITHVPGGGNKKIETHKLTFRENAKAKTDHGAEIVYKSPVVSGDT-SPRHLSNVSSTGSIDMVDSPQLATLADEVSASLAKQGL |
| 3 | Human tau isoform 4R0N | MAEPRQEFEVMEDHAGTYGLGDRKDQG-GYTMHQDQEGDTDAGLKAEEAGIGDTPSLEDEAAGHVTQARMVSK-SKDGTGSDDKKAKGADGKTKIATPRGAAPPGQKGQANATRIPAKTP-PAPKTPPSSGEPPKSGDRSGYSSPGSPGTPGSRSRTPSLPTPP-TREPKKVAVVRTPPKSPSSAKSRLQTAPVPMPDLKNVKSKIG-STENLKHQPGGGKVQIINKKLDLSNVQSKCGSKD-NIKHVPGGGSVQIVYKPVDL-SKVTSKCGSLGNIHHKPGGGQVEVKSEKLDFKDRVQSKIGSLDNITHVPGGGNKKIETHKLTFRENAKAKTDH-GAEIVYKSPVVSGDTSPRHLSNVSSTGSIDMVDSPQLAT-LADEVSASLAKQGL |
| 4 | Human tau isoform 3R2N | MAEPRQEFEVMEDHAGTYGLGDRKDQG-GYTMHQDQEGDTDAGLKESPLQTPTEDGSEEPGSETSDAKSTPTAEDVTAPLV-DEGAPGKQAAAQPHTEIPEGTTAEEA-GIGDTPSLEDEAAGHVTQARMVSKSKDGTGSDDKKAKGADGKTKIATPR-GAAPPGQKGQANATRIPAKTP-PAPKTPPSSGEPPKSGDRSGYSSPGSPGTPGSRSRTPSLPTPPTREPKKVAVVRTPPKSPS-SAKSRLQTAPVPMPDLKNVKSKIGSTENLKHQPGGGKVQIVYKPVDL-SKVTSKCGSLGNIHHKPGGGQVEVKSEKLDFKDRVQSKIGSLD-NITHVPGGGNKKIETHKLTFRENAKAKTDHGAEIVYKSPVVSGDT-SPRHLSNVSSTGSIDMVDSPQLATLADEVSASLAKQGL |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| 5 | Human tau isoform 3R1N | MAEPRQEFEVMEDHAGTYGLGDRKDQG-GYTMHQDQEGDTDAG LKESPLQTPTEDGSEEPGSETSDAKSTPTAEAEEA-GIGDTPS LEDEAAGHVTQARMVSKSKDGTGSDDKKAKGADGKTKI-ATPR GAAPPGQKGQANATRIPAKTP-PAPKTPPSSGEPPKSGDRSGY SSPGSPGTPGSRSRTPSLPTPPTREPKKVAVVRTPPK-SPSSA KSRLQTAPVPMPDLKNVKSKIGSTENLKHQPGGGKVQI-VYKP VDL-SKVTSKCGSLGNIHHKPGGGQVEVKSEKLDFKDRVQSKI GSLDNITHVPGGGNKKIETHKLTFRENAKAKTDH-GAEIVYKS PVVSGDTSPRHLSNVSSTGSIDMVDSPQLAT-LADEVSASLAK QGL |
| 6 | Human tau isoform 3R0N | MAEPRQEFEVMEDHAGTYGLGDRKDQG-GYTMHQDQEGDTDAG LKAEEAGIGDTPSLEDEAAGHVTQARMVSK-SKDGTGSDDKKA KGADGKTKIATPRGAAPPGQKGQANATRIPAKTP-PAPKTPPS SGEPPKSGDRSGYSSPGSPGTPGSRSRTPSLPTPP-TREPKKV AVVRTPPKSPSSAKSRLQTAPVPMPDLKNVKSKIG-STENLKH QPGGGKVQIVYKPVDL-SKVTSKCGSLGNIHHKPGGGQVEVKS EKLDFKDRVQSKIGSLDNITHVPGGGNKKI-ETHKLTFRENAK AKTDHGAEIVYKSPVVSGDTSPRHLSNVSSTGSIDMVD-SPQL ATLADEVSASLAKQGL |
| 7 | Ta1505, VL-CDR1 | RSSQNIVHSNGNTYLE |
| 8 | Ta1505, VL-CDR2 | TVSNRFS |
| 9 | Ta1505, VL-CDR3 | FQGSHLPLT |
| 10 | Ta1505, VL | DILMTQTPLSLPVSLGDQASISCRSSQNIVHSNGN-TYLEWYL QKPGQSPKVLIYTVSNRFSGVPDRFSGSGSGTDFTLKIS-RVE AEDLGVYYCFQGSHLPLTFGGGTKLELK |
| 11 | Ta1505, light chain | DILMTQTPLSLPVSLGDQASISCRSSQNIVHSNGN-TYLEWYL QKPGQSPKVLIYTVSNRFSGVPDRFSGSGSGTDFTLKIS-RVE AEDLGVYYCFQGSHLPLTFGGGTKLELKRADAAPTVSIFPPS SEQLTSGGASVVCFLNNFYPKDINVKWKIDGSER-QNGVLNSW TDQDSKDSTYSMSSTLTLTKDEYERHNSYTCEATHKTST-SPI VKSFNRNEC |
| 12 | Ta1505, VH-CDR1 | SFALN |
| 13 | Ta1505, VH-CDR2 | HIRSKTNNYATFYADSVKD |
| 14 | Ta1505, VH-CDR3 | RGPRDSWFGY |
| 15 | Ta1505, VH | EVQLVESGGGLVQPKGSLKLSCAASGFAFNSFAL-NWVRQAPG KSLEWVVHIRSKTNNYATFY-ADSVKDRFTVSRDDSQSMVYLQ MNNLKTEDTGIYYCVRRGPRDSWFGYWGQGTLVTVSA EVQLVESGGGLVQPKGSLKLSCAASGFAFNSFAL-NWVRQAPG |
| 16 | Ta1505, heavy chain | KSLEWVVHIRSKTNNYATFY-ADSVKDRFTVSRDDSQSMVYLQ |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | MNNLKTEDTGIYYCVRRGPRD-SWFGYWGQGTLVTVSAAKTTA PSVYPLAPVCGDTTGSSVTLGCLVKGYF-PEPVTLTWNSGSLS SGVHTFPAVLQSDLYTLSSSVTVTSSTWPSQSITCNVAH-PAS STKVDKKIEPRGPTIKPCPPCKCPAPNLLGGPSVFIFPP-KIK DVLMISLSPIVTCVVVDVSEDDPDVQISWFVNN-VEVHTAQTQ THREDYNSTLRVVSALPIQHQDWMSGKEFKCKVNNKDL-PAPI ERTISKPKGSVRAPQVYVLPP-PEEEMTKKQVTLTCMVTDFMP EDIYVEWTNNGKTELNYKNTEPVLDSDGSYFMYSK-LRVEKKN WVERNSYSCSVVHEGLHNHHTTKSFSRTPGK |
| 17 | VL46, VL-CDR1 | RSSQSIVHSNGNTYLE |
| 18 | VL46, VL-CDR2 | TVSNRFS |
| 19 | VL46, VL-CDR3 | FQGSHLPLT |
| 20 | VL46, VL | DIVMTQSPLSLPVTLGEPASISCRSSQSIVHSNGN-TYLEWYL QKPGQSPQLLIYTVSNRFSGVPDRFSGSGSGTDFTLKIS-RVE AEDLGVYYCFQGSHLPLTFGGGTKVEIK |
| 21 | VH11, VH-CDR1 | SFALN |
| 22 | VH11, VH-CDR2 | HIRSKTNNYATFYAASVKD |
| 23 | VH11, VH-CDR3 | RGPRDSWFGY |
| 24 | VH11, VH | EVQLVESGGGLVQPGGSLRLSCAASGFTFSSFAL-NWVRQAPG KGLEWVGHIRSKTNNYATFYAASVKDRFTVSRDDSQN-TAYLQ MNSLKTEDTATYYCVRRGPRDSWFGYWGQGTLVTVSS |
| 25 | VL46_G34A_S28N, VL-CDR1 | RSSQNIVHSNANTYLE |
| 26 | VL46_G34A_S28N, VL-CDR2 | TVSNRFS |
| 27 | VL46_G34A_S28N, VL-CDR3 | FQGSHLPLT |
| 28 | VL46_G34A_S28N, VL | DIVMTQSPLSLPVTLGEPASISCRSSQNIVHSNAN-TYLEWYL QKPGQSPQLLIYTVSNRFSGVPDRFSGSGSGTDFTLKIS-RVE AEDLGVYYCFQGSHLPLTFGGGTKVEIK |
| 29 | VL46_G34A_S28N_Q27R_S32R_H98Y, VL-CDR1 | RSSRNIVHRNANTYLE |
| 30 | VL46_G34A_S28N_Q27R_S32R_H98Y, VL-CDR2 | TVSNRFS |
| 31 | VL46_G34A_S28N_Q27R_S32R_H98Y, VL-CDR3 | FQGSYLPLT |
| 32 | VL46_G34A_S28N_Q27R_S32R_H98Y, VL | DIVMTQSPLSLPVTLGEPASISCRSSRNIVHRNAN-TYLEWYL QKPGQSPQLLIYTVSNRFSGVPDRFSGSGSGTDFTLKIS-RVE AEDLGVYYCFQGSYLPLTFGGGTKVEIK |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| 33 | VL46_G34A_S28K_S32R_H98Y, VL-CDR1 | RSSQKIVHRNANTYLE |
| 34 | VL46_G34A_S28K_S32R_H98Y, VL-CDR2 | TVSNRFS |
| 35 | VL46_G34A_S28K_S32R_H98Y, VL-CDR3 | FQGSYLPLT |
| 36 | VL46_G34A_S28K_S32R_H98Y, VL | DIVMTQSPLSLPVTLGEPASISCRSSQKIVHRNAN-TYLEWYL QKPGQSPQLLIYTVSNRFSGVPDRFSGSGSGTDFTLKIS-RVE AEDLGVYYCFQGSYLPLTFGGGTKVEIK |
| 37 | VL46_G34A_S28N_Q27H_S32R_H98Y, VL-CDR1 | RSSHNIVHRNANTYLE |
| 38 | VL46_G34A_S28N_Q27H_S32R_H98Y, VL-CDR2 | TVSNRFS |
| 39 | VL46_G34A_S28N_Q27H_S32R_H98Y, VL-CDR3 | FQGSYLPLT |
| 40 | VL46_G34A_S28N_Q27H_S32R_H98Y, VL | DIVMTQSPLSLPVTLGEPASISCRSSHNIVHRNAN-TYLEWYL QKPGQSPQLLIYTVSNRFSGVPDRFSGSGSGTDFTLKIS-RVE AEDLGVYYCFQGSYLPLTFGGGTKVEIK |
| 41 | VH11_D68G, VH-CDR1 | SFALN |
| 42 | VH11_D68G, VH-CDR2 | HIRSKTNNYATFYAASVKG |
| 43 | VH11_D68G, VH-CDR3 | RGPRDSWFGY |
| 44 | VH11_D68G, VH | EVQLVESGGGLVQPGGSLRLSCAASGFTFSSFAL-NWVRQAPG KGLEWVGHIRSKTNNYATFYAASVKGRFTVSRDDSQN-TAYLQ MNSLKTEDTATYYCVRRGPRDSWFGYWGQGTLVTVSS |
| 45 | VH11_A59V_D68G, VH-CDR1 | SFALN |
| 46 | VH11_A59V_D68G, VH-CDR2 | HIRSKTNNYVTFYAASVKG |
| 47 | VH11_A59V_D68G, VH-CDR3 | RGPRDSWFGY |
| 48 | VH11_A59V_D68G, VH | EVQLVESGGGLVQPGGSLRLSCAASGFTFSSFAL-NWVRQAPG KGLEWVGHIRSKTNNYVTFYAASVKGRFTVSRDDSQN-TAYLQ MNSLKTEDTATYYCVRRGPRDSWFGYWGQGTLVTVSS |
| 49 | VH11_K54E_D68G, VH-CDR1 | SFALN |
| 50 | VH11_K54E_D68G, VH-CDR2 | HIRSETNNYATFYAASVKG |
| 51 | VH11_K54E_D68G, VH-CDR3 | RGPRDSWFGY |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| 52 | VH11_K54E_D68G, VH | EVQLVESGGGLVQPGGSLRLSCAASGFTFSSFAL-NWVRQAPG KGLEWVGHIRSETNNYATFYAASVKGRFTVSRDDSQN-TAYLQ MNSLKTEDTATYYCVRRGPRDSWFGYWGQGTLVTVSS |
| 53 | VH11_K54E_A59V_D68G, VH-CDR1 | SFALN |
| 54 | VH11 K54E_A59V_D68G, VH-CDR2 | HIRSETNNYVTFYAASVKG |
| 55 | VH11 K54E_A59V_D68G, VH-CDR3 | RGPRDSWFGY |
| 56 | VH11 K54E_A59V D68G, VH | EVQLVESGGGLVQPGGSLRLSCAASGFTFSSFAL-NWVRQAPG KGLEWVGHIRSETNNYVTFYAASVKGRFTVSRDDSQN-TAYLQ MNSLKTEDTATYYCVRRGPRDSWFGYWGQGTLVTVSS |
| 57 | Human lambda light chain, constant region | GQPKANPTVTLFPPSSEELQANKATLVCLISDFYP-GAVTVAW KADGSPVKAGVETTKPSKQSNNKYAASSYLSLTPEQWK-SHRS YSCQVTHEGSTVEKTVAPTECS |
| 58 | Human kappa light chain, constant region | RTVAAPSVFIFPPSDEQLKSGTASVVCLLNNFY-PREAKVQWK VDNALQSGNSQESVTEQDSKDSTYSLSSTLTL-SKADYEKHKV YACEVTHQGLSSPVTKSFNRGEC |
| 59 | Human IgG1 heavy chain, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PELLGGPSVFLF PPKPKDTLMISRTPEVTCVVVDVSHEDPE-VKFNWYVDGVEVH NAKTKPREEQYN-STYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 60 | Human_IgG1_LALA, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PEaaGGPSVFLF PPKPKDTLMISRTPEVTCVVVDVSHEDPE-VKFNWYVDGVEVH NAKTKPREEQYN-STYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 61 | Human_IgG1_LALA_D265S, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PEaaGGPSVFLF PPKPKDTLMISRTPEVTCVVVsVSHEDPE-VKFNWYVDGVEVH NAKTKPREEQYN-STYRVVSVLTVLHQDWLNGKEYKCKVSNKA LPAPIEKTISKAKGQPREPQVYTLPPSRDELTKNQVSLT-CLV |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | KGFYPSDIAVEWESNGQPENNYKTTPPVLDSDGSFFLY-SKLT VDKSRWQQGNVFSCSVMHEALHNHYTQKSLSLSPGK |
| 62 | Human_IgG1_YTE, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PELLGGPSVFLF PPKPKDTLyItRePEVTCVVVDVSHEDPE-VKFNWYVDGVEVH NAKTKPREEQYN-STYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 63 | Human_IgG1_LALA_YTE, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PEaaGGPSVFLF PPKPKDTLyItRePEVTCVVVDVSHEDPE-VKFNWYVDGVEVH NAKTKPREEQYN-STYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 64 | Human_IgG1_N297A, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PELLGGPSVFLF PPKPKDTLMISRTPEVTCVVVDVSHEDPE-VKFNWYVDGVEVH NAKTKPRE-EQYASTYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 65 | Human_IgG1_N297Q, constant region | ASTKGPSVFPLAPSSKSTSGGTAALGCLVKDYF-PEPVTVSWN SGALTSGVHTFPAVLQSSGLYS-LSSVVTVPSSSLGTQTYICN VNHKPSNTKVDKKVEPKSCDKTHTCPPCPA-PELLGGPSVFLF PPKPKDTLMISRTPEVTCVVVDVSHEDPE-VKFNWYVDGVEVH NAKTKPRE-EQYqSTYRVVSVLTVLHQDWLNGKEYKCKVSNKA LPAPIEKTISKAKGQPREPQVYTLPPSRDELTKNQVSLT-CLV KGFYPSDIAVEWESNGQPENNYKTTPPVLDSDGSFFLY-SKLT VDKSRWQQGNVFSCSVMHEALHNHYTQKSLSLSPGK |
| 66 | Human IgG2, constant region | ASTKGPSVFPLAPCSRSTSESTAALGCLVKDYF-PEPVTVSWN SGALTSGVHTFPAVLQSSGLYS-LSSVVTVPSSNFGTQTYTCN VDHKPSNTKVDKTVERKCCVECPPCPAPPVAGPSVFLFPPKP KDTLMISRTPEVTCVVVDVSHEDPE-VQFNWYVDGVEVHNAKT KPREEQFNSTFRVVSVLTVVHQDWLNGKEYKCKVSNKGL-PAP IEKTISKTKGQPREPQVYTLPPSREEMTKNQVSLT-CLVKGFY |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | PSDISVEWESNGQPENNYKTTPPMLDSDGSFFLYSK-LTVDKS RWQQGNVFSCSVMHEALHNHYTQKSLSLSPGK |
| 67 | Human_IgG4, constant region | ASTKGPSVFPLAPCSRSTSESTAALGCLVKDYF-PEPVTVSWN SGALTSGVHTFPAVLQSSGLYS-LSSVVTVPSSSLGTKTYTCN VDHKPSNTKVDKRVESKYGPPCPSCPAPE-FLGGPSVFLFPPK PKDTLMISRTPEVTCVVVDVSQEDPE-VQFNWYVDGVEVHNAK TKPREEQFN-STYRVVSVLTVLHQDWLNGKEYKCKVSNKGLPS SIEKTISKAKGQPREPQVYTLPPSQEEMTKNQVSLT-CLVKGF YPSDIAVEWESNGQPENNYKTTPPVLDSDGSFFLY-SRLTVDK SRWQEGNVFSCSVMHEALHNHYTQKSLSLSLGK |
| 68 | Human_IgG4_S228P, constant region | ASTKGPSVFPLAPCSRSTSESTAALGCLVKDYF-PEPVTVSWN SGALTSGVHTFPAVLQSSGLYS-LSSVVTVPSSSLGTKTYTCN VDHKPSNTKVDKRVESKYGPPCPPCPAPE-FLGGPSVFLFPPK PKDTLMISRTPEVTCVVVDVSQEDPE-VQFNWYVDGVEVHNAK TKPREEQFN-STYRVVSVLTVLHQDWLNGKEYKCKVSNKGLPS SIEKTISKAKGQPREPQVYTLPPSQEEMTKNQVSLT-CLVKGF YPSDIAVEWESNGQPENNYKTTPPVLDSDGSFFLY-SRLTVDK SRWQEGNVFSCSVMHEALHNHYTQKSLSLSLGK |
| 69 | VL46_G34A_S28N_ kappa light chain | DIVMTQSPLSLPVTLGEPASISCRSSQNIVHSNAN-TYLEWYL QKPGQSPQLLIYTVSNRFSGVPDRFSGSGSGTDFTLKIS-RVE AEDLGVYYCFQGSHLPLTFGGGTKVEIKRTVAAPSVFIFPPS DEQLKSGTASVVCLLNNFYPREAKVQWKVD-NALQSGNSQESV TEQDSKDSTYSLSSTLTLSKADYEKHKVYACE-VTHQGLSSPV TKSFNRGEC |
| 70 | VH11_IgG4-S228P heavy chain | EVQLVESGGGLVQPGGSLRLSCAASGFTFSSFAL-NWVRQAPG KGLEWVGHIRSKTNNYATFYAASVKDRFTVSRDDSQN-TAYLQ MNSLKTEDTATYYCVRRGPRDSWFGYWGQGTLVTVSSAS-TKG PSVFPLAPCSRSTSESTAALGCLVKDYF-PEPVTVSWNSGALT SGVHTFPAVLQSSGLYS-LSSVVTVPSSSLGTKTYTCNVDHKP SNTKVDKRVESKYGPPCPPCPAPE-FLGGPSVFLFPPKPKDTL MISRTPEVTCVVVDVSQEDPE-VQFNWYVDGVEVHNAKTKPRE EQFN-STYRVVSVLTVLHQDWLNGKEYKCKVSNKGLPSSIEKT ISKAKGQPREPQVYTLPPSQEEMTKNQVSLT-CLVKGFYPSDI AVEWESNGQPENNYKTTPPVLDSDGSFFLY-SRLTVDKSRWQE GNVFSCSVMHEALHNHYTQKSLSLSLGK |
| 71 | V8-AFM-hIgG1 LALA, light chain | DIVMTQSPLSLPVTLGEPASISCRSSQKIVHRNAN-TYLEWYL QKPGQSPQLLIYTVSNRFSGVPDRFSGSGSGTDFTLKIS-RVE AEDLGVYYCFQG-SYLPLTFGGGTKVEIKRTVAAPSVFIFPPS DEQLKSGTASVVCLLNNFYPREAKVQWKVD-NALQSGNSQESV |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | TEQDSKDSTYSLSSTLTLSKADYEKHKVYACE-VTHQGLSSPV TKSFNRGEC |
| 72 | V8-AFM-hIgG1 LALA, heavy chain | EVQLVESGGGLVQPGGSLRLSCAASGFTFSSFAL-NWVRQAPG KGLEWVGHIRSETNNYVTFYAASVKGRFTVSRDDSQN-TAYLQ MNSLKTEDTATYYCVRRGPRDSWFGYWGQGTLVTVSSAS-TKG PSVFPLAPSSKSTSGGTAALGCLVKDYF-PEPVTVSWNSGALT SGVHTFPAVLQSSGLYS-LSSVVTVPSSSLGTQTYICNVNHKP SNTKVDKKVEPKSCDKTHTCPPCPA-PEaaGGPSVFLFPPKPK DTLMISRTPEVTCVVVDVSHEDPE-VKFNWYVDGVEVHNAKTK PREEQYNSTYRVVSVLTVLHQDWLNGKEYKCKVSNKAL-PAPI EKTISKAKGQPREPQVYTLPPSRDELTKNQVSLT-CLVKGFYP SDIAVEWESNGQPENNYKTTPPVLDSDGSFFLYSK-LTVDKSR WQQGNVFSCSVMHEALHNHYTQKSLSLSPGK |
| 73 | V8-AFM-hIgG1 LALAYTE, light chain | DIVMTQSPLSLPVTLGEPASISCRSSQKIVHRNAN-TYLEWYL QKPGQSPQLLIYTVSNRFSGVPDRFSGSGSGTDFTLKIS-RVE AEDLGVYYCFQG-SYLPLTFGGGTKVEIKRTVAAPSVFIFPPS DEQLKSGTASVVCLLNNFYPREAKVQWKVD-NALQSGNSQESV TEQDSKDSTYSLSSTLTLSKADYEKHKVYACE-VTHQGLSSPV TKSFNRGEC |
| 74 | V8-AFM-hIgG1 LALA YTE, heavy chain | EVQLVESGGGLVQPGGSLRLSCAASGFTFSSFAL-NWVRQAPG KGLEWVGHIRSETNNYVTFYAASVKGRFTVSRDDSQN-TAYLQ MNSLKTEDTATYYCVRRGPRDSWFGYWGQGTLVTVSSAS-TKG PSVFPLAPSSKSTSGGTAALGCLVKDYF-PEPVTVSWNSGALT SGVHTFPAVLQSSGLYS-LSSVVTVPSSSLGTQTYICNVNHKP SNTKVDKKVEPKSCDKTHTCPPCPA-PEaaGGPSVFLFPPKPK DTLyItRePEVTCVVVDVSHEDPE-VKFNWYVDGVEVHNAKTK PREEQYNSTYRVVSVLTVLHQDWLNGKEYKCKVSNKAL-PAPI EKTISKAKGQPREPQVYTLPPSRDELTKNQVSLT-CLVKGFYP SDIAVEWESNGQPENNYKTTPPVLDSDGSFFLYSK-LTVDKSR WQQGNVFSCSVMHEALHNHYTQKSLSLSPGK |
| 75 | V8-AFM-hIgG4, light chain | DIVMTQSPLSLPVTLGEPASISCRSSQKIVHRNAN-TYLEWYL QKPGQSPQLLIYTVSNRFSGVPDRFSGSGSGTDFTLKIS-RVE AEDLGVYYCFQG-SYLPLTFGGGTKVEIKRTVAAPSVFIFPPS DEQLKSGTASVVCLLNNFYPREAKVQWKVD-NALQSGNSQESV TEQDSKDSTYSLSSTLTLSKADYEKHKVYACE-VTHQGLSSPV TKSFNRGEC |
| 76 | V8-AFM-hIgG4, heavy chain | EVQLVESGGGLVQPGGSLRLSCAASGFTFSSFAL-NWVRQAPG KGLEWVGHIRSETNNYVTFYAASVKGRFTVSRDDSQN-TAYLQ MNSLKTEDTATYYCVRRGPRDSWFGYWGQGTLVTVSSAS-TKG |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | PSVFPLAPCSRSTSESTAALGCLVKDYF-PEPVTVSWNSGALT SGVHTFPAVLQSSGLYS-LSSVVTVPSSSLGTKTYTCNVDHKP SNTKVDKRVESKYGPPCPPCPAPE-FLGGPSVFLFPPKPKDTL MISRTPEVTCVVVDVSQEDPE-VQFNWYVDGVEVHNAKTKPRE EQFN-STYRVVSVLTVLHQDWLNGKEYKCKVSNKGLPSSIEKT ISKAKGQPREPQVYTLPPSQEEMTKNQVSLT-CLVKGFYPSDI AVEWESNGQPENNYKTTPPVLDSDGSFFLY-SRLTVDKSRWQE GNVFSCSVMHEALHNHYTQKSLSLSLGK |
| 77 | PD17(P) | PRHLSNVS(pS)TGSIDMVD |
| 78 | PD17 | PRHLSNVSSTGSIDMVD |
| 79 | T-pS396/400/404GC | GCRENAKAKTDHGAEIVYK(pS)PVV(pS)GDT(pS)PRHL |
| 80 | T-pT212pS214GC | GCGSPGTPGSRSR(pT)P(pS)LPTPPTREPK |
| 81 | pSer412Cys | NV(pS)STGSC |
| 82 | T-pT217GC | GCGSRSRTPSLP(PT)PPTREPKKVAVV |
| 83 | VL-CDR1, AbM | RSSQKIVHRNANTYLE |
| 84 | VL-CDR2, AbM | TVSNRFS |
| 85 | VL-CDR3, AbM | FQGSYLPLT |
| 86 | VH-CDR1, AbM | GFTFSSFALN |
| 87 | VH-CDR2, AbM | HIRSETNNYVTF |
| 88 | VH-CDR3, AbM | RGPRDSWFGY |
| 89 | VL-CDR1, Chothia | RSSQKIVHRNANTYLE |
| 90 | VL-CDR2, Chothia | TVSNRFS |
| 91 | VL-CDR3, Chothia | FQGSYLPLT |
| 92 | VH-CDR1, Chothia | GFTFSSF |
| 93 | VH-CDR2, Chothia | RSETNNYV |
| 94 | VH-CDR3, Chothia | RGPRDSWFGY |
| 95 | VL-CDR1, Contact | VHRNANTYLEWY |
| 96 | VL-CDR2, Contact | LLIYTVSNRF |
| 97 | VL-CDR3, Contact | FQGSYLPL |
| 98 | VH-CDR1, Contact | SSFALN |
| 99 | VH-CDR2, Contact | WVGHIRSETNNYVTF |
| 100 | VH-CDR3, Contact | VRRGPRDSWFG |
| 101 | VL-CDR1, IMGT | QKIVHRNANTY |
| 102 | VL-CDR2, IMGT | TV |
| 103 | VL-CDR3, IMGT | FQGSYLPLT |
| 104 | VH-CDR1, IMGT | GFTFSSFA |
| 105 | VH-CDR2, IMGT | IRSETNNYV |
| 106 | VH-CDR3, IMGT | VRRGPRDSWFGY |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| 107 | DNA encoding light chain | atgtccgtgccta-cacaggttctgggactgctgctgctgtgg ctgaccgacgccagatgcgacatcgt-gatgacccagtctcca ctgagcctgcctgtgacactgggagagccagcctc-catctcc tgccggtcctctcagaaaatcgtgcaccggaacgc-caacacc tacctg-gaatggtatctgcagaagcccggccagtctcctcag ctgctgatctacaccgtgtc-caaccggttctctggcgtgccc gatagattctccggctctggctctggcaccgactt-caccctg aagatctccagagtggaagccgaggacctgggcgtgtac-tac tgcttccaaggctcc-tacctgcctctgacctttggcggcgga acaaaggtggaaat-caagcggacagtggccgctccttccgtg ttcatcttccaccttccgacgagcagct-gaagtccggcaca gcttctgtcgtgtgcctgctgaacaacttctaccctcgg-gaa gccaaggtgcagtg-gaaggtggacaatgccctgcagtccggc aactcccaagagtctgtgaccgagcaggactc-caaggacagc acctacagcctgtcctccacactgaccctgtc-caaggccgac tacgagaagcacaaggtgtacgcctgcgaagtgacc-catcag ggcctgtctagccctgtgaccaagtctttt-caaccggggcgag tgt |
| 108 | DNA encoding heavy chain | atg-gaatggtcctgggtgttcctgttcttcctgtccgtgacc accggcgtgcactctgaagtgcagctggtt-gaatctggcggc ggattggttcagcctggcggatctctga-gactgtcttgtgcc gcctccggcttcaccttctctagcttcgctct-gaactgggtc cgacaggctcctggcaaaggactggaatgggtcggaca-catc agatccgagacaaacaactacgtgaccttc-tacgccgccagc gtgaagggcagatt-caccgtgtccagagatgactcccagaac accgcctacctgcagatgaactccct-gaaaaccgaggacacc gccacctac-tactgcgtgcgaagaggccctcgggacagttgg ttcggatat-tggggacagggcaccctcgtgaccgtgtcctct gcttctac-caagggacccagcgtgttccctctggctccttcc agcaagtctacctctggcg-gaacagctgctctgggctgcctg gtcaaggactactttcctgagcctgtgacagtgtcctg-gaac tctggcgctctga-catctggcgtgcacacctttccagctgtg ctgcagtcctccggcctgtactctctgtcctctgtcgtgaca gtgccctccagctctctgggaacccagacccta-catctgcaat gtgaaccacaagccttccaacac-caaggtggacaagaaggtg gaacccaagtcctgcgacaagacccacacctgtcctc-catgt cctgctccagaagctgctggcggcccttccgtgtttctgttc cctccaaagcctaaggacaccctgtacat-cacccgcgagcct gaagtgacctgcgtggtggtggatgtgtct-cacgaggacccc gaagtgaagttcaattggtacgtggacggcgtg-gaagtgcac |

TABLE 14 -continued

Sequences disclosed in the specification

| SEQ ID NO | Sequence Description | Sequence (SEQ ID NO: 107 and 108 are nucleotide sequences, the rest are amino acid sequences) |
|---|---|---|
| | | aacgccaagaccaagcctagagaggaacagtacaactc-<br>cacc<br>tacagagtggtgtccgtgctgaccgtgctgcaccaggat-<br>tgg<br>ctgaacggcaaagagtacaagtgcaaggtgtc-<br>caacaaggcc<br>ctgcctgctcctatcgaaaagaccatctccaaggc-<br>caagggc<br>cagcctagggaacccccaggtttacaccttgcctc-<br>catctcgg<br>gacgagctgac-<br>caagaaccaggtgtccctgacctgcctcgtg<br>aagggattctaccccctccgatatcgccgtggaatgg-<br>gagtct<br>aatggccagcctgagaacaactacaa-<br>gacaacccctcctgtg<br>ctggactccgacggctcattctttctgtactc-<br>caagctgaca<br>gtggacaagtcca-<br>gatggcagcagggcaacgtgttctcctgc<br>agcgtgatgcacgaggccctgcacaatcacta-<br>cacccagaag<br>tccctgtctctgtcccctggcaaa |
| 109 | Peptide | GAEIVYK(pS)PVVSGDT(pS)PRHLSNVS(pS)<br>TGSIDMVD<br>(pS)PQLATLADEVSASLAKQGL |

What we claim is:

1. An antibody or antigen binding fragment thereof that binds to tau-pS413, comprising:
   (a) a heavy chain variable region complementarity determining region 1 (VH-CDR1) comprising the amino acid sequence of SEQ ID NO:41; a heavy chain variable region complementarity determining region 2 (VH-CDR2) comprising the amino acid sequence of SEQ ID NO:42; and a heavy chain variable region complementarity determining region 3 (VH-CDR3) comprising the amino acid sequence of SEQ ID NO:43; and
   a light chain variable region complementarity determining region 1 (VL-CDR1) comprising the amino acid sequence of SEQ ID NO:29; a light chain variable region complementarity determining region 2 (VL-CDR2) comprising the amino acid sequence of SEQ ID NO:30; and a light chain variable region complementarity determining region 3 (VL-CDR3) comprising the amino acid sequence of SEQ ID NO:31;
   (b) a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and
   a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35;
   (c) a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and
   a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39;
   (d) a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and
   a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27;
   (e) a VH-CDR1 comprising the amino acid sequence of SEQ ID NO:41; a VH-CDR2 comprising the amino acid sequence of SEQ ID NO:42; and a VH-CDR3 comprising the amino acid sequence of SEQ ID NO:43; and
   a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19;

(f) a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and
a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31;

(g) a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and
a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35;

(h) a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and
a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39;

(i) a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and
a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27;

(j) a VH-CDR1 comprising the amino acid sequence of SEQ ID NO:45; a VH-CDR2 comprising the amino acid sequence of SEQ ID NO:46; and a VH-CDR3 comprising the amino acid sequence of SEQ ID NO:47; and
a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19;

(k) a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and
a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31;

(l) a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and
a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35;

(m) a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and
a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39;

(n) a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and
a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27;

(o) a VH-CDR1 comprising the amino acid sequence of SEQ ID NO:49; a VH-CDR2 comprising the amino acid sequence of SEQ ID NO:50; and a VH-CDR3 comprising the amino acid sequence of SEQ ID NO:51; and
a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19;

(p) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and
a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31;

(q) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and
a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35;

(r) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and
a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39;

(s) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and
a VL-CDR1 comprising the amino acid sequence of SEQ ID NO:25; a VL-CDR2 comprising the amino acid sequence of SEQ ID NO:26; and a VL-CDR3 comprising the amino acid sequence of SEQ ID NO:27;

(t) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:17; a VL-CDR2 comprising the amino acid sequence of SEQ ID NO:18; and a VL-CDR3 comprising the amino acid sequence of SEQ ID NO:19;
(u) a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and
a VL-CDR1 comprising the amino acid sequence of SEQ ID NO:29; a VL-CDR2 comprising the amino acid sequence of SEQ ID NO:30; and a VL-CDR3 comprising the amino acid sequence of SEQ ID NO:31;
(v) a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and
a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35;
(w) a VH-CDR1 comprising the amino acid sequence of SEQ ID NO:21; a VH-CDR2 comprising the amino acid sequence of SEQ ID NO:22; and a VH-CDR3 comprising the amino acid sequence of SEQ ID NO:23; and
a VL-CDR1 comprising the amino acid sequence of SEQ ID NO:37; a VL-CDR2 comprising the amino acid sequence of SEQ ID NO:38; and a VL-CDR3 comprising the amino acid sequence of SEQ ID NO:39;
(x) a VH-CDR1 comprising the amino acid sequence of SEQ ID NO:86; a VH-CDR2 comprising the amino acid sequence of SEQ ID NO:87; and a VH-CDR3 comprising the amino acid sequence of SEQ ID NO:88; and
a VL-CDR1 comprising the amino acid sequence of SEQ ID NO:83; a VL-CDR2 comprising the amino acid sequence of SEQ ID NO:84; and a VL-CDR3 comprising the amino acid sequence of SEQ ID NO:85;
(y) a VH-CDR1 comprising the amino acid sequence of SEQ ID NO:92; a VH-CDR2 comprising the amino acid sequence of SEQ ID NO:93; and a VH-CDR3 comprising the amino acid sequence of SEQ ID NO:94; and
a VL-CDR1 comprising the amino acid sequence of SEQ ID NO:89; a VL-CDR2 comprising the amino acid sequence of SEQ ID NO:90; and a VL-CDR3 comprising the amino acid sequence of SEQ ID NO:91;
(z) a VH-CDR1 comprising the amino acid sequence of SEQ ID NO:98; a VH-CDR2 comprising the amino acid sequence of SEQ ID NO:99; and a VH-CDR3 comprising the amino acid sequence of SEQ ID NO:100; and
a VL-CDR1 comprising the amino acid sequence of SEQ ID NO:95; a VL-CDR2 comprising the amino acid sequence of SEQ ID NO:96; and a VL-CDR3 comprising the amino acid sequence of SEQ ID NO:97;
(aa) a VH-CDR1 comprising the amino acid sequence of SEQ ID NO:104; a VH-CDR2 comprising the amino acid sequence of SEQ ID NO:105; and a VH-CDR3 comprising the amino acid sequence of SEQ ID NO:106; and
a VL-CDR1 comprising the amino acid sequence of SEQ ID NO:101; a VL-CDR2 comprising the amino acid sequence of SEQ ID NO:102; and a VL-CDR3 comprising the amino acid sequence of SEQ ID NO:103;
(bb) a VH-CDR1, a VH-CDR2, and a VH-CDR3 of a heavy chain variable region (VH) comprising the amino acid sequence of SEQ ID NO:44; and
a VL-CDR1, a VL-CDR2, and a VL-CDR3 of a light chain variable region (VL) comprising the amino acid sequence of SEQ ID NO:32;
(cc) a VH-CDR1, a VH-CDR2, and a VH-CDR3 of a VH comprising the amino acid sequence of SEQ ID NO:44; and
a VL-CDR1, a VL-CDR2, and a VL-CDR3 of a VL comprising the amino acid sequence of SEQ ID NO:36;
(dd) a VH-CDR1, a VH-CDR2, and a VH-CDR3 of a VH comprising the amino acid sequence of SEQ ID NO:44; and
a VL-CDR1, a VL-CDR2, and a VL-CDR3 of a VL comprising the amino acid sequence of SEQ ID NO:40;
(ee) a VH-CDR1, a VH-CDR2, and a VH-CDR3 of a VH comprising the amino acid sequence of SEQ ID NO:44; and
a VL-CDR1, a VL-CDR2, and a VL-CDR3 of a VL comprising the amino acid sequence of SEQ ID NO:28;
(ff) a VH-CDR1, a VH-CDR2, and a VH-CDR3 of a VH comprising the amino acid sequence of SEQ ID NO:44; and
a VL-CDR1, a VL-CDR2, and a VL-CDR3 of a VL comprising the amino acid sequence of SEQ ID NO:20;
(gg) a VH-CDR1, a VH-CDR2, and a VH-CDR3 of a VH comprising the amino acid sequence of SEQ ID NO:48; and
a VL-CDR1, a VL-CDR2, and a VL-CDR3 of a VL comprising the amino acid sequence of SEQ ID NO:32;
(hh) a VH-CDR1, a VH-CDR2, and a VH-CDR3 of a VH comprising the amino acid sequence of SEQ ID NO:48; and
a VL-CDR1, a VL-CDR2, and a VL-CDR3 of a VL comprising the amino acid sequence of SEQ ID NO:36;
(ii) a VH-CDR1, a VH-CDR2, and a VH-CDR3 of a VH comprising the amino acid sequence of SEQ ID NO:48; and
a VL-CDR1, a VL-CDR2, and a VL-CDR3 of a VL comprising the amino acid sequence of SEQ ID NO:40;
(jj) a VH-CDR1, a VH-CDR2, and a VH-CDR3 of a VH comprising the amino acid sequence of SEQ ID NO:48; and
a VL-CDR1, a VL-CDR2, and a VL-CDR3 of a VL comprising the amino acid sequence of SEQ ID NO:28;
(kk) a VH-CDR1, a VH-CDR2, and a VH-CDR3 of a VH comprising the amino acid sequence of SEQ ID NO:48; and
a VL-CDR1, a VL-CDR2, and a VL-CDR3 of a VL comprising the amino acid sequence of SEQ ID NO:20;
(ll) a VH-CDR1, a VH-CDR2, and a VH-CDR3 of a VH comprising the amino acid sequence of SEQ ID NO:52; and
a VL-CDR1, a VL-CDR2, and a VL-CDR3 of a VL comprising the amino acid sequence of SEQ ID NO:32;
(mm) a VH-CDR1, a VH-CDR2, and a VH-CDR3 of a VH comprising the amino acid sequence of SEQ ID NO:52; and
a VL-CDR1, a VL-CDR2, and a VL-CDR3 of a VL comprising the amino acid sequence of SEQ ID NO:36;
(nn) a VH-CDR1, a VH-CDR2, and a VH-CDR3 of a VH comprising the amino acid sequence of SEQ ID NO:52; and
a VL-CDR1, a VL-CDR2, and a VL-CDR3 of a VL comprising the amino acid sequence of SEQ ID NO:40;

(oo) a VH-CDR1, a VH-CDR2, and a VH-CDR3 of a VH comprising the amino acid sequence of SEQ ID NO:52; and
a VL-CDR1, a VL-CDR2, and a VL-CDR3 of a VL comprising the amino acid sequence of SEQ ID NO:28;
(pp) a VH-CDR1, a VH-CDR2, and a VH-CDR3 of a VH comprising the amino acid sequence of SEQ ID NO:52; and
a VL-CDR1, a VL-CDR2, and a VL-CDR3 of a VL comprising the amino acid sequence of SEQ ID NO:20;
(qq) a VH-CDR1, a VH-CDR2, and a VH-CDR3 of a VH comprising the amino acid sequence of SEQ ID NO:56; and
a VL-CDR1, a VL-CDR2, and a VL-CDR3 of a VL comprising the amino acid sequence of SEQ ID NO:32;
(rr) a VH-CDR1, a VH-CDR2, and a VH-CDR3 of a VH comprising the amino acid sequence of SEQ ID NO:56; and
a VL-CDR1, a VL-CDR2, and a VL-CDR3 of a VL comprising the amino acid sequence of SEQ ID NO:36;
(ss) a VH-CDR1, a VH-CDR2, and a VH-CDR3 of a VH comprising the amino acid sequence of SEQ ID NO:56; and
a VL-CDR1, a VL-CDR2, and a VL-CDR3 of a VL comprising the amino acid sequence of SEQ ID NO:40;
(tt) a VH-CDR1, a VH-CDR2, and a VH-CDR3 of a VH comprising the amino acid sequence of SEQ ID NO:56; and
a VL-CDR1, a VL-CDR2, and a VL-CDR3 of a VL comprising the amino acid sequence of SEQ ID NO:28;
(uu) a VH-CDR1, a VH-CDR2, and a VH-CDR3 of a VH comprising the amino acid sequence of SEQ ID NO:56; and
a VL-CDR1, a VL-CDR2, and a VL-CDR3 of a VL comprising the amino acid sequence of SEQ ID NO:20;
(vv) a VH-CDR1, a VH-CDR2, and a VH-CDR3 of a VH comprising the amino acid sequence of SEQ ID NO:24; and
a VL-CDR1, a VL-CDR2, and a VL-CDR3 of a VL comprising the amino acid sequence of SEQ ID NO:32;
(ww) a VH-CDR1, a VH-CDR2, and a VH-CDR3 of a VH comprising the amino acid sequence of SEQ ID NO:24; and
a VL-CDR1, a VL-CDR2, and a VL-CDR3 of a VL comprising the amino acid sequence of SEQ ID NO:36; or
(xx) a VH-CDR1, a VH-CDR2, and a VH-CDR3 of a VH comprising the amino acid sequence of SEQ ID NO:24; and
a VL-CDR1, a VL-CDR2, and a VL-CDR3 of a VL comprising the amino acid sequence of SEQ ID NO:40.

2. The antibody or antigen-binding fragment of claim 1, comprising:
(a) a VH having at least 90% amino acid sequence identity to the amino acid sequence of SEQ ID NO:44, and a VL having at least 90% amino acid sequence identity to the amino acid sequence of SEQ ID NO:32;
(b) a VH having at least 90% amino acid sequence identity to the amino acid sequence of SEQ ID NO:44, and a VL having at least 90% amino acid sequence identity to the amino acid sequence of SEQ ID NO:36;
(c) a VH having at least 90% amino acid sequence identity to the amino acid sequence of SEQ ID NO:44, and a VL having at least 90% amino acid sequence identity to the amino acid sequence of SEQ ID NO:40;
(d) a VH having at least 90% amino acid sequence identity to the amino acid sequence of SEQ ID NO:44, and a VL having at least 90% amino acid sequence identity to the amino acid sequence of SEQ ID NO:28;
(e) a VH having at least 90% amino acid sequence identity to the amino acid sequence of SEQ ID NO:44, and a VL having at least 90% amino acid sequence identity to the amino acid sequence of SEQ ID NO:20;
(f) a VH having at least 90% amino acid sequence identity to the amino acid sequence of SEQ ID NO:48, and a VL having at least 90% amino acid sequence identity to the amino acid sequence of SEQ ID NO:32;
(g) a VH having at least 90% amino acid sequence identity to the amino acid sequence of SEQ ID NO:48, and a VL having at least 90% amino acid sequence identity to the amino acid sequence of SEQ ID NO:36;
(h) a VH having at least 90% amino acid sequence identity to the amino acid sequence of SEQ ID NO:48, and a VL having at least 90% amino acid sequence identity to the amino acid sequence of SEQ ID NO:40;
(i) a VH having at least 90% amino acid sequence identity to the amino acid sequence of SEQ ID NO:48, and a VL having at least 90% amino acid sequence identity to the amino acid sequence of SEQ ID NO:28;
(j) a VH having at least 90% amino acid sequence identity to the amino acid sequence of SEQ ID NO:48, and a VL having at least 90% amino acid sequence identity to the amino acid sequence of SEQ ID NO:20;
(k) a VH having at least 90% amino acid sequence identity to the amino acid sequence of SEQ ID NO:52, and a VL having at least 90% amino acid sequence identity to the amino acid sequence of SEQ ID NO:32;
(l) a VH having at least 90% amino acid sequence identity to the amino acid sequence of SEQ ID NO:52, and a VL having at least 90% amino acid sequence identity to the amino acid sequence of SEQ ID NO:36;
(m) a VH having at least 90% amino acid sequence identity to the amino acid sequence of SEQ ID NO:52, and a VL having at least 90% amino acid sequence identity to the amino acid sequence of SEQ ID NO:40;
(n) a VH having at least 90% amino acid sequence identity to the amino acid sequence of SEQ ID NO:52, and a VL having at least 90% amino acid sequence identity to the amino acid sequence of SEQ ID NO:28;
(o) a VH having at least 90% amino acid sequence identity to the amino acid sequence of SEQ ID NO:52, and a VL having at least 90% amino acid sequence identity to the amino acid sequence of SEQ ID NO:20;
(p) a VH having at least 90% amino acid sequence identity to the amino acid sequence of SEQ ID NO:56, and a VL having at least 90% amino acid sequence identity to the amino acid sequence of SEQ ID NO:32;
(q) a VH having at least 90% amino acid sequence identity to the amino acid sequence of SEQ ID NO:56, and a VL having at least 90% amino acid sequence identity to the amino acid sequence of SEQ ID NO:36;
(r) a VH having at least 90% amino acid sequence identity to the amino acid sequence of SEQ ID NO:56, and a VL having at least 90% amino acid sequence identity to the amino acid sequence of SEQ ID NO:40;
(s) a VH having at least 90% amino acid sequence identity to the amino acid sequence of SEQ ID NO:56, and a VL having at least 90% amino acid sequence identity to the amino acid sequence of SEQ ID NO:28;
(t) a VH having at least 90% amino acid sequence identity to the amino acid sequence of SEQ ID NO:56, and a VL having at least 90% amino acid sequence identity to the amino acid sequence of SEQ ID NO:20;

(u) a VH having at least 90% amino acid sequence identity to the amino acid sequence of SEQ ID NO:24, and a VL having at least 90% amino acid sequence identity to the amino acid sequence of SEQ ID NO:32;

(v) a VH having at least 90% amino acid sequence identity to the amino acid sequence of SEQ ID NO:24, and a VL having at least 90% amino acid sequence identity to the amino acid sequence of SEQ ID NO:36; or (w) a VH having at least 90% amino acid sequence identity to the amino acid sequence of SEQ ID NO:24, and a VL having at least 90% amino acid sequence identity to the amino acid sequence of SEQ ID NO:40.

3. The antibody or antigen binding fragment thereof of claim 1, comprising:

(a) a VH having the amino acid sequence of SEQ ID NO:44, and a VL having the amino acid sequence of SEQ ID NO:32;

(b) a VH having the amino acid sequence of SEQ ID NO:44, and a VL having the amino acid sequence of SEQ ID NO:36;

(c) a VH having the amino acid sequence of SEQ ID NO:44, and a VL having the amino acid sequence of SEQ ID NO:40;

(d) a VH having the amino acid sequence of SEQ ID NO:44, and a VL having the amino acid sequence of SEQ ID NO:28;

(e) a VH having the amino acid sequence of SEQ ID NO:44, and a VL having the amino acid sequence of SEQ ID NO:20;

(f) a VH having the amino acid sequence of SEQ ID NO:48, and a VL having the amino acid sequence of SEQ ID NO:32;

(g) a VH having the amino acid sequence of SEQ ID NO:48, and a VL having the amino acid sequence of SEQ ID NO:36;

(h) a VH having the amino acid sequence of SEQ ID NO:48, and a VL having the amino acid sequence of SEQ ID NO:40;

(i) a VH having the amino acid sequence of SEQ ID NO:48, and a VL having the amino acid sequence of SEQ ID NO:28;

(j) a VH having the amino acid sequence of SEQ ID NO:48, and a VL having the amino acid sequence of SEQ ID NO:20;

(k) a VH having the amino acid sequence of SEQ ID NO:52, and a VL having the amino acid sequence of SEQ ID NO:32;

(l) a VH having the amino acid sequence of SEQ ID NO:52, and a VL having the amino acid sequence of SEQ ID NO:36;

(m) a VH having the amino acid sequence of SEQ ID NO:52, and a VL having the amino acid sequence of SEQ ID NO:40;

(n) a VH having the amino acid sequence of SEQ ID NO:52, and a VL having the amino acid sequence of SEQ ID NO:28;

(o) a VH having the amino acid sequence of SEQ ID NO:52, and a VL having the amino acid sequence of SEQ ID NO:20;

(p) a VH having the amino acid sequence of SEQ ID NO:56, and a VL having the amino acid sequence of SEQ ID NO:32;

(q) a VH having the amino acid sequence of SEQ ID NO:56, and a VL having the amino acid sequence of SEQ ID NO:36;

(r) a VH having the amino acid sequence of SEQ ID NO:56, and a VL having the amino acid sequence of SEQ ID NO:40;

(s) a VH having the amino acid sequence of SEQ ID NO:56, and a VL having the amino acid sequence of SEQ ID NO:28;

(t) a VH having the amino acid sequence of SEQ ID NO:56, and a VL having the amino acid sequence of SEQ ID NO:20;

(u) a VH having the amino acid sequence of SEQ ID NO:24, and a VL having the amino acid sequence of SEQ ID NO:32;

(v) a VH having the amino acid sequence of SEQ ID NO:24, and a VL having the amino acid sequence of SEQ ID NO:36; or (w) a VH having the amino acid sequence of SEQ ID NO:24, and a VL having the amino acid sequence of SEQ ID NO:40.

4. The antibody or antigen-binding fragment of claim 3, further comprising:

(a) a heavy chain constant region having the amino acid sequence of SEQ ID NO:59, 60, 61, 62, 63, 64, 65, 66, 67, or 68; and (b) a light chain constant region having the amino acid sequence of SEQ ID NO:57 or 58.

5. An antibody or antigen binding fragment thereof that binds to tau-pS413, comprising (a) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35; or (b) a VH-CDR1, a VH-CDR2, and a VH-CDR3 of a VH comprising the amino acid sequence of SEQ ID NO:56; and a VL-CDR1, a VL-CDR2, and a VL-CDR3 of a VL comprising the amino acid sequence of SEQ ID NO:36.

6. An antibody or antigen binding fragment thereof that binds to tau-pS413, comprising a VH comprising the amino acid sequence of SEQ ID NO:56 and a VL comprising the amino acid sequence of SEQ ID NO:36.

7. The antibody of claim 5, comprising:

(a) a light chain comprising the amino acid sequence of SEQ ID NO:71 and a heavy chain comprising the amino acid sequence of SEQ ID NO:72;

(b) a light chain comprising the amino acid sequence of SEQ ID NO:73 and a heavy chain comprising the amino acid sequence of SEQ ID NO:74; or (c) a light chain comprising the amino acid sequence of SEQ ID NO:75 and a heavy chain comprising the amino acid sequence of SEQ ID NO:76.

8. The antibody or antigen binding fragment thereof of claim 1, having an equilibrium dissociation constant (KD) of $1 \times 10^{-8}$ M or less for tau-pS413.

9. The antibody or antigen binding fragment thereof of claim 8, having an KD of $2 \times 10^{-9}$ M or less for tau-pS413.

10. The antibody or antigen binding fragment thereof of claim 9, wherein the KD is measured by Biacore with the antibody or antigen binding fragment thereof being immobilized.

11. An isolated nucleic acid, encoding:
   (a) the VH of the antibody or antigen binding fragment thereof of claim 3;
   (b) the VL of the antibody or antigen binding fragment thereof of claim 3; or
   (c) the VH and the VL of the antibody or antigen binding fragment thereof of claim 3.

12. An expression vector comprising the isolated nucleic acid of claim 11.

13. A host cell comprising the expression vector of claim 12.

14. A method of producing an antibody or antigen binding fragment thereof, comprising:
   (a) culturing the host cell of claim 13 under conditions wherein the antibody or antigen binding fragment thereof is expressed; and
   (b) harvesting the antibody or antigen binding fragment thereof.

15. A composition comprising the antibody or antigen binding fragment thereof of claim 1, and a pharmaceutically acceptable carrier.

16. A method of treating tauopathy in a subject, comprising administering to the subject an effective amount of the antibody or antigen binding fragment thereof of claim 1.

17. The method of claim 16, wherein the tauopathy is Alzheimer's disease, corticobasal degeneration, progressive supranuclear palsy, Pick's disease, argyrophilic grain dementia (argyrophilic grain disease), multiple system tauopathy with presenile dementia (MSTD), frontotemporal dementia and parkinsonism linked to chromosome 17 (FTDP-17), dementia with neurofibrillary tangles, diffuse neurofibrillary tangle with calcification (DNTC), white matter tauopathy with globular glial inclusions (WMT-GGI), frontotemporal lobar degeneration with tau pathology (FTLD-tau), Economo's encephalitis sequela, subacute sclerosing panencephalitis, or boxer's encephalopathy.

18. A method of decreasing the amount of tau-pS413 in the brain of a subject in need thereof, the method comprising administering to the subject an effective amount of the antibody or antigen binding fragment thereof of claim 1.

19. The method of claim 17, further comprising administering to the subject an additional agent.

20. The method of claim 19, wherein the additional agent is selected from the group consisting of a cholinesterase inhibitor, an NMDA receptor antagonist, an amyloid beta peptide aggregation inhibitor, an antioxidant, a gamma-secretase modulator, a nerve growth factor (NGF) mimic, a PPARγ agonist, an HMS-CoA reductase inhibitor, a statin, an ampakine, a calcium channel blocker, a GABA receptor antagonist, a glycogen synthase kinase inhibitor, an intravenous immunoglobulin, a muscarinic receptor agonist, a nicotinic receptor modulator, an active or passive amyloid beta peptide for immunization, a phosphodiesterase inhibitor, a serotonin receptor antagonist, an anti-amyloid beta peptide antibody, a growth hormone, a neurotrophic factor, a brain-derived neurotrophic factor (BDNF), a nerve growth factor (NGF), a neurotrophin-4/5, a fibroblast growth factor, neurotrophin (NT)-3, erythropoietin (EPO), hepatocyte growth factor (HGF), epidermal growth factor (EGF), transforming growth factor (TGF)-aplha, TGF-beta, vascular endothelial growth factor (VEGF), an interleukin-1 receptor antagonist (IL-lra), a ciliary neurotrophic factor (CNTF), a glial-derived neurotrophic factor (GDNF), neurturin, platelet-derived growth factor (PDGF), heregulin, neuregulin, artemin, persephin, an interleukin, glial cell line derived neurotrophic factor (GFR), granulocyte-colony stimulating factor (CSF), granulocyte-macrophage-CSF, a netrin, cardiotrophin-1, leukemia inhibitory factor (LIF), midkine, pleiotrophin, a bone morphogenetic protein (BMP), a saposin, a semaphoring, stem cell factor (SCF), and a different anti-tau antibody, or a combination thereof.

21. A monoclonal antibody that binds to tau-pS413, comprising
   (a) a VH-CDR1 comprising the amino acid sequence of SEQ ID NO:53; a VH-CDR2 comprising the amino acid sequence of SEQ ID NO:54; and a VH-CDR3 comprising the amino acid sequence of SEQ ID NO:55; and
   (b) a VL-CDR1 comprising the amino acid sequence of SEQ ID NO:33; a VL-CDR2 comprising the amino acid sequence of SEQ ID NO:34; and a VL-CDR3 comprising the amino acid sequence of SEQ ID NO:35.

22. The monoclonal antibody of claim 21 that comprises a VH comprising the amino acid sequence of SEQ ID NO:56 and a VL comprising the amino acid sequence of SEQ ID NO:36.

23. An antibody that binds to tau-pS413, comprising a light chain comprising the amino acid sequence of SEQ ID NO:73 and a heavy chain comprising the amino acid sequence of SEQ ID NO:74.

24. A composition comprising the monoclonal antibody of claim 21 and a pharmaceutically acceptable carrier.

25. A composition comprising the monoclonal antibody of claim 22 and a pharmaceutically acceptable carrier.

26. A method of treating tauopathy in a subject, comprising administering to the subject an effective amount of the monoclonal antibody of 21, wherein the tauopathy is Alzheimer's disease.

27. A method of decreasing the amount of tau-pS413 in the brain of a subject in need thereof, the method comprising administering to the subject an effective amount of the monoclonal antibody of claim 21.

28. The method of claim 20, wherein the cholinesterase inhibitor is selected from the group consisting of donepezil, galantamine, rivastigmine, and tacrine.

29. The method of claim 20, wherein the NMDA receptor antagonist is memantine.

30. An isolated nucleic acid encoding:
   (a) a light chain comprising the amino acid sequence of SEQ ID NO:73;
   (b) a heavy chain comprising the amino acid sequence of SEQ ID NO:74; or
   (c) a light chain comprising the amino acid sequence of SEQ ID NO:73 and a heavy chain comprising the amino acid sequence of SEQ ID NO:74.

31. An expression vector comprising the isolated nucleic acid of claim 30.

32. A host cell comprising the expression vector of claim 31.

33. A method of producing an antibody or antigen binding fragment thereof, comprising:
   (a) culturing the host cell of claim 32 under conditions wherein the antibody or antigen binding fragment thereof is expressed; and
   (b) harvesting the antibody or antigen binding fragment thereof.

* * * * *

UNITED STATES PATENT AND TRADEMARK OFFICE
CERTIFICATE OF CORRECTION

PATENT NO. : 11,702,467 B2
APPLICATION NO. : 17/355529
DATED : July 18, 2023
INVENTOR(S) : Jeanne E. Baker et al.

Page 1 of 1

It is certified that error appears in the above-identified patent and that said Letters Patent is hereby corrected as shown below:

On the Title Page

(60) is listed as:
(60) Provisional application No. 63/044,921, filed on Jun. 25, 2020.

Should be listed as:
(60) Provisional application No. 63/044,291, filed on Jun. 25, 2020.

Signed and Sealed this
Twenty-first Day of May, 2024

Katherine Kelly Vidal
*Director of the United States Patent and Trademark Office*